(12) United States Patent
Charthad et al.

(10) Patent No.: US 12,407,558 B2
(45) Date of Patent: Sep. 2, 2025

(54) SYSTEMS, DEVICES, AND METHODS FOR ESTABLISHING A WIRELESS LINK IN A HETEROGENEOUS MEDIUM

(71) Applicant: uLink Labs, Inc., San Mateo, CA (US)

(72) Inventors: Jayant Charthad, Menlo Park, CA (US); Marcus Weber, San Francisco, CA (US); Arsenii Telichko, San Mateo, CA (US)

(73) Assignee: uLink Labs, Inc., San Mateo, CA (US)

( * ) Notice: Subject to any disclaimer, the term of this patent is extended or adjusted under 35 U.S.C. 154(b) by 38 days.

(21) Appl. No.: 18/393,412

(22) Filed: Dec. 21, 2023

(65) Prior Publication Data

US 2024/0348482 A1    Oct. 17, 2024

Related U.S. Application Data

(63) Continuation of application No. PCT/US2022/035574, filed on Jun. 29, 2022.
(Continued)

(51) Int. Cl.
*H04L 27/26* (2006.01)
*H04B 7/0417* (2017.01)

(52) U.S. Cl.
CPC ....... *H04L 27/2627* (2013.01); *H04B 7/0417* (2013.01)

(58) Field of Classification Search
CPC ............. H04L 27/2627; H04L 27/2628; H04L 27/2634; H04L 27/2639; H04B 7/0417; H04B 11/00; H04B 5/22; H04B 5/79
See application file for complete search history.

(56) References Cited

U.S. PATENT DOCUMENTS

| 4,227,407 A | 10/1980 | Drost |
| 5,078,148 A | 1/1992 | Nassi et al. |

(Continued)

FOREIGN PATENT DOCUMENTS

| CN | 108430570 A | 8/2018 |
| EP | 2 162 185 B1 | 7/2015 |

(Continued)

OTHER PUBLICATIONS

Aubry, J-F. et al. (2008). "Transcostal high-intensity-focused ultrasound: ex vivo adaptive focusing feasibility study," Phys. Med. Biol. 53:2937-2951.
(Continued)

*Primary Examiner* — Khanh C Tran
(74) *Attorney, Agent, or Firm* — COOLEY LLP

(57) ABSTRACT

Described herein are systems, devices, and methods for establishing a wireless link between two or more wireless devices. In some variations, a wireless system may comprise a first device configured to transmit a feedback signal with a first duration. The system may also comprise a second device comprising a transducer array and a processor. The transducer array may be configured to receive the feedback signal on one or more transducer elements of the transducer array for a second duration. The processor may be configured to process the feedback signal received in the second duration by one or more transducer elements of the transducer array to generate feedback signal data. The processor may be further configured to determine a transducer array configuration based at least in part on the feedback signal data. The second device may be configured to exchange one or more wireless signals with the first device using the transducer array configuration.

20 Claims, 18 Drawing Sheets

Related U.S. Application Data

(60) Provisional application No. 63/216,282, filed on Jun. 29, 2021.

(56) References Cited

U.S. PATENT DOCUMENTS

| | | | |
|---|---|---|---|
| 5,289,821 A | 3/1994 | Swartz | |
| 5,476,488 A | 12/1995 | Morgan et al. | |
| 5,487,760 A | 1/1996 | Villafana | |
| 5,683,432 A | 11/1997 | Goedeke et al. | |
| 6,053,873 A | 4/2000 | Govari et al. | |
| 6,087,810 A | 7/2000 | Yoshida | |
| 6,239,724 B1 | 5/2001 | Doron et al. | |
| 6,277,078 B1 | 8/2001 | Porat et al. | |
| 6,398,734 B1 | 6/2002 | Cimochowski et al. | |
| 6,432,050 B1 | 8/2002 | Porat et al. | |
| 6,475,170 B1 | 11/2002 | Doron et al. | |
| 6,585,763 B1 | 7/2003 | Keilman et al. | |
| 6,628,989 B1 | 9/2003 | Penner et al. | |
| 6,716,166 B2 | 4/2004 | Govari | |
| 6,764,446 B2 | 7/2004 | Wolinsky et al. | |
| 6,792,310 B1 | 9/2004 | Turcott et al. | |
| 6,982,646 B2 | 1/2006 | Rodgers et al. | |
| 7,024,248 B2 | 4/2006 | Penner et al. | |
| 7,198,603 B2 | 4/2007 | Penner et al. | |
| 7,201,749 B2 | 4/2007 | Govari et al. | |
| 7,273,457 B2 | 9/2007 | Penner | |
| 7,416,530 B2 | 8/2008 | Turner et al. | |
| 7,489,967 B2 | 2/2009 | Von Arx et al. | |
| 7,549,960 B2 | 6/2009 | Govari | |
| 7,550,978 B2 | 6/2009 | Joy et al. | |
| 7,558,616 B2 | 7/2009 | Govari et al. | |
| 7,575,550 B1 | 8/2009 | Govari | |
| 7,616,990 B2 | 11/2009 | Chavan et al. | |
| 7,617,001 B2 | 11/2009 | Penner et al. | |
| 7,634,318 B2 | 12/2009 | Tran et al. | |
| 7,641,619 B2 | 1/2010 | Penner | |
| 7,650,185 B2 | 1/2010 | Maile et al. | |
| 7,679,355 B2 | 3/2010 | Allen et al. | |
| 7,710,103 B2 | 5/2010 | Powers et al. | |
| 7,744,542 B2 | 6/2010 | Piaget et al. | |
| 7,756,587 B2 | 7/2010 | Penner et al. | |
| 7,765,001 B2 | 7/2010 | Echt et al. | |
| 7,813,801 B2 | 10/2010 | Youker et al. | |
| 7,813,808 B1 | 10/2010 | Doron et al. | |
| 7,862,508 B2 | 1/2011 | Davies et al. | |
| 7,912,548 B2 | 3/2011 | Mi et al. | |
| 7,930,031 B2 | 4/2011 | Penner | |
| 7,934,508 B2 | 5/2011 | Behm | |
| 7,949,396 B2 | 5/2011 | Mi et al. | |
| 7,953,613 B2 | 5/2011 | Gizewski | |
| 7,955,268 B2 | 6/2011 | Huelskamp | |
| 7,955,269 B2 | 6/2011 | Stahmann | |
| 7,963,926 B2 | 6/2011 | Siejko et al. | |
| 7,996,058 B2 | 8/2011 | Ben-Haim et al. | |
| 8,060,214 B2 | 11/2011 | Larson et al. | |
| 8,126,561 B2 | 2/2012 | Chavan et al. | |
| 8,126,566 B2 | 2/2012 | Stahmann et al. | |
| 8,264,240 B2 | 9/2012 | Park et al. | |
| 8,271,093 B2 | 9/2012 | Von Arx et al. | |
| 8,277,441 B2 | 10/2012 | Porat et al. | |
| 8,301,262 B2 | 10/2012 | Mi et al. | |
| 8,340,776 B2 | 12/2012 | Doron et al. | |
| 8,340,778 B2 | 12/2012 | Tran et al. | |
| 8,374,693 B2 | 2/2013 | Chavan et al. | |
| 8,401,662 B2 | 3/2013 | Stahmann et al. | |
| 8,540,631 B2 | 9/2013 | Penner et al. | |
| 8,577,460 B2 | 11/2013 | Penner | |
| 8,594,802 B2 | 11/2013 | Stahmann et al. | |
| 8,626,295 B2 | 1/2014 | Doron et al. | |
| 8,647,328 B2 | 2/2014 | Porat et al. | |
| 8,660,648 B2 | 2/2014 | Chavan et al. | |
| 8,718,773 B2 | 5/2014 | Willis et al. | |
| 8,934,972 B2 | 1/2015 | Penner | |
| 9,451,932 B2 | 9/2016 | Zwirn | |
| 9,544,068 B2 | 1/2017 | Arbabian et al. | |
| 9,655,540 B2 | 5/2017 | Haefner | |
| 9,731,141 B2 | 8/2017 | Tran et al. | |
| 9,774,277 B2 | 9/2017 | Khuri-Yakub et al. | |
| 9,808,201 B2 | 11/2017 | Braido et al. | |
| 9,883,836 B2 | 2/2018 | Cahan et al. | |
| 10,003,862 B2 | 6/2018 | Rowland et al. | |
| 10,007,761 B2 | 6/2018 | Sadler et al. | |
| 10,014,570 B2 | 7/2018 | Arbabian et al. | |
| 10,076,303 B2 | 9/2018 | Medan et al. | |
| 10,080,903 B2 | 9/2018 | Willis et al. | |
| 10,118,054 B2 | 11/2018 | Maharbiz et al. | |
| 10,137,305 B2 | 11/2018 | Kane et al. | |
| 10,143,850 B2 | 12/2018 | Cowan et al. | |
| 10,177,606 B2 | 1/2019 | Charthad et al. | |
| 10,226,646 B2 | 3/2019 | Darlington et al. | |
| 10,252,066 B2 | 4/2019 | Radziemski et al. | |
| 10,300,309 B2 | 5/2019 | Maharbiz et al. | |
| 10,300,310 B2 | 5/2019 | Maharbiz et al. | |
| 10,426,962 B2 | 10/2019 | An et al. | |
| 10,430,624 B2 | 10/2019 | Sundaram et al. | |
| 10,456,588 B2 | 10/2019 | Willis et al. | |
| 10,576,305 B2 | 3/2020 | Maharbiz et al. | |
| 2001/0050087 A1 | 12/2001 | Weissman et al. | |
| 2002/0123672 A1 | 9/2002 | Christophersom et al. | |
| 2003/0013947 A1 | 1/2003 | Frattarola | |
| 2004/0162507 A1 | 8/2004 | Govari | |
| 2004/0176810 A1 | 9/2004 | Stadler et al. | |
| 2005/0037256 A1 | 2/2005 | Mukainakano | |
| 2005/0070799 A1 | 3/2005 | Vilkomerson et al. | |
| 2006/0122525 A1 | 6/2006 | Shusterman | |
| 2007/0088214 A1 | 4/2007 | Shuros et al. | |
| 2007/0170887 A1 | 7/2007 | Harguth et al. | |
| 2007/0208390 A1 | 9/2007 | Von Arx et al. | |
| 2008/0021289 A1 | 1/2008 | Zhang et al. | |
| 2008/0112885 A1 | 5/2008 | Okunev et al. | |
| 2009/0201148 A1* | 8/2009 | Tran | A61N 1/37217 381/337 |
| 2010/0022886 A1 | 1/2010 | Ayati et al. | |
| 2010/0114602 A1 | 5/2010 | Joao et al. | |
| 2010/0274302 A1 | 10/2010 | Armstrong et al. | |
| 2011/0009746 A1 | 1/2011 | Tran et al. | |
| 2012/0014367 A1* | 1/2012 | Caillerie | H04W 40/06 370/345 |
| 2012/0123284 A1 | 5/2012 | Kheradvar | |
| 2012/0315862 A1 | 12/2012 | Okano | |
| 2012/0327747 A1 | 12/2012 | Porat et al. | |
| 2013/0116575 A1 | 5/2013 | Mickle et al. | |
| 2013/0144379 A1 | 6/2013 | Najafi et al. | |
| 2014/0155748 A1 | 6/2014 | Pernisa et al. | |
| 2014/0306807 A1 | 10/2014 | Rowland et al. | |
| 2014/0330143 A1 | 11/2014 | Kroh | |
| 2015/0133796 A1 | 5/2015 | Yadav | |
| 2015/0305706 A1 | 10/2015 | Kanik et al. | |
| 2015/0374253 A1 | 12/2015 | Kim et al. | |
| 2016/0045316 A1 | 2/2016 | Braido et al. | |
| 2016/0058324 A1 | 3/2016 | Cao | |
| 2016/0066788 A1 | 3/2016 | Tran et al. | |
| 2016/0192907 A1 | 7/2016 | Zwirn | |
| 2016/0248276 A1 | 8/2016 | Hong et al. | |
| 2016/0287172 A1 | 10/2016 | Morris et al. | |
| 2017/0077736 A1* | 3/2017 | Leabman | G06V 30/224 |
| 2017/0157407 A1 | 6/2017 | Zellmer et al. | |
| 2017/0196509 A1 | 7/2017 | Hunter | |
| 2017/0201130 A1 | 7/2017 | Park | |
| 2017/0238833 A1 | 8/2017 | Felix et al. | |
| 2017/0258336 A1 | 9/2017 | Furness et al. | |
| 2017/0258585 A1 | 9/2017 | Marquez et al. | |
| 2018/0008228 A1 | 1/2018 | An et al. | |
| 2018/0042555 A1 | 2/2018 | Braido et al. | |
| 2018/0085605 A1* | 3/2018 | Maharbiz | B06B 1/06 |
| 2018/0106898 A1 | 4/2018 | Baskaran et al. | |
| 2018/0153506 A1 | 6/2018 | Rodriquez | |
| 2018/0178022 A1 | 6/2018 | Koop et al. | |
| 2018/0199883 A1 | 7/2018 | Banet et al. | |
| 2018/0226838 A1 | 8/2018 | Govindaraj | |
| 2018/0254669 A1 | 9/2018 | Rahman et al. | |
| 2018/0263511 A1 | 9/2018 | Burnes et al. | |
| 2018/0287431 A1 | 10/2018 | Liu | |
| 2019/0028301 A1* | 1/2019 | Forbes | H04L 12/4633 |

(56) References Cited

U.S. PATENT DOCUMENTS

| | | |
|---|---|---|
| 2019/0030375 A1 | 1/2019 | Zachar |
| 2019/0046074 A1 | 2/2019 | Sabharwal |
| 2019/0082978 A1 | 3/2019 | Van Der Horst et al. |
| 2019/0150881 A1 | 5/2019 | Maharbiz et al. |
| 2019/0150882 A1 | 5/2019 | Maharbiz et al. |
| 2019/0199139 A1 | 6/2019 | Perry |
| 2019/0201702 A1 | 7/2019 | Mi et al. |
| 2019/0321640 A1 | 10/2019 | Carmena et al. |
| 2020/0026892 A1 | 1/2020 | Sundaram et al. |
| 2022/0062650 A1 | 3/2022 | Maharbiz et al. |
| 2022/0131424 A1* | 4/2022 | Charthad ............ H04B 13/005 |
| 2022/0265157 A1 | 8/2022 | Charthad et al. |
| 2023/0158280 A1 | 5/2023 | Andriola et al. |
| 2023/0191094 A1 | 6/2023 | Fahey et al. |
| 2023/0200667 A1 | 6/2023 | Andriola et al. |
| 2023/0201546 A1 | 6/2023 | Fahey et al. |
| 2023/0210374 A1 | 7/2023 | Charthad et al. |
| 2023/0405290 A1 | 12/2023 | Andriola et al. |

FOREIGN PATENT DOCUMENTS

| | | |
|---|---|---|
| EP | 2 337 609 B1 | 8/2016 |
| EP | 3 439 145 A1 | 2/2019 |
| JP | 2010-094236 A | 4/2010 |
| JP | 2010-527699 A | 8/2010 |
| JP | 2010-539617 A | 12/2010 |
| JP | 2015-054007 A | 3/2015 |
| JP | 2016-501605 A | 1/2016 |
| JP | 2016-534703 A | 11/2016 |
| JP | 2017-520337 A | 7/2017 |
| JP | 2019-519321 A | 7/2019 |
| KR | 101185112 B1 | 9/2012 |
| WO | WO-97/29699 A1 | 8/1997 |
| WO | WO-01/36014 A2 | 5/2001 |
| WO | WO-2004/096022 A1 | 11/2004 |
| WO | WO-2006/010010 A1 | 1/2006 |
| WO | WO-2006/069327 A2 | 6/2006 |
| WO | WO-2007/072122 A1 | 6/2007 |
| WO | WO-2007/106490 A2 | 9/2007 |
| WO | WO-2007/127696 A2 | 11/2007 |
| WO | WO-2007/149936 A2 | 12/2007 |
| WO | WO-2008/011570 A1 | 1/2008 |
| WO | WO-2008/031095 A1 | 3/2008 |
| WO | WO-2008/156981 A2 | 12/2008 |
| WO | WO-2010/011612 A1 | 1/2010 |
| WO | WO-2010/149726 A2 | 12/2010 |
| WO | WO-2014/047528 A1 | 3/2014 |
| WO | WO-2014/164363 A1 | 10/2014 |
| WO | WO-2014/179739 A1 | 11/2014 |
| WO | WO-2016/028799 A1 | 2/2016 |
| WO | WO-2018/009377 A1 | 1/2018 |
| WO | WO-2018/009905 A2 | 1/2018 |
| WO | WO-2018/009908 A1 | 1/2018 |
| WO | WO-2018/009910 A1 | 1/2018 |
| WO | WO-2018/009911 A1 | 1/2018 |
| WO | WO-2018/104702 A1 | 6/2018 |
| WO | WO-2018/119434 A2 | 6/2018 |
| WO | WO-2018/140347 A1 | 8/2018 |
| WO | WO-2018/175939 A1 | 9/2018 |
| WO | WO-2018/191201 A1 | 10/2018 |
| WO | WO-2018/220143 A1 | 12/2018 |
| WO | WO-2019/008502 A1 | 1/2019 |
| WO | WO-2019/018644 A1 | 1/2019 |
| WO | WO-2019/032350 A1 | 2/2019 |
| WO | WO-2019/094231 A1 | 5/2019 |
| WO | WO-2019/136233 A1 | 7/2019 |
| WO | WO-2020/047152 A1 | 3/2020 |
| WO | WO-2021/007555 A1 | 1/2021 |
| WO | WO-2022/246283 A1 | 11/2022 |
| WO | WO-2022/266503 A2 | 12/2022 |
| WO | WO-2023/278612 A1 | 1/2023 |
| WO | WO-2023/278725 A1 | 1/2023 |
| WO | WO-2023/064479 A1 | 4/2023 |
| WO | WO-2023/122521 A1 | 6/2023 |

OTHER PUBLICATIONS

Cong, P. et al. (2009). "Wireless power recharging for implantable bladder pressure sensor," IEEE Sensors, Oct. 25-28, 2009, pp. 1670-1673.

Extended European Search Report mailed on Dec. 19, 2022, for EP Application No. 20 787 209.4, filed on Apr. 9, 2020, 8 pages.

Extended European Search Report mailed on Jun. 12, 2023, for EP Application No. 20 836 210.3, filed on Jul. 10, 2020, 8 pages.

Extended European Search Report mailed on May 29, 2024, for EP Application No. 21 822 303.0, filed on Jun. 7, 2021, 7 pages.

Final Office Action mailed on May 17, 2024, for U.S. Appl. No. 17/571,817, filed Jan. 10, 2022, 13 pages.

Final Office Action mailed on Nov. 13, 2024, for U.S. Appl. No. 17/496,216, filed Oct. 7, 2021, 13 pages.

International Search Report mailed on Aug. 28, 2020, for PCT Application No. PCT/US2020/027468, filed on Apr. 9, 2020, 4 pages.

International Search Report mailed on Dec. 8, 2020, for PCT Application No. PCT/US2020/041696, filed on Jul. 10, 2020, 4 pages.

International Search Report mailed on Nov. 17, 2021, for PCT Application No. PCT/US2021/036258, filed on Jun. 7, 2021, 4 pages.

International Search Report mailed on Dec. 12, 2022, for PCT Application No. PCT/US2022/035574, filed on Jun. 29, 2022, 7 pages.

International Search Report mailed on Jun. 24, 2024, for PCT Application No. PCT/US2023/085758, filed on Dec. 22, 2023, 6 pages.

Klein, L. (2024). "Pre-clinical results with a chronically-adjustable and pressure sensing interatrial shunt," THT 2024, Poster Abstract, 1 page.

Non-Final Office Action mailed on Oct. 17, 2023, for U.S. Appl. No. 17/571,817, filed Jan. 10, 2022, 11 pages.

Non-Final Office Action mailed on Jan. 31, 2024, for U.S. Appl. No. 17/496,216, filed Oct. 7, 2021, 12 pages.

Sorajja, P. (Oct. 2023). "Pre-clinical results with a chronically-adjustable and pressure sensing interatrial shunt (Adona Medical)," Euro PCR 2024, Presentation, 14 pages.

Written Opinion of the International Searching Authority mailed on Aug. 28, 2020, for PCT Application No. PCT/US2020/027468, filed on Apr. 9, 2020, 10 pages.

Written Opinion of the International Searching Authority mailed on Dec. 8, 2020, for PCT Application No. PCT/US2020/041696, filed on Jul. 10, 2020, 6 pages.

Written Opinion of the International Searching Authority mailed on Nov. 17, 2021, for PCT Application No. PCT/US2021/036258, filed on Jun. 7, 2021, 7 pages.

Written Opinion of the International Searching Authority mailed on Dec. 12, 2022, for PCT Application No. PCT/US2022/035574, filed on Jun. 29, 2022, 14 pages.

Written Opinion of the International Searching Authority mailed on Jun. 24, 2024, for PCT Application No. PCT/US2023/085758, filed on Dec. 22, 2023, 12 pages.

* cited by examiner

SYSTEMS, DEVICES, AND METHODS FOR ESTABLISHING A WIRELESS LINK IN A HETEROGENEOUS MEDIUM

CROSS-REFERENCE TO RELATED APPLICATIONS

This application is a continuation of International Application No. PCT/US2022/035574, filed Jun. 29, 2022, which claims priority to U.S. Provisional Application No. 63/216,282, filed on Jun. 29, 2021, the contents of each of which are incorporated herein by reference in their entireties.

TECHNICAL FIELD

Devices, systems, and methods herein relate to establishing a wireless link between two or more wireless devices of a wireless system.

BACKGROUND

A wireless system may comprise a wireless link between two or more wireless devices of the wireless system. Such a wireless link may be used for one or more of wireless power transfer, wireless data communication, transferring wireless commands, transferring wireless signals, combinations thereof, and the like. For example, wireless implantable devices may be wirelessly powered by, and may wirelessly communicate with, an external wireless device. Presence of heterogeneous media in the wireless link, such as different tissue structures in body, and/or relative motion between the wireless devices, may limit the reliability and/or efficiency of the wireless link. As such, additional devices, systems, and methods may be desirable for establishing a reliable and/or efficient wireless link between two or more wireless devices of a wireless system.

SUMMARY

Described herein are systems, devices and methods for exchanging wireless signals between wireless devices of a wireless system. Generally, a system may be configured to exchange one or more of wireless power, wireless data, and wireless commands between wireless devices based on one or more of a feedback signal, a link scan signal and a data signal. In some variations, systems, devices and methods described herein may allow mitigation of multipath interference in a heterogeneous tissue medium for efficient and/or reliable exchange of wireless signals (e.g., power, data, commands) between a wireless implantable device and an external wireless device. In some variations, a system configured to exchange wireless power or data, may comprise a first device configured to transmit a feedback signal with a first duration, and a second device comprising a transducer array and a processor, wherein the transducer array may be configured to receive the feedback signal on one or more transducer elements of the transducer array for a second duration, the processor may be configured to process the feedback signal received in the second duration by one or more transducer elements of the transducer array to generate feedback signal data, and determine a transducer array configuration based at least in part on the feedback signal data, and the second device may be configured to exchange one or more wireless signals with the first device using the transducer array configuration.

In some variations, the second duration may be greater than the first duration. In some variations, the processor may be further configured to detect an onset of the received feedback signal on one or more transducer elements of the transducer array using one or more of envelope detection, predetermined timing, coherent detection, and comparison of the received feedback signal amplitude to a predetermined threshold level.

In some variations, the feedback signal data may comprise one or more of an absolute amplitude or magnitude, a relative amplitude or magnitude, an absolute signal strength, a relative signal strength, signal energy in one or more frequency bands, an apodization, an absolute phase, a relative phase, an absolute time delay, a relative time delay, an absolute time of arrival, a relative time of arrival, a frequency, a time duration, number of cycles, an absolute signal-to-noise ratio, and a relative signal-to-noise ratio of the feedback signal received within the second duration by one or more transducer elements of the transducer array. In some variations, the transducer array configuration may comprise one or more of a selected set of transducer elements, apodizations, signal strengths, voltage levels, current levels, pulse widths, pulse width modulations, duty cycles, phases, time delays, frequencies and transmit durations applied to one or more transducer elements of the transducer array for transmitting wireless signals to the first device.

In some variations, the phases applied to the one or more transducer elements of the transducer array for transmitting wireless signals to the first device may be based on one or more of the relative phases of the received feedback signal in the second duration at a predetermined frequency and the time of arrival of the feedback signal received on the one or more transducer elements. In some variations, the time delays applied to the one or more transducer elements of the transducer array for transmitting wireless signals to the first device may be based on one or more of the relative phases of the received feedback signal in the second duration at a predetermined frequency and the time of arrival of the feedback signal received on the one or more transducer elements.

In some variations, the received feedback signal may comprise a time duration and a settled amplitude. In some variations, the feedback signal may comprise one or more of an impulse signal and a pulse signal. In some variations, the processor may be configured to process the feedback signal or determine the transducer array configuration using one or more of a time domain analysis, a frequency domain analysis, and an interpolation analysis. In some variations, the time domain analysis may comprise one or more of cross-correlation and time reversal. In some variations, the frequency domain analysis may comprise computing one or more of a Fourier transform, a discrete Fourier transform (DFT) and a discrete-time Fourier transform (DTFT) at one or more predetermined frequencies. In some variations, the processor may be configured to use a fast Fourier transform (FFT) algorithm for computing one or more of the Fourier transform, the discrete Fourier transform (DFT) and the discrete-time Fourier transform (DTFT) at the one or more predetermined frequencies. In some variations, the one or more predetermined frequencies may be based on one or more feedback signal frequencies. In some variations, the processor may be configured to determine the one or more predetermined frequencies based on one or more of a time domain analysis and a frequency domain analysis of the feedback signal received in one or more of the first duration, the second duration and a third duration by one or more transducer elements of the transducer array.

In some variations, the processor may be configured to use at least one of the feedback signal data and a predetermined power of the transmitted feedback signal to determine one or more of a link efficiency and transmit power for transmitting wireless signals to the first device. In some variations, the one or more wireless signals exchanged with the first device may comprise a first set of frequencies and the feedback signal may comprise a second set of frequencies, the first set of frequencies different from the second set of frequencies.

In some variations, a first set of transducer elements configured to receive the feedback signal may comprise one or more common transducer elements with a second set of transducer elements corresponding to the transducer array configuration configured to exchange wireless signals with the first device. In some variations, a first set of transducer elements configured to receive the feedback signal may comprise different transducer elements than a second set of transducer elements corresponding to the transducer array configuration configured to exchange wireless signals with the first device.

In some variations, the first device may comprise an implantable medical device, and the second device may comprise an external wireless device configured to be disposed physically separate from the first device. In some variations, the first device may comprise an external wireless device, and the second device may comprise an implantable medical device configured to be disposed physically separate from the first device.

In some variations, the first device may be configured to transmit the feedback signal at one or more predetermined repetition intervals. In some variations, the second device may be further configured to transmit a wireless command to the first device, and the first device may be configured to transmit the feedback signal in response to receiving the wireless command. In some variations, the transmitted feedback signal may comprise a reflection signal or a backscatter signal in response to receiving a wireless signal transmitted by the second device to the first device. In some variations, the transmitted feedback signal may comprise one or more of an ultrasonic signal, an acoustic signal, a vibrational signal, a radio-frequency signal, an electromagnetic signal, a magnetic signal, an electric signal, and an optical signal.

In some variations, the first device may be further configured to transmit one or more data signals to the second device. In some variations, the processor may be further configured to select one or more transducer elements of the transducer array of the second device for processing the one or more data signals. In some variations, the processor may be configured to select the one or more transducer elements of the transducer array of the second device based on one or more of a signal strength of the received feedback signal, a signal-to-noise ratio of the received feedback signal, an energy of the received feedback signal in one or more frequency bands, an apodization of the transducer element, a moving mean of the feedback signal amplitude, a signal strength of an interferer, a signal strength of multipath interference, and a multipath time.

Also described are methods of exchanging wireless signals in a wireless system. In some variations, a method may comprise the steps of transmitting a feedback signal with a first duration from a first device of the wireless system to a second device of the wireless system, receiving the feedback signal for a second duration using one or more transducer elements of a transducer array of the second device, processing the feedback signal received in the second duration using one or more transducer elements of the transducer array to generate feedback signal data using a processor of the second device, determining a transducer array configuration of the second device based at least in part on the feedback signal data using the processor of the second device, and exchanging one or more wireless signals with the first device using the transducer array configuration of the second device.

In some variations, the second duration may be greater than the first duration. In some variations, the method may comprise the step of detecting an onset of the received feedback signal on one or more transducer elements of the transducer array using one or more of envelope detection, predetermined timing, coherent detection, and comparison of the received feedback signal amplitude to a predetermined threshold level.

In some variations, the feedback signal data may comprise one or more of an absolute amplitude or magnitude, a relative amplitude or magnitude, an absolute signal strength, a relative signal strength, signal energy in one or more frequency bands, an apodization, an absolute phase, a relative phase, an absolute time delay, a relative time delay, an absolute time of arrival, a relative time of arrival, a frequency, a time duration, number of cycles, an absolute signal-to-noise ratio, and a relative signal-to-noise ratio of the feedback signal received within the second duration by one or more transducer elements of the transducer array. In some variations, the transducer array configuration may comprise one or more of a selection of a set of transducer elements, an apodization, a signal strength, a voltage level, a current level, a pulse width, pulse width modulation, a duty cycle of a signal, a phase, a time delay, a frequency and a transmit duration applied to one or more transducer elements of the transducer array for transmitting wireless signals to the first device.

In some variations, the phases applied to the one or more transducer elements of the transducer array for transmitting wireless signals to the first device may be based on one or more of the relative phases of the received feedback signal in the second duration at a predetermined frequency and the time of arrival of the feedback signal received using the one or more transducer elements. In some variations, the time delays applied to the one or more transducer elements of the transducer array for transmitting wireless signals to the first device may be based on one or more of the relative phases of the received feedback signal in the second duration at a predetermined frequency and the time of arrival of the feedback signal received using the one or more transducer elements.

In some variations, the received feedback signal may comprise a time duration and a settled amplitude. In some variations, the feedback signal may comprise one or more of an impulse signal and a pulse signal. In some variations, processing the feedback signal or determining the transducer array configuration of the second device may comprise one or more of a time domain analysis, a frequency domain analysis, and an interpolation analysis. In some variations, the time domain analysis may comprise one or more of cross-correlation and time reversal. In some variations, the frequency domain analysis may comprise computing one or more of a Fourier transform, a discrete Fourier transform (DFT) and a discrete-time Fourier transform (DTFT) at one or more predetermined frequencies. In some variations, computing one or more of the Fourier transform, the discrete Fourier transform (DFT) and the discrete-time Fourier transform (DTFT) at the one or more predetermined frequencies may comprise using a fast Fourier transform (FFT) algorithm. In some variations, the one or more predetermined frequencies may be based on one or more feedback signal frequencies. In some variations, the method may comprise the step of determining the one or more predetermined frequencies based on one or more of a time domain analysis and a frequency domain analysis of the feedback signal received in one or more of the first duration, the second duration and a third duration using one or more transducer elements of the transducer array.

In some variations, determining a transducer array configuration of the second device may comprise using at least one of the feedback signal data and a predetermined power of the transmitted feedback signal to determine one or more of a link efficiency and a transmit power for transmitting wireless signals to the first device. In some variations, the one or more wireless signals exchanged with the first device may comprise a first set of frequencies and the feedback signal may comprise a second set of frequencies, wherein the first set of frequencies may be different from the second set of frequencies.

In some variations, a first set of transducer elements configured to receive the feedback signal may comprise one or more common transducer elements with a second set of transducer elements corresponding to the transducer array configuration configured to exchange wireless signals with the first device. In some variations, a first set of transducer elements configured to receive the feedback signal may comprise different transducer elements than a second set of transducer elements corresponding to the transducer array configuration configured to exchange wireless signals with the first device.

In some variations, the first device may comprise an implantable medical device, and the second device may comprise an external wireless device configured to be disposed physically separate from the first device. In some variations, the first device may comprise an external wireless device, and the second device may comprise an implantable medical device configured to be disposed physically separate from the first device.

In some variations, the method may further comprise the step of transmitting the feedback signal from the first device at one or more predetermined repetition intervals. In some variations, the method may further comprise transmitting a wireless command from the second device to the first device, and transmitting the feedback signal from the first device to the second device in response to receiving the wireless command. In some variations, the transmitted feedback signal may comprise a reflection signal or a backscatter signal in response to receiving a wireless signal transmitted by the second device to the first device. In some variations, the transmitted feedback signal may comprise one or more of an ultrasonic signal, an acoustic signal, a vibrational signal, a radio-frequency signal, an electromagnetic signal, a magnetic signal, an electric signal, and an optical signal.

In some variations, the method may further comprise the step of transmitting one or more data signals from the first device to the second device. In some variations, the method may comprise the step of selecting one or more transducer elements of the transducer array of the second device for processing the one or more data signals using the processor of the second device. In some variations, selecting the one or more transducer elements of the transducer array of the second device may be based on one or more of a signal strength of the received feedback signal, a signal-to-noise ratio of the received feedback signal, an energy of the received feedback signal in one or more frequency bands, an apodization of the transducer element, a moving mean of the feedback signal amplitude, a signal strength of an interferer, a signal strength of multipath interference, and a multipath time.

Also described are systems configured for wireless data communication. In some variations, a system may comprise a first device configured to transmit a link scan signal and a first data signal, and a second device comprising one or more transducer elements, and a processor, wherein the one or more transducer elements may be configured to receive the link scan signal and the first data signal from the first device, and the processor may be configured to process the received link scan signal and the received first data signal to generate a second data signal, and decode the first data signal based at least in part on the second data signal.

In some variations, the link scan signal may comprise one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals and a plurality of pulse signals. In some variations, the pulse signal or the feedback signal may comprise one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal. In some variations, the first data signal may comprise one or more of on-off keying (OOK) modulation, amplitude-shift keying (ASK) modulation, pulse-position modulation (PPM), frequency-shift keying (FSK) modulation, phase-shift keying (PSK) modulation, and quadrature amplitude modulation (QAM).

In some variations, the processor may be further configured to select one or more time durations of one or more of the received link scan signal and the received first data signal based on one or more of a predetermined timing, signal onset detection, detection of one or more of a signal rising edge and a signal falling edge, detection of one or more of a header component and a footer component of a signal, a multipath time and a drift in a frequency of one or more of the received link scan signal and the received first data signal.

In some variations, the processor may be configured to process the received link scan signal to determine a scaled impulse response of the wireless system. In some variations, the link scan signal may comprise a feedback signal and the processor may be configured to determine a scaled impulse response of the wireless system by deconvolving the scaled received feedback signal with a scaled reference feedback signal using one or more of frequency domain computation and time domain computation. In some variations, one or more of the scaled impulse response, the scaled received feedback signal, and the scaled reference feedback signal may be scaled by one or more of an amplitude in the time domain, an amplitude at a frequency, an energy in one or more frequency bands, a signal-to-noise ratio for one or more of the impulse response, the received feedback signal, and the reference feedback signal, an apodization of the corresponding transducer element, a predetermined scaling factor, and a normalization scaling factor.

In some variations, the second device may comprise a memory preloaded with one or more of a frequency domain representation and a time domain representation of the scaled reference feedback signal. In some variations, the processor may be further configured to generate one or more of a frequency domain representation and a time domain representation of the scaled reference feedback signal based on one or more properties of one or more of the received link scan signal and the received first data signal. In some variations, the one or more properties of one or more of the received link scan signal and the received first data signal may comprise one or more of a frequency, a duration, a number of cycles, an amplitude, a phase, and a time of arrival.

In some variations, the processor may be configured to process the received link scan signal and the received first data signal by deconvolving a scaled received first data signal with one or more of the scaled impulse response and a scaled received link scan signal, using one or more of a frequency domain analysis and a time domain analysis, to generate the second data signal. In some variations, one or more of the scaled received first data signal, the scaled impulse response and the scaled received link scan signal may be scaled by an amplitude in the time domain, an amplitude at a frequency, an energy in one or more frequency bands, a signal-to-noise ratio for one or more of the received first data signal, the impulse response, and the received link scan signal, an apodization of the corresponding transducer element, a predetermined scaling factor, and a normalization scaling factor.

In some variations, the processor may be configured to process the received link scan signal and the received first data signal by deconvolving a scaled received first data signal with a scaled received link scan signal using one or more of a frequency domain analysis and a time domain analysis, to generate the second data signal. In some variations, the link scan signal may comprise one or more of an impulse signal, a feedback signal, a pulse signal, a pulse signal representing a single data bit of the first data signal, a pulse signal representing a plurality of data bits of the first data signal, a plurality of impulse signals and a plurality of pulse signals.

In some variations, the processor may be further configured to filter one or more of the link scan signal, the first data signal and the second data signal using one or more of a band-pass filter, a low-pass filter, a high-pass filter, an all-pass filter, a notch filter and a band-reject filter.

In some variations, the processor may be further configured to select two or more second data signals for signal combining based on one or more of a header check, a footer check, relative strengths of the two or more second data signals, relative signal-to-noise ratios of the two or more second data signals, relative signal-to-interference ratios of the two or more second data signals, relative strengths of residual interference present in the two or more second data signals, and cross-correlation values of the two or more second data signals to a reference second data signal. In some variations, the processor may be further configured to determine the reference second data signal based on one or more of the second data signal's amplitude, energy, signal-to-noise ratio or signal-to-interference ratio, the corresponding first data signal's amplitude, energy, signal-to-noise ratio or signal-to-interference ratio, the corresponding link scan signal's amplitude, energy, signal-to-noise ratio or signal-to-interference ratio, and an apodization of the corresponding transducer element on which the link scan signal or the first data signal may be received.

In some variations, the processor may be further configured to combine two or more scaled second data signals using one or more of summing, delaying and summing, averaging, and delaying and averaging to generate one or more combined data signals. In some variations, the scaled second data signal may be scaled by one or more of an amplitude in the time domain, an amplitude at a frequency, an energy in one or more frequency bands, a signal-to-noise ratio of the second data signal, an apodization of the corresponding transducer element, a predetermined scaling factor, and a normalization scaling factor.

In some variations, the processor may be further configured to select a combined data signal for decoding data bits based on one or more of the combined data signal's amplitude in time domain, the combined data signal's amplitude at a frequency, the combined data signal's energy in one or more frequency bands, and the combined data signal's signal-to-noise ratio. In some variations, the processor may be further configured to decode data bits based at least upon one or more combined data signals using one or more of OOK demodulation, ASK demodulation, PPM demodulation, FSK demodulation, PSK demodulation, QAM demodulation, envelope detection, matched filtering, comparison of the amplitude of the one or more combined data signals to a predetermined threshold, and sampling the amplitude of the one or more combined data signals at fixed time offsets.

In some variations, the processor may be further configured to decode data bits corresponding to one or more second data signals using one or more of OOK demodulation, ASK demodulation, PPM demodulation, FSK demodulation, PSK demodulation, QAM demodulation, envelope detection, matched filtering, comparison of the amplitude of the one or more second data signals to a predetermined threshold, and sampling the amplitude of the one or more second data signals at fixed time offsets. In some variations, the processor may be further configured to select one or more second data signals prior to decoding data bits based on a header check, a footer check, relative strengths of the one or more second data signals, relative signal-to-noise ratios of the one or more second data signals, relative strengths of residual interference present in the one or more second data signals, and cross-correlation values of the one or more second data signals to a reference second data signal.

In some variations, the processor may be further configured to determine one or more of a majority occurrence of a bit value, a weighted majority occurrence of a bit value, a mean bit value, and a weighted mean bit value among the decoded data bit values corresponding to two or more second data signals. In some variations, the processor may be configured to determine the weighted majority occurrence or the weighted mean bit value by scaling the bit value by one or more of an apodization of the transducer element on which the corresponding link scan signal or the corresponding first data signal may be received, an amplitude, an energy, a signal-to-noise ratio, a time delay, a phase and a multipath time of one or more of the second data signal, the corresponding first data signal and the corresponding link scan signal.

In some variations, the first device may comprise an implantable medical device, the second device may comprise an external wireless device configured to be disposed physically separate from the first device, and the first data signal may comprise an uplink data signal. In some variations, the first device may comprise an external wireless device, the second device may comprise an implantable medical device configured to be disposed physically separate from the first device, and the first data signal may comprise a downlink data signal.

In some variations, the first device may be configured to transmit one or more of the link scan signal and the first data signal at one or more predetermined repetition intervals. In some variations, the second device may be further configured to transmit a wireless command to the first device, and the first device may be configured to transmit the link scan signal and the first data signal in response to receiving the wireless command. In some variations, one or more of the transmitted link scan signal and the transmitted first data signal may comprise one or more of a reflection signal and a backscatter signal in response to receiving a wireless signal transmitted by the second device to the first device. In some variations, one or more of the transmitted link scan signal and the transmitted first data signal may comprise one or more of an ultrasonic signal, an acoustic signal, a vibrational signal, a radio-frequency signal, an electromagnetic signal, a magnetic signal, an electric signal, and an optical signal.

Also described are methods of decoding data signals in a wireless system. In some variations, a method may comprise the steps of transmitting a link scan signal and a first data signal from a first device of the wireless system to a second device of the wireless system, receiving the link scan signal and the first data signal using one or more transducer elements of the second device, processing the received link scan signal and the received first data signal using a processor of the second device to generate a second data signal, and decoding the first data signal based at least in part on the second data signal.

In some variations, the link scan signal may comprise one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals, and a plurality of pulse signals. In some variations, the pulse signal or the feedback signal may comprise one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal. In some variations, the first data signal may comprise one or more of on-off keying (OOK) modulation, amplitude-shift keying (ASK) modulation, pulse-position modulation (PPM), frequency-shift keying (FSK) modulation, phase-shift keying (PSK) modulation, and quadrature amplitude modulation (QAM).

In some variations, the method may comprise the step of selecting one or more time durations of one or more of the received link scan signal and the received first data signal prior to processing based on one or more of a predetermined timing, signal onset detection, detection of one or more of a signal rising edge and a signal falling edge, detection of one or more of a header component and a footer component of a signal, a multipath time and a drift in a frequency of one or more of the received link scan signal and the received first data signal.

In some variations, processing the received link scan signal may comprise determining a scaled impulse response of the wireless system. In some variations, the link scan signal may comprise a feedback signal and determining the scaled impulse response of the wireless system may comprise deconvolving a scaled received feedback signal with a scaled reference feedback signal using one or more of a frequency domain analysis and a time domain analysis. In some variations, one or more of the scaled impulse response, the scaled received feedback signal, and the scaled reference feedback signal may be scaled by one or more of an amplitude in the time domain, an amplitude at a frequency, an energy in one or more frequency bands, a signal-to-noise ratio for one or more of the impulse response, the received feedback signal, and the reference feedback signal, an apodization of the corresponding transducer element, a predetermined scaling factor, and a normalization scaling factor.

In some variations, the method may comprise the step of storing one or more of a frequency domain representation and a time domain representation of the scaled reference feedback signal into a memory of the second device. In some variations, the method may comprise the step of generating one or more of a frequency domain representation and a time domain representation of the scaled reference feedback signal based on one or more properties of one or more of the received link scan signal and the received first data signal. In some variations, the one or more properties of one or more of the received link scan signal and the received first data signal may comprise one or more of a frequency, a duration, a number of cycles, an amplitude, a phase, and a time of arrival.

In some variations, processing the received link scan signal and the received first data signal may comprise deconvolving a scaled received first data signal with one or more of the scaled impulse response and a scaled received link scan signal, using one or more of a frequency domain analysis and a time domain analysis, to generate the second data signal. In some variations, one or more of the scaled received first data signal, the scaled impulse response and the scaled received link scan signal may be scaled by an amplitude in the time domain, an amplitude at a frequency, an energy in one or more frequency bands, a signal-to-noise ratio for one or more of the received first data signal, the impulse response, and the received link scan signal, an apodization of the corresponding transducer element, a predetermined scaling factor, and a normalization scaling factor.

In some variations, processing the received link scan signal and the received first data signal may comprise deconvolving a scaled received first data signal with a scaled received link scan signal using one or more of a frequency domain analysis and a time domain analysis, to generate the second data signal. In some variations, the link scan signal may comprise one or more of an impulse signal, a feedback signal, a pulse signal, a pulse signal representing a single data bit of the first data signal, a pulse signal representing a plurality of data bits of the first data signal, a plurality of impulse signals and a plurality of pulse signals. In some variations, the method may comprise the step of filtering one or more of the link scan signal, the first data signal and the second data signal using one or more of a band-pass filter, a low-pass filter, a high-pass filter, an all-pass filter, a notch filter and a band-reject filter.

In some variations, the method may comprise the step of selecting two or more second data signals for signal combining based on one or more of a header check, a footer check, relative strengths of the two or more second data signals, relative signal-to-noise ratios of the two or more second data signals, relative signal-to-interference ratios of the two or more second data signals, relative strengths of residual interference present in the two or more second data signals, and cross-correlation values of the two or more second data signals to a reference second data signal. In some variations, the reference second data signal may be determined based on one or more of the second data signal's amplitude, energy, signal-to-noise ratio or signal-to-interference ratio, the corresponding first data signal's amplitude, energy, signal-to-noise ratio or signal-to-interference ratio, the corresponding link scan signal's amplitude, energy, signal-to-noise ratio or signal-to-interference ratio, and an apodization of the corresponding transducer element on which the link scan signal or the first data signal may be received.

In some variations, the method may comprise the step of combining two or more scaled second data signals using one or more of summing, delaying and summing, averaging, and delaying and averaging to generate one or more combined data signals. In some variations, the scaled second data signal may be scaled by one or more of an amplitude in the time domain, an amplitude at a frequency, an energy in one or more frequency bands, a signal-to-noise ratio of the second data signal, an apodization of the corresponding transducer element, a predetermined scaling factor, and a normalization scaling factor. In some variations, the method may comprise the step of selecting a combined data signal for decoding data bits based on one or more of the combined data signal's amplitude in time domain, the combined data signal's amplitude at a frequency, the combined data signal's energy in one or more frequency bands, and the combined data signal's signal-to-noise ratio. In some variations, the method may comprise the step of decoding data bits based at least upon one or more combined data signals using one or more of OOK demodulation, ASK demodulation, PPM demodulation, FSK demodulation, PSK demodulation, QAM demodulation, envelope detection, matched filtering, comparison of the amplitude of the one or more combined data signals to a predetermined threshold, and sampling the amplitude of the one or more combined data signals at fixed time offsets.

In some variations, the method may comprise the step of decoding data bits corresponding to one or more second data signals using one or more of OOK demodulation, ASK demodulation, PPM demodulation, FSK demodulation, PSK demodulation, QAM demodulation, envelope detection, matched filtering, comparison of the amplitude of the one or more second data signals to a predetermined threshold, and sampling the amplitude of the one or more second data signals at fixed time offsets. In some variations, the method may comprise the step of selecting one or more second data signals prior to decoding data bits based on a header check, a footer check, relative strengths of the one or more second data signals, relative signal-to-noise ratios of the one or more second data signals, relative strengths of residual interference present in the one or more second data signals, and cross-correlation values of the one or more second data signals to a reference second data signal.

In some variations, the method may comprise the step of determining one or more of a majority occurrence for a bit value, a weighted majority occurrence for a bit value, a mean bit value, and a weighted mean bit value among the decoded data bit values corresponding to two or more second data signals. In some variations, determining the weighted majority occurrence or weighted mean bit value may comprise scaling the bit value by one or more of an apodization of the transducer element on which the corresponding link scan signal or the corresponding first data signal may be received, an amplitude, an energy, a signal-to-noise ratio, a time delay, a phase and a multipath time of one or more of the second data signal, the corresponding first data signal and the corresponding link scan signal.

In some variations, the first device may comprise an implantable medical device, the second device may comprise an external wireless device configured to be disposed physically separate from the first device, and the first data signal may comprise an uplink data signal. In some variations, the first device may comprise an external wireless device, the second device may comprise an implantable medical device configured to be disposed physically separate from the first device, and the first data signal may comprise a downlink data signal.

In some variations, the method may comprise the step of transmitting one or more of the link scan signal and the first data signal at one or more predetermined repetition intervals. In some variations, the method may comprise the step of transmitting a wireless command from the second device to the first device, and transmitting the link scan signal and the first data signal from the first device to the second device in response to receiving the wireless command by the first device. In some variations, one or more of the transmitted link scan signal and the transmitted first data signal may comprise one or more of a reflection signal and a backscatter signal in response to receiving a wireless signal transmitted by the second device to the first device. In some variations, one or more of the transmitted link scan signal and the transmitted first data signal may comprise one or more of an ultrasonic signal, an acoustic signal, a vibrational signal, a radio-frequency signal, an electromagnetic signal, a magnetic signal, an electric signal, and an optical signal.

Also described are systems configured for wireless data communication. In some variations, a system may comprise a first device configured to transmit a link scan signal and a first data signal, and a second device comprising one or more transducer elements, and a processor, wherein the one or more transducer elements may be configured to receive the link scan signal and the first data signal from the first device, and the processor may be configured to process one or more of the received link scan signal and the received first data signal to select one or more transducer elements of the second device, and decode the first data signal based at least in part on the selected one or more transducer elements of the second device.

In some variations, the link scan signal may comprise one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals and a plurality of pulse signals. In some variations, the processor may be configured to select the one or more transducer elements of the second device based on one or more of a header check, a footer check, a bit error rate, relative strengths of the link scan signals, relative signal-to-noise ratios of the link scan signals, relative signal-to-interference ratios of the link scan signals, energy of the link scan signals in one or more frequency bands, a moving mean of the link scan signal amplitude, relative strengths of the first data signals, relative signal-to-noise ratios of the first data signals, relative signal-to-interference ratios of the first data signals, energy of the first data signals in one or more frequency bands, a moving mean of the first data signal amplitude, a signal strength of an interferer, a signal strength of multipath interference, a multipath time, and apodization of the one or more transducer elements.

Also described are methods of decoding data signals in a wireless system. In some variations, a method may comprise the steps of transmitting a link scan signal and a first data signal from a first device of the wireless system to a second device of the wireless system, receiving the link scan signal and the first data signal using one or more transducer elements of the second device, processing one or more of the received link scan signal and the received first data signal using a processor of the second device to select one or more transducer elements of the second device, and decoding the first data signal based at least in part on the selected one or more transducer elements of the second device.

In some variations, the link scan signal may comprise one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals and a plurality of pulse signals. In some variations, selecting the one or more transducer elements of the second device may be based on one or more of a header check, a footer check, a bit error rate, relative strengths of the link scan signals, relative signal-to-noise ratios of the link scan signals, relative signal-to-interference ratios of the link scan signals, energy of the link scan signals in one or more frequency bands, a moving mean of the link scan signal amplitude, relative strengths of the first data signals, relative signal-to-noise ratios of the first data signals, relative signal-to-interference ratios of the first data signals, energy of the first data signals in one or more frequency bands, a moving mean of the first data signal amplitude, a signal strength of an interferer, a signal strength of multipath interference, a multipath time, and apodization of the one or more transducer elements.

Also described are systems configured to exchange one or more of wireless power and data. In some variations, a system may comprise a first device configured to transmit a feedback signal, and a second device comprising a first transducer array, a second transducer array, and a processor, wherein the first transducer array may be configured to receive the feedback signal from the first device, the processor may be configured to extract one or more portions of the received feedback signals received by one or more transducer elements of the first transducer array, process the extracted one or more portions of the received feedback signals to generate feedback signal data, and determine a second transducer array configuration based at least in part on the feedback signal data, and the second transducer array configuration may be configured to exchange one or more wireless signals with the first device. In some variations, the extracted one or more portions of the received feedback signal may have a duration less than a duration of the received feedback signal. In some variations, the duration of the feedback signal may be greater than about 5 cycles of a carrier frequency of the feedback signal.

In some variations, the feedback signal data may comprise one or more of an absolute amplitude, a relative amplitude, an absolute signal strength, a relative signal strength, an absolute phase, a relative phase, an absolute time delay and a relative time delay of the feedback signals received by one or more transducer elements of the first transducer array of the second device.

In some variations, the first device may comprise an implantable medical device and the second device may comprise an external wireless device configured to be disposed physically separate from the first device. In some variations, the first transducer array and the second transducer array ay comprise one or more common transducer elements. In some variations, the first transducer array may comprise a subset of the second transducer array. In some variations, the first transducer array and the second transducer array may comprise distinct transducer elements. In some variations, the first transducer array and the second transducer array may each comprise an acoustic transducer array. In some variations, the acoustic transducer array may comprise an ultrasonic transducer array.

Also described are methods of exchanging wireless signals in a wireless system. In some variations, a method may comprise the steps of transmitting a feedback signal from a first device of the wireless system to a second device of the wireless system, receiving the feedback signal using a first transducer array of the second device, extracting one or more portions of the received feedback signals, received by one or more transducer elements of the first transducer array of the second device, using a processor of the second device, processing the extracted one or more portions of the received feedback signals using the processor of the second device to generate feedback signal data, determining a second transducer array configuration of the second device based at least in part on the feedback signal data, and exchanging one or more wireless signals with the first device using the second transducer array configuration of the second device. In some variations, the extracted one or more portions of the received feedback signal may have a duration less than a duration of the received feedback signal. In some variations, extracting one or more portions of the received feedback signal may comprise finding one or more regions of the received feedback signal waveform with a settled amplitude. In some variations, the duration of the transmitted feedback signal may be greater than about 5 cycles of a carrier frequency of the feedback signal.

In some variations, the method may comprise the step of detecting one or more of a rising edge and a falling edge of the received feedback signal prior to extracting one or more portions of the received feedback signal. In some variations, extracting one or more portions of the received feedback signal may be performed for the feedback signals received by a subset of the elements of the first transducer array. In some variations, the method may comprise the step of digitizing the feedback signal received by one or more transducer elements of the first transducer array prior to extracting one or more portions of the received feedback signal. In some variations, the method may comprise the step of detecting a rising edge of the received feedback signal using analog signal processing prior to digitizing the feedback signal received by one or more transducer elements of the first transducer array. In some variations, extracting one or more portions of the received feedback signal may be performed using one or more of digital signal processing and analog signal processing.

In some variations, the feedback signal data may comprise one or more of an absolute amplitude, a relative amplitude, an absolute signal strength, a relative signal strength, an absolute phase, a relative phase, an absolute time delay and a relative time delay of the feedback signals received by one or more transducer elements of the first transducer array of the second device. In some variations, determining the second transducer array configuration of the second device may comprise determining one or more of an amplitude, a signal strength, a phase and a time delay for transmitting wireless signals through one or more transducer elements of the second transducer array.

In some variations determining the one or more of the amplitude, the signal strength, the phase and the time delay for transmitting wireless signals through one or more transducer elements of the second transducer array may comprise performing one or more of cross-correlation and time reversal. In some variations, determining the one or more of the amplitude, the signal strength, the phase and the time delay for transmitting wireless signals through one or more transducer elements of the second transducer array may further comprise interpolation of one or more of the amplitudes, the signal strengths, the phases and the delays based on the relative spatial positions of the transducer elements of the first transducer array and the second transducer array. In some variations, determining the second transducer array configuration may comprise a method of closed-loop powering.

In some variations, the first device may comprise an implantable medical device and the second device may comprise an external wireless device configured to be disposed physically separate from the first device. In some variations, the first transducer array and the second transducer array comprise one or more common transducer elements. In some variations, the first transducer array may comprise a subset of the second transducer array. In some variations, the first transducer array and the second transducer array may comprise distinct transducer elements. In some variations, the first transducer array and the second transducer array may each comprise an acoustic transducer array. In some variations, the acoustic transducer array may comprise an ultrasonic transducer array.

Also described are systems configured to exchange one or more of power and data. In some variations, a system may comprise a first device configured to transmit a link scan signal, and a second device comprising a first transducer array, a second transducer array, and a processor, wherein the first transducer array may be configured to receive the link scan signal from the first device, the processor may be configured to process the received link scan signals received by one or more transducer elements of the first transducer array of the second device to generate link scan signal data, and determine a second transducer array configuration based at least in part on the link scan signal data, and the second transducer array configuration may be configured to exchange one or more wireless signals with the first device. In some variations, the link scan signal may comprise one or more of an impulse signal and a pulse signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

In some variations, the first device may comprise an implantable medical device and the second device may comprise an external wireless device configured to be disposed physically separate from the first device. In some variations, the first transducer array and the second transducer array comprise one or more common transducer elements. In some variations, the first transducer array may comprise a subset of the second transducer array. In some variations, the first transducer array and the second transducer array may comprise distinct transducer elements. In some variations, the first transducer array and the second transducer array may each comprise an acoustic transducer array. In some variations, the acoustic transducer array may comprise an ultrasound transducer array.

Also described are methods of exchanging wireless signals in a wireless system. In some variations, a method may comprise the steps of transmitting a link scan signal from a first device of the wireless system to a second device of the wireless system, receiving the link scan signal using a first transducer array of the second device, processing the received link scan signals, received by one or more transducer elements of the first transducer array of the second device, using a processor of the second device to generate link scan signal data, determining a second transducer array configuration of the second device based at least in part on the link scan signal data, and exchanging one or more wireless signals with the first device using the second transducer array configuration of the second device. In some variations, the link scan signal may comprise one or more of an impulse signal and a pulse signal. In some variations, the pulse signal may comprise one or more cycles of a carrier frequency of the pulse signal.

In some variations, processing the received link scan signal received by a transducer element of the first transducer array may comprise determining an impulse response of the wireless system. In some variations, processing the received link scan signal may further comprise performing convolution of the impulse response of the wireless system corresponding to one or more transducer elements of the first transducer array with one or more template signals. In some variations, the link scan signal data may comprise the output signal of the convolution.

In some variations, the link scan signal data may comprise one or more of an absolute amplitude, a relative amplitude, an absolute signal strength, a relative signal strength, an absolute phase, a relative phase, an absolute time delay and a relative time delay of the output signal of the convolution. In some variations, the template signal may comprise a pulse signal. In some variations, the duration of the template signal may be greater than about 5 cycles of a carrier frequency of the template signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

In some variations, determining the second transducer array configuration of the second device may comprise determining one or more of an amplitude, a signal strength, a phase and a time delay for transmitting wireless signals through one or more transducer elements of the second transducer array. In some variations, determining the one or more of the amplitude, the signal strength, the phase and the time delay for transmitting wireless signals through one or more transducer elements of the second transducer array may comprise performing one or more of cross-correlation and time reversal. In some variations, determining the one or more of the amplitude, the signal strength, the phase and the time delay for transmitting wireless signals through one or more transducer elements of the second transducer array may further comprise interpolation of one or more of the amplitudes, the signal strengths, the phases and the time delays based on the relative spatial positions of the transducer elements of the first transducer array and the second transducer array. In some variations, determining the second transducer array configuration may comprise a method of closed-loop powering.

In some variations, the first device may comprise an implantable medical device and the second device may comprise an external wireless device configured to be disposed physically separate from the first device. In some variations, the first transducer array and the second transducer array may comprise one or more common transducer elements. In some variations the first transducer array may comprise a subset of the second transducer array. In some variations, the first transducer array and the second transducer array may comprise distinct transducer elements. In some variations, the first transducer array and the second transducer array may each comprise an acoustic transducer array. In some variations, the acoustic transducer array may comprise an ultrasound transducer array.

Also described are systems configured to exchange one or more of power and data. In some variations, a system may comprise a first device configured to transmit a link scan signal and a feedback signal, and a second device comprising a first transducer array, a second transducer array, and a processor, wherein the first transducer array may be configured to receive the link scan signal and the feedback signal from the first device, the processor may be configured to process the received link scan signals and the received feedback signals received by one or more transducer elements of the first transducer array to generate feedback signal data, and determine a second transducer array configuration based at least in part on the feedback signal data, and the second transducer array configuration may be configured to exchange one or more wireless signals with the first device.

Also described are methods of exchanging wireless signals in a wireless system. In some variations, a method may comprise the steps of transmitting a link scan signal and a feedback signal from a first device of the wireless system to a second device of the wireless system, receiving the link scan signal and the feedback signal using a first transducer array of the second device, processing the received link scan signals and the received feedback signals, received by one or more transducer elements of the first transducer array of the second device, using a processor of the second device to generate feedback signal data, determining a second transducer array configuration of the second device based at least in part on the feedback signal data, and exchanging one or more wireless signals with the first device using the second transducer array configuration of the second device.

In some variations, the link scan signal may comprise one or more of an impulse signal and a pulse signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

In some variations, processing the received link scan signal and the received feedback signal may comprise performing deconvolution of the received feedback signal with the received link scan signal. In some variations, processing the received link scan signal received by a transducer element of the first transducer array may comprise determining an impulse response of the wireless system. In some variations, processing the received link scan signal and the received feedback signal may comprise performing deconvolution of the received feedback signal with the impulse response of the wireless system.

In some variations, the method may further comprise the step of extracting one or more portions of the output signal of the deconvolution using a processor of the second device. In some variations, extracting the one or more portions of the output signal of the deconvolution may comprise finding one or more regions of the output signal of the deconvolution with a settled amplitude.

In some variations, determining the second transducer array configuration of the second device may comprise determining one or more of an amplitude, a signal strength, a phase and a time delay for transmitting wireless signals through one or more transducer elements of the second transducer array. In some variations, determining the one or more of the amplitude, the signal strength, the phase and the time delay for transmitting wireless signals through one or more transducer elements of the second transducer array may comprise performing one or more of cross-correlation and time reversal. In some variations, determining the one or more of the amplitude, the signal strength, the phase and the time delay for transmitting wireless signals through one or more transducer elements of the second transducer array may further comprise interpolation of one or more of the amplitudes, the signal strengths, the phases and the delays based on the relative spatial positions of the transducer elements of the first transducer array and the second transducer array. In some variations, determining the second transducer array configuration may comprise a method of closed-loop powering.

Also described are methods of decoding data signals in a wireless system. In some variations, a method may comprise the steps of transmitting a link scan signal from a first device of the wireless system to a second device of the wireless system, receiving the link scan signal using one or more transducer elements of the second device, processing the received link scan signal using a processor of the second device to generate link scan signal data, generating a pre-distorted data signal based on the link scan signal data using the processor of the second device, transmitting the pre-distorted data signal from the second device to the first device, receiving the pre-distorted data signal using one or more transducer elements of the first device, and processing the received pre-distorted data signal using a processor of the first device to generate decoded data.

In some variations, the link scan signal may comprise an impulse signal, and generating the pre-distorted data signal may comprise performing deconvolution of a data signal with the received link scan signal. In some variations, the link scan signal data may comprise an impulse response of the wireless system, and generating the pre-distorted data signal may comprise performing deconvolution of a data signal with the impulse response of the wireless system.

In some variations, the first device may comprise an implantable medical device, the second device may comprise an external wireless device configured to be disposed physically separate from the first device, and the pre-distorted data signal may comprise a downlink data signal. In some variations, the first device may comprise an external wireless device, the second device may comprise an implantable medical device configured to be disposed physically separate from the first device, and the pre-distorted data signal may comprise an uplink data signal.

Also described are methods of decoding data signals in a wireless system. In some variations, a method may comprise the steps of transmitting a data signal from a first device of the wireless system to a second device of the wireless system, receiving the data signal using a plurality of transducer elements of the second device, applying predetermined delays to one or more received data signals, received using the plurality of transducer elements of the second device, using a processor of the second device to generate delayed data signals, summing two or more delayed data signals using the processor of the second device to generate one or more delayed and summed data signals, and decoding the data signal using the processor of the second device based at least in part on the one or more delayed and summed data signals.

In some variations, the method may further comprise the steps of transmitting a feedback signal from the first device to the second device prior to transmitting the data signal, receiving the feedback signal using one or more transducer elements of the second device, processing the received feedback signal using the processor of the second device to generate feedback signal data, and computing the predetermined delays based at least in part on the feedback signal data.

In some variations, the method may further comprise the steps of transmitting a link scan signal from the first device to the second device prior to transmitting the data signal, receiving the link scan signal using one or more transducer elements of the second device, processing the received link scan signal using the processor of the second device to generate link scan signal data, and computing the predetermined delays based at least in part on the link scan signal data.

In some variations, the first device may comprise an implantable medical device, the second device may comprise an external wireless device configured to be disposed physically separate from the first device, and the data signal may comprise an uplink data signal. In some variations, the first device may comprise an external wireless device, the second device may comprise an implantable medical device configured to be disposed physically separate from the first device, and the data signal may comprise a downlink data signal.

Also described are methods of calibrating a wireless system. In some variations, a method may comprise the steps of transmitting one or more test signals comprising one or more carrier frequencies from a first device of the wireless system to a second device of the wireless system, receiving the one or more test signals using the second device, processing the one or more received test signals using a processor of the second device to generate test signal data, determining one or more selected carrier frequencies using the processor of the second device based at least in part on the test signal data, transmitting one or more wireless commands from the second device to the first device comprising information corresponding to the one or more selected carrier frequencies, and storing the information corresponding to the one or more selected carrier frequencies in a memory of the first device.

In some variations, the method may further comprise the step of transmitting a wireless signal comprising the one or more selected carrier frequencies from the first device to the second device. In some variations, the transmitted wireless signal may comprise one or more of a feedback signal, a link scan signal, and an uplink data signal. In some variations, determining the one or more selected carrier frequencies may comprise determining one or more carrier frequencies at which a parameter of the received test signal may have a value greater than a predetermined threshold. In some variations, the parameter of the received test signal may comprise one or more of a signal strength, a signal amplitude, a signal power, a signal energy, a signal-to-noise ratio, a signal-to-interference ratio, a link efficiency, and a link gain. In some variations, the memory of the first device may comprise one or more of a non-volatile memory and a volatile memory.

DETAILED DESCRIPTION

I. Systems

A. Overview

Generally described herein are systems, devices, and methods for establishing a wireless link between two or more wireless devices of a wireless system. Generally, a wireless system may comprise one or more wireless monitors or wireless implantable devices or implantable medical devices, and one or more wireless devices or external wireless devices. The wireless implantable device may be wirelessly powered or recharged by the external wireless device using wireless power transfer. The wireless implantable device may also wirelessly communicate data and/or commands bi-directionally with the external wireless device.

Figure 1:
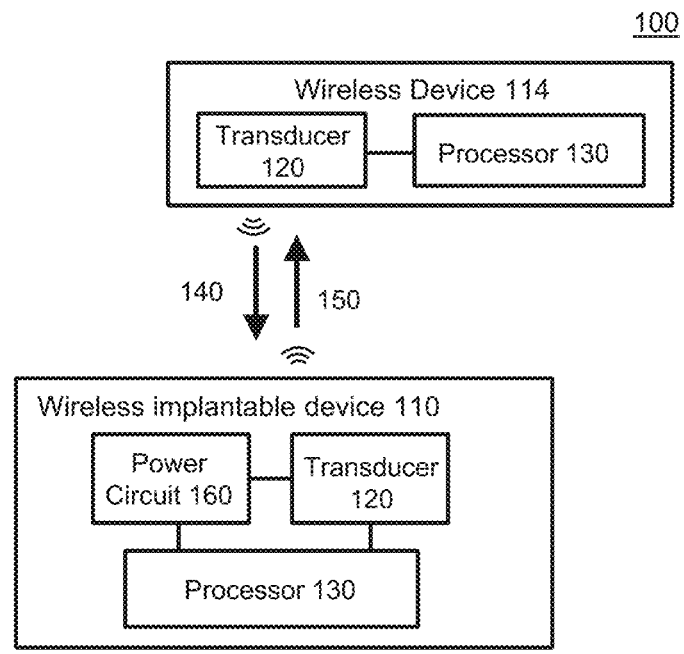
FIG. 1 is a schematic block diagram of an illustrative variation of a wireless system.

FIG. 1 is a schematic block diagram of an illustrative variation of a wireless system (100) comprising a wireless implantable device (110) and a wireless device (114), where each of the components are described in more detail herein. The wireless device (114) may transmit a wireless downlink signal (140) to the wireless implantable device (110), comprising one or more of power, data, a command, a signal, combinations thereof, and the like. The wireless device (114) may receive a wireless uplink signal (150) from the wireless implantable device (110), comprising one or more of power, data, a command, a signal, combinations thereof, and the like. Each of these signals are also described in more detail herein.

Figure 2:
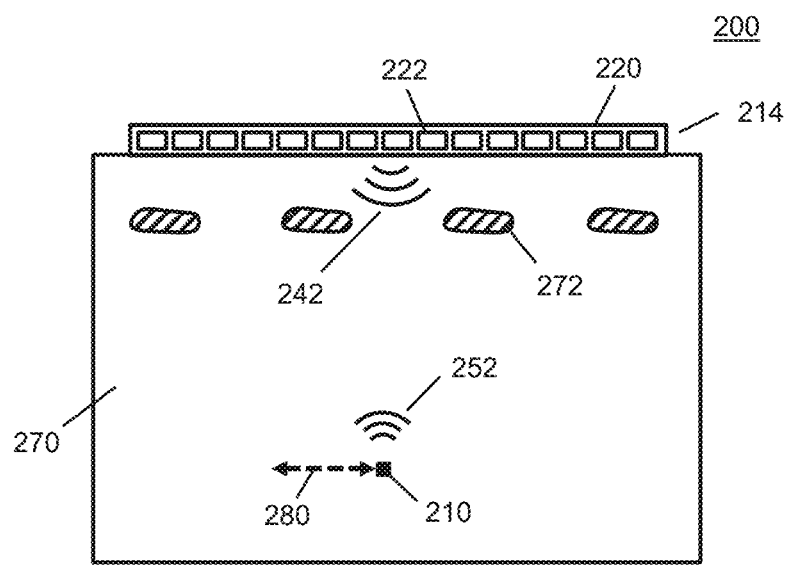
FIG. 2 is a cross-sectional schematic view of an illustrative variation of a wireless system.

FIG. 2 is an illustrative variation of a system comprising a first device (210) implanted in the heart, surrounded by tissue (270) and a rib cage or ribs (272), along with an external second device (214) comprising one or more transducer arrays (220) comprising one or more transducer elements (222). In some variations, the second device (214) may be placed on a patient's chest. The second device (214) may be configured to transmit a downlink signal (242) comprising one or more of an interrogation signal, power signal, a downlink command, a downlink data signal, and the like, to the first device (210). The first device (210) may be configured to generate a wireless signal (252) comprising one or more of a feedback signal, an uplink data signal, a reflection signal from the first device (210), a backscatter signal from the first device (210), and the like. In some variations, the first device (210) may move relative to the second device (214) along a spatial path (280) or a periodic trajectory.

B. Wireless Monitor

Generally, a wireless monitor may be configured to perform one or more functions including, but not limited to, sensing, monitoring, stimulation, delivering therapy, combinations thereof, and the like. In some variations, the wireless monitor may receive and/or transmit one or more of wireless power, wireless data, wireless commands, and wireless signals to/from an external wireless device or another wireless monitor. For example, the wireless monitor may be configured to monitor, measure and/or process one or more physiological parameters of a patient.

In some variations, the wireless monitors described herein may be configured to perform only a sub-set of the measurements, processing, data storage, and/or signal transmission steps described herein. In some variations, the wireless monitors may comprise only a sub-set of the components or blocks described herein. For example, in some variations, a wireless monitor may include only a transducer, a power circuit and a processor. As another example, in some variations, a wireless monitor may include one or more transducers, a power circuit, a processor, a sensor and a memory. In some variations, a wireless monitor may comprise other components in addition to what may be described herein (e.g., sensors, stimulators, delivery and/or anchoring mechanisms, mechanical parts to enable deployment in the body or organ, or other components).

In some variations, a wireless monitor may be implanted inside a patient or an animal. In some variations, a wireless monitor, as described herein, may be coupled (e.g., attached) to an implantable device, or any part of an implantable device. For example, one or more wireless monitors may be attached to a prosthetic heart valve or a stent. As another example, one or more wireless monitors may be attached to one or more of a pulse generator and/or one or more leads of a pacemaker, an implantable cardioverter defibrillator, and/or cardiac resynchronization therapy devices. In some variations, the wireless monitor may be implanted within or on one or more of a cardiac structure (e.g., heart valve, heart chamber), a vascular structure (e.g., pulmonary artery, any other blood vessel), body lumen, body cavity, tissue, organ, and the like.

In some variations, a wireless monitor may comprise one or more components or blocks described herein for an implantable device. In some variations, an implantable device may comprise one or more components or blocks described herein for a wireless monitor. For example, a wireless monitor may comprise one or more of a transducer, a power circuit, an energy storage device, a sensor, a processor, a memory, a wireless transmitter, a wireless receiver, a multiplexer circuit, combinations thereof, and the like.

C. Implantable Device

Generally, an implantable device, a wireless implantable device, or an implantable medical device described herein may be configured to be implanted inside a patient or an animal. In some variations, the implantable device may be a wireless implantable device. In some variations, the wireless implantable device may receive and/or transmit one or more of wireless power, wireless data, wireless commands, and wireless signals to/from an external wireless device or another wireless implantable device. In some variations, a wireless implantable device may be configured to perform one or more functions including, but not limited to, sensing, monitoring, stimulation, delivering therapy, combinations thereof, and the like. In some variations, a wireless implantable device may be a wireless monitor.

In some variations, an implantable device may comprise one or more of a prosthetic heart valve, prosthetic heart valve conduit, valve leaflet coaptation devices, annuloplasty rings, valve repair devices (e.g., clips, pledgets), septal occluders, appendage occluders, ventricular assist devices, pacemakers (e.g., including leads, pulse generator), implantable cardioverter defibrillators (e.g., including leads, pulse generator), cardiac resynchronization therapy devices (e.g., including leads, pulse generator), insertable cardiac monitors, stents (e.g., coronary or peripheral stents, fabric stents, metal stents), stent grafts, scaffolds, embolic protection devices, embolization coils, endovascular plugs, vascular patches, vascular closure devices, interatrial shunts, parachute devices for treating heart failure, cardiac loop recorders, combinations thereof, and the like. For example, a prosthetic heart valve may comprise one or more of a transcatheter heart valve (THV), self-expandable THV, balloon expandable THV, surgical bioprosthetic heart valve, mechanical valve, and the like.

Generally, the implantable devices described herein may be located in or near (e.g., adjacent, proximal) any region in the body including, but not limited to, a heart valve (e.g., aortic valve, mitral valve), a heart chamber (e.g., left ventricle or LV, left atrium or LA, right ventricle or RV, right atrium or RA), a blood vessel (e.g., pulmonary artery, aorta, superficial femoral artery, coronary artery, pulmonary vein, and the like), heart tissue (e.g., heart muscle or wall, septum), gastrointestinal tract (e.g., stomach, esophagus), bladder, combinations thereof, and the like.

As shown in FIG. 1, the wireless implantable device (110) may comprise a transducer (120), a processor (130) and a power circuit (160). The wireless device (114) may comprise a transducer (120) and a processor (130). Each of these components are described in more detail herein.

a. Transducer

Generally, a transducer described herein may be configured to convert between a wireless energy modality and an electrical signal. In some variations, a transducer of a device may be configured to exchange one or more of wireless power, a wireless signal, wireless data, a wireless command, combinations thereof, and the like, with another device and/or with another transducer of the same device. In some variations, the transducer (120) may be configured to receive and/or transmit signals using one or more of mechanical waves (e.g., acoustic, ultrasonic or ultrasound, vibrational), magnetic fields (e.g., inductive), electric fields (e.g., capacitive), electromagnetic waves (e.g., radiofrequency or RF, optical), galvanic coupling, surface waves, combinations thereof, and the like, as well as convert the signals into and/or from electrical signals. A transducer, as described herein, may be included in one or more of a wireless implantable device, a wireless monitor, an external wireless device, and the like (e.g., any of the devices described herein).

In some variations, a transducer (120) may comprise one or more of an ultrasonic transducer, a radiofrequency (RF) transducer (e.g., a coil, an RF antenna), a capacitive transducer, combinations thereof, and the like. In some variations, an ultrasonic transducer may comprise one or more of a piezoelectric device, a capacitive micromachined ultrasonic transducer (CMUT), a piezoelectric micromachined ultrasonic transducer (PMUT), combinations thereof, and the like. In some variations, an ultrasonic transducer may convert pressure and/or force into an electrical signal, and/or vice versa. In some variations, the transducer (120)) may comprise one or more ultrasonic transducers that may be of one or more types, including but not limited to, piston (e.g., rod, plate), cylindrical, ring, spherical (e.g., shell), flexural (e.g., bar, diaphragm), flextensional, combinations thereof, and the like. In some variations, a piezoelectric device may be made of one or more of lead zirconate titanate (PZT), PMN-PT. Barium titanate (BaTiO3), polyvinylidene difluoride (PVDF), Lithium niobate (LiNbO3), any derivates thereof, and the like. In some variations, a radiofrequency (RF) transducer may be configured for transmitting and/or receiving near-field and/or non-near-field (e.g., far-field) signals. For example, an RF antenna may be configured for non-near-field transmission and/or reception of power, data and/or other signals. An RF coil may be configured for near-field (e.g., inductive) transmission and/or reception of power, data and/or other signals.

In some variations, a transducer (120) may comprise one or more ultrasonic transducers for one or more of receiving wireless power, transmitting/receiving data to/from another wireless device, and transmitting/receiving signals to/from another wireless device. For example, an ultrasonic transducer of a wireless monitor may be designed to operate at a frequency between about 20 KHz and about 20 MHz for receiving power from an external wireless device. Operation in such a frequency range may be useful to miniaturize an ultrasonic transducer to millimeter or sub-millimeter dimensions, which may be advantageous for integrating one or more wireless monitors onto another implantable device (e.g., a transcatheter heart valve, a stent). In some variations, an ultrasonic transducer may have an impedance with a real part in the order of about hundreds of Ohms to about hundreds of kilo Ohms (e.g., between about 100Ω and about 500 kΩ. In some variations, an ultrasonic transducer may have an impedance with a real part in the order of tens of Ohms.

In some variations, a transducer (120) may comprise a single transducer element (e.g., ultrasonic piezoelectric device) that may allow miniaturization of the wireless monitor. In some variations, the single transducer element may be configured to receive a power signal (e.g., ultrasonic power) transmitted from an external wireless device and convert the signal to electrical power. Additionally, or alternatively, the single transducer element may be configured to receive downlink data (e.g., using an ultrasonic signal) and/or other signals from an external wireless device or a wireless monitor. In some variations, the single transducer element may be configured to transmit uplink data (e.g., using an ultrasonic signal) and/or other signals to an external wireless device or a wireless monitor. In some variations, the single transducer element may comprise an ultrasonic transducer configured to perform one or more of receiving ultrasonic power from another device (e.g., external wireless device), performing bi-directional ultrasonic data communication or signal exchange (e.g., uplink and downlink) with another device (e.g., external wireless device, wireless monitor), combinations thereof, and the like.

In some variations, a transducer (120) may comprise more than one transducer element or one or more arrays of transducer elements. For example, the transducer (120) may comprise an array of ultrasonic transducer elements. As another example, a first transducer element may comprise an RF coil configured to receive power and communicate data and/or other signals with an external wireless device. A second transducer element may comprise an ultrasonic transducer configured to transmit and/or receive other signals. In some variations, an ultrasonic transducer of an external wireless device may comprise one or more arrays of ultrasonic transducer elements configured to generate an ultrasonic beam for one or more of power transfer, data transfer and/or exchange of other signals with a wireless monitor.

In some variations, a transducer (120) comprising a plurality of transducer elements may be configured to perform a predetermined set of functions. For example, a first transducer element may be configured to recover wireless power, a second transducer element may be configured to receive data and/or signals, and a third transducer element may be configured to transmit data and/or signals.

Small transducer size may allow one or more wireless monitors to be miniaturized, which may be useful for attaching one or more wireless monitors to another implantable device such as a cardiac implantable device (e.g., prosthetic heart valve), and/or may allow minimally invasive delivery of the wireless monitor or wireless implantable device into the body (e.g., via percutaneous or transcatheter techniques). In some variations, a transducer may have a volume of less than about 10 cm$^3$.

In some variations, a transducer (e.g., an ultrasonic transducer) of a wireless monitor may be oriented or angled towards one or more of a transducer of another wireless monitor, a transducer of the external wireless device, combinations thereof, and the like. This may facilitate the reliability of transmitting/receiving power, data and/or other signals between a wireless monitor and an external wireless device, or between two wireless monitors.

In some variations, a wireless monitor may comprise one or more transducers. In some variations, one or more wireless monitors may share one or more transducers. For example, in some variations, more than one wireless monitor may be connected to a transducer (e.g., an RF coil) with more than one feed or port. For example, a stent device may comprise an RF coil with two or more feeds or ports, to which two or more wireless monitors may be connected. In some variations, two or more wireless monitors may be connected to a single feed or port of a transducer (e.g., two or more wireless monitors connected in parallel at a single feed or port of an RF coil).

b. Power Circuit

Generally, a power circuit described herein may be configured to recover, condition, detect, select, combine, store and/or supply power or energy. For example, a power circuit may be configured to recover wireless power received by a transducer and convert it into usable energy for powering one or more circuit blocks of a wireless monitor. In some variations, the power circuit may comprise one or more energy storage elements (e.g., battery, capacitor) configured to store energy received by the transducer. The power circuit may be further configured to control (e.g., regulate, limit) the power provided to one or more components (e.g., circuit blocks) of the wireless monitor. The combination of the power circuits and transducers described herein may be useful for power, data and/or signal transfer between an external wireless device and one or more low-power devices (e.g., wireless monitor) implanted in a patient. In some variations, the power circuit (160) may comprise one or more of a power recovery circuit, a power management circuit, a power detector circuit, a power distribution circuit, combinations thereof, and the like.

In some variations, the power circuit (160) may comprise an AC-DC converter configured to convert alternating current (AC) voltage into a DC voltage. For example, the power circuit (160) may comprise a rectifier configured to convert AC voltage at the terminals of a transducer into a DC voltage rail. The rectifier may comprise one or more of a passive rectifier, an active rectifier, a passive voltage doubler, combinations thereof, and the like. In some variations, the power circuit (160) may comprise a DC-DC converter configured to convert a DC voltage rail into another DC voltage rail. For example, the power circuit (160) may comprise a switched-capacitor DC-DC converter, a charge pump, combinations thereof, and the like. In some variations, the power circuit (160) may comprise a voltage regulator (e.g., a low-dropout regulator (LDO) circuit, a voltage clamp circuit) configured to generate a regulated or constant DC voltage rail. In some variations, the power circuit (160) may comprise one or more reference generation circuits such as a current reference circuit, a bandgap reference circuit, a voltage reference circuit, combinations thereof, and the like.

In some variations, the power circuit (160) may be configured to recover and/or combine wireless power received by a plurality of transducer elements located on a wireless monitor. For instance, such a power circuit connected to a plurality of transducer elements may perform one or more of AC power combining, DC power combining, DC voltage combining, DC current combining, any combinations thereof, and the like.

In some variations, the power circuit (160) may comprise a power detector circuit configured to detect or measure power and/or energy at one or more of its inputs. In some variations, the power detector circuit may be configured to provide one or more supply voltages or power to one or more circuit blocks in a wireless monitor depending on detection of power at one or more inputs. In some variations, the power detector circuit may comprise one or more of a power ORing circuit, a power combining circuit, a power selection circuit, one or more diodes and one or more switches, as described herein. A power ORing circuit, a power combining circuit or a power selection circuit may generally operate on a plurality of power sources at its input and generate one or more power or voltage supplies at its output. For example, a power combining circuit may combine power from a plurality of sources. For example, a power selection circuit may select power from a power source out of a plurality of power sources.

In some variations, the power circuit (160) may comprise an energy storage device comprising one or more of a capacitor, a super-capacitor, a rechargeable or secondary battery, a non-rechargeable or primary battery, combinations thereof, and the like. In some variations, the power circuit (160) may comprise a rechargeable battery for energy storage, along with a capacitor in parallel with the battery, wherein the capacitor may sink/supply at least a part of the current during charging/discharging transients of the rechargeable battery.

In some variations, the power circuit (160) may be separate from an energy storage device. In some variations, the power circuit (160) may not include any energy storage device, and the wireless monitor may be powered by another device (e.g., external wireless device, another wireless monitor, and the like) during the operation of the wireless monitor. In some variations, power may be provided to a wireless monitor until it completes a predetermined set of functions, and the wireless monitor may remain inactive until it is powered again. A power circuit without an energy storage device may allow reduction in the size of the power circuit and the wireless monitor.

In some variations, the systems, devices, and methods disclosed herein may comprise one or more systems, devices, and methods described in U.S. Pat. No. 9,544,068, filed on May 13, 2014, U.S. Pat. No. 10,177,606, filed on Sep. 30, 2016, U.S. Pat. No. 10,014,570, filed on Dec. 7, 2016, and International Application No. PCT/US2020/041696, filed on Jul. 10, 2020, the contents of each of which are hereby incorporated by reference in its entirety.

c. Energy Storage Device

Generally, an energy storage device described herein may be configured to store energy, which may be used to power one or more circuit blocks of a wireless implantable device or wireless monitor. In some variations, an energy storage device may comprise one or more of a capacitor, a super-capacitor, a rechargeable or secondary battery, a non-rechargeable or primary battery, combinations thereof, and the like.

In some variations, an energy storage device of a wireless implantable device (110) may comprise a battery (e.g., a rechargeable battery) with a capacity of less than about 100 milli-Watthour (about 360 Joules). In some variations, an energy storage device of a wireless implantable device (110) may comprise a battery (e.g., a rechargeable battery) with a capacity of less than about 10 milli-Watthour (36 Joules). Such a battery may be significantly smaller in size than batteries used in conventional implantable devices such as pacemakers or deep brain stimulators, allowing miniaturization of the wireless implantable device (110) to dimensions on the order of a centimeter, a millimeter, or less than a millimeter.

In some variations, an energy storage device of a wireless implantable device (110) may comprise a capacitor with capacitance between about 0.1 nano-Farads (nF) and about 100 micro-Farads (µF). Such a capacitor may be on-chip (i.e., included within an integrated circuit) or off-chip. In some variations, a wireless implantable device (110) may comprise a plurality of energy storage devices, each of which may comprise any type of energy storage device described herein.

d. Sensor

Generally, a sensor described herein may be configured to sense or measure one or more parameters. In some variations, the sensor may comprise one or more of a pressure sensor, a flow sensor, a transducer (e.g., an ultrasonic transducer, an infrared/optical photodiode, an infrared/optical LED, an RF antenna, an RF coil), a temperature sensor, an electrical sensor (e.g., using electrodes for measuring impedance, electromyogram or EMG, electrocardiogram or ECG, and the like), a magnetic sensor (e.g., RF coil), an electromagnetic sensor (e.g., infrared photodiode, optical photodiode, RF antenna), a neural sensor (e.g., for sensing neural action potentials), a force sensor (e.g., a strain gauge), a flow or a velocity sensor (e.g., hot wire anemometer, vortex flowmeter), an acceleration sensor (e.g., accelerometer), a chemical sensor (e.g., pH sensors, protein sensor, glucose sensor), an oxygen sensor (e.g., pulse oximetry sensor, myocardial oxygen consumption sensor), an audio sensor (e.g., a microphone to detect heart murmurs, prosthetic valve murmurs, auscultation), a sensor for sensing other physiological parameters (e.g., sensors to sense heart rate, breathing rate, arrhythmia, motion of heart walls), a stimulator (e.g., for stimulation and/or pacing function), combinations thereof, and the like.

In some variations, one or more pressure sensors (alternatively referred to as a pressure transducer) may be used for one or more of monitoring heart function and/or heart failure (e.g., measuring pressure in the LV, RV, LA, RA, pulmonary artery, aorta, and the like), monitoring a prosthetic valve (e.g., valve pressure gradients to monitor stenosis), monitoring a stent device (e.g., measuring pressure in the lumen), estimation and/or verification of blood velocity measurements (e.g., using the Bernoulli equation), combinations thereof, and the like. In some variations, one or more pressure sensors may be of the following types including, but not limited to, an absolute pressure sensor, a gauge pressure sensor, a sealed pressure sensor, a differential pressure sensor, an atmospheric pressure sensor, combinations thereof, and the like. In some variations, one or more pressure sensors may be based upon one or more pressure-sensing technologies including, but not limited to, resistive (e.g., piezoresistive, using a strain gauge or a membrane to create a pressure-sensitive resistance, and the like), capacitive (e.g., using a diaphragm or a membrane to create a pressure-sensitive capacitance, and the like), piezoelectric, optical, resonant (e.g., pressure-sensitive resonance frequency of a structure, and the like), combinations thereof, and the like. In some variations, a pressure sensor may be manufactured using Micro-Electro-Mechanical Systems (MEMS) technology. In some variations, a pressure sensor may comprise one or more of a stagnation pressure sensor, a static pressure sensor, and the like.

In some variations, a sensor may comprise a stimulator used for stimulating muscles and/or neurons or nerves of one or more of cardiac tissue (e.g., HIS bundle, atrioventricular node), heart chamber (e.g., septal, lateral walls of the LV), blood vessel wall, combinations thereof, and the like. For example, one or more stimulators may be used to stimulate the LV wall for pacing and/or cardiac resynchronization. In some variations, a stimulator may comprise an electrical stimulator (e.g., electrodes), an ultrasonic stimulator (e.g., ultrasonic transducer), an optical stimulator (e.g., an optical LED), an infrared stimulator (e.g., an infrared LED), a thermal stimulator (e.g., electrodes to generate heat in tissue), combinations thereof, and the like.

In some variations, a sensor may comprise one or more of a sensing transducer and sensing circuits. In some variations, sensing circuits may comprise one or more of a signal conditioning circuit, an analog front-end (AFE), an amplifier, front-end amplifier (FEA), an instrumentation amplifier, a filter, an anti-aliasing filter, an analog-to-digital converter (ADC), a comparator, a reference generator, a supply generator, a digital controller, a bias circuit, a clock circuit, a timer circuit, an oscillator, combinations thereof, and the like.

In some variations, a sensor may be configured to measure a physiological parameter of a patient. In some variations, the physiological parameter of the patient may comprise one or more of an intracardiac pressure, an intravascular pressure, a blood pressure, a blood velocity, a blood flow; a blood oxygen level, a heart rate, a breathing rate, a temperature, a voltage (e.g., an electrical voltage generated by tissue such as ECG, EMG, and the like), a current, an impedance (e.g., tissue impedance, thoracic impedance, and the like), a neural signal, a heart sound, combinations thereof, and the like.

e. Processor

Generally, a processor (e.g., CPU) described herein may receive, transmit and/or process data and/or other signals, and/or control one or more components of the system (e.g., control one or more circuit blocks of a wireless monitor). The processor may be configured to receive, process, compile, compute, store, access, read, write, transmit and/or generate data and/or other signals. Additionally, or alternatively, one or more blocks of the processor of a wireless monitor may be configured to control one or more other blocks of the processor and/or one or more components (e.g., transducer, power circuit, memory, sensor, wireless transmitter, wireless receiver, and the like) of a wireless monitor. A processor, as described herein, may be included in one or more of a wireless monitor, a wireless implantable device, an external wireless device, and the like.

In some variations, a processor (130) of a wireless device (114) may be configured to process a signal (e.g., a feedback signal) and take an action (e.g., generate feedback signal data). In some variations, the processor (130) of the wireless device (114) may be configured to process a signal (e.g., a feedback signal), generate data (e.g., feedback signal data) and determine a transducer configuration of the wireless device (e.g., signal strengths and delays applied to the elements of a transducer array) for powering a wireless implantable device (110), as described in detail herein. For example, the processor may comprise an amplifier, a phase detector, a frequency detector, a digital signal processor, an analog signal processor, an integrator, an adder circuit, a multiplier circuit, a finite state machine, combinations thereof, and the like, for performing such computations. In some variations, the processor (130) of the wireless device (114) and/or of the wireless implantable device (110) may be configured to process one or more wireless signals transmitted through a wireless link (e.g., the link between the wireless implantable device, 110, and the wireless device, 114) to determine an impulse response of the wireless system.

In some variations, a processor (130) of a wireless implantable device (110) may be configured to process a parameter (e.g., a physiological parameter of a patient) measured by a sensor, and generate parameter data (e.g., physiological parameter data). In some variations, a processor (130) may be configured to control one or more circuit blocks of a wireless implantable device (110) and/or a wireless device (114). For example, the processor (130) may be configured to control a wireless transmitter of the wireless implantable device (110) in order to adjust one or more parameters of the wireless transmitter (e.g., transmit frequency). In some variations, a processor (130) of a wireless implantable device (110) and/or a wireless device (114) may be configured to monitor one or more circuit blocks or components of the wireless implantable device (110) and/or the wireless device (114). In some variations, a processor (130) of a wireless implantable device (110) may be configured to digitize an analog signal (e.g., a signal received by a transducer).

In some variations, a processor (130) may comprise a data communication circuit that may be a data receiver, which may be configured to access or receive data and/or other signals from one or more of a transducer, a sensor (e.g., pressure sensor) and a storage medium (e.g., memory, flash drive, memory card). For example, the processor may comprise one or more of a signal receiver (e.g., detecting an interrogation signal), an envelope detector circuit, an amplifier (e.g., a low-noise amplifier or LNA), a filter, a frequency detector circuit, a phase detector circuit, comparator circuits, decoder circuits, combinations thereof, and the like, to receive data and/or signals through the transducer.

In some variations, a processor (130) may comprise any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may comprise, for example, a general purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), a graphics processing unit (GPU), a central processing unit (CPU), and/or an application specific integrated circuit (ASIC). Software modules (executed on hardware) may be expressed in a variety of software languages (e.g., computer code), including C, C++, Java®, Python, Ruby, Visual Basic R, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some variations, a processor (130) of a wireless implantable device (110) may comprise one or more of an envelope detection circuit, an energy detector circuit, a power detector circuit, a voltage sensor, a time-to-digital converter (TDC) circuit, an integrator circuit, a sampling circuit, an analog-to-digital converter (ADC) circuit, a timer circuit, a clock, a counter, an oscillator, a phase-locked loop (PLL), a frequency locked loop (FLL), combinations thereof, and the like. In some variations, a processor (130) may comprise an amplifier, a phase detector, a frequency detector, a digital signal processor, an integrator, an adder circuit, a multiplier circuit, a finite state machine, combinations thereof, and the like, for performing computations.

In some variations, a processor (130) of a wireless implantable device (110) may comprise a data communication circuit that may be a data transmitter or a wireless transmitter, which may be configured to generate or transmit data and/or other signals through one or more of a transducer, a storage medium, and the like. For example, a processor (130) of a wireless implantable device (110) may comprise one or more of a signal transmitter, an uplink data transmitter, an oscillator, a power amplifier, a mixer, an impedance matching circuit, a switch, a driver circuit, combinations thereof, and the like, to generate or transmit data and/or signals via the transducer. In some variations, a first processor may be included in a wireless monitor or a wireless implantable device, and a second processor may be included in an external wireless device.

f. Memory

Generally, an implantable device, a wireless monitor and/or the wireless device described herein may comprise a memory configured to store data and/or information. In some variations, the memory may be of one or more types including, but not limited to, random access memory (RAM), static RAM (SRAM), dynamic RAM (DRAM), resistive random-access memory (ReRAM or RRAM), magnetoresistive random-access memory (MRAM), ferroelectric random-access memory (FRAM), standard-cell based memory (SCM), shift registers, read-only memory (ROM), programmable read-only memory (PROM), erasable programmable read-only memory (EPROM), electrically erasable programmable read-only memory (EEPROM), flash memory (e.g., NOR, NAND), embedded flash, volatile memory, non-volatile memory, one time programmable (OTP) memory, combinations thereof, and the like.

In some variations, the memory may store instructions and/or data to cause the processor to execute modules, processes, and/or functions (e.g., executing a search algorithm) associated with a wireless monitor and/or an external wireless device. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) may be non-transitory in the sense that it may not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

In some variations, the memory may be configured to store sensor data (e.g., physiological parameter data), received data and/or data generated by the wireless monitor (e.g., data generated by a processor of the wireless monitor, calibration parameters, and the like) and/or by the external wireless device (e.g., a reference feedback signal in a frequency domain representation and/or a time domain representation). In some variations, the memory of a wireless monitor may be configured to store data generated upon processing signals sensed by a sensor (e.g., blood pressure data sensed by a pressure sensor that may be included in a wireless monitor). In some variations, the memory may be configured to store data temporarily or permanently.

g. Wireless Transmitter

Generally, a wireless transmitter of a wireless implantable device or a wireless monitor may be configured to wirelessly transmit one or more of a wireless signal, wireless data, a wireless command, and wireless power. For example, a wireless transmitter of a wireless implantable device (110) may comprise one or more of a signal transmitter, an uplink data transmitter, an oscillator, a clock circuit, a power amplifier, a mixer, an impedance matching circuit, a switch, a driver circuit, combinations thereof, and the like, to generate and/or wirelessly transmit data and/or signals via a transducer (120) of the wireless implantable device (110).

h. Wireless Receiver

Generally, a wireless receiver of a wireless implantable device or a wireless monitor may be configured to wirelessly receive one or more of a wireless signal, wireless data, a wireless command, and wireless power. For example, a wireless receiver of a wireless implantable device (110) may comprise one or more of a signal receiver, a data recovery circuit, a clock recovery circuit, a clock circuit, a power recovery circuit, an envelope detector, a wakeup receiver circuit, a data demodulator, an amplifier, a mixer, an analog-to-digital converter (ADC), a phase-locked loop (PLL), a frequency-locked loop (FLL), an impedance matching circuit, a switch, a coherent receiver circuit, a non-coherent receiver circuit, combinations thereof, and the like, to wirelessly receive data and/or signals via a transducer (120) of the wireless implantable device (110).

i. Multiplexer Circuit

Generally, a multiplexer or multiplexer circuit described herein may be configured to decouple one or more of power signal, data signal and/or other signals received and/or transmitted by a transducer. This may be done in order to avoid interference between these signals and ensure proper functioning of a wireless device such as a wireless monitor, a wireless implantable device, and/or an external wireless device. For example, a multiplexer in a wireless monitor may be configured to decouple a power signal from a data signal received by a transducer of the wireless monitor from an external wireless device such that the power signal is provided to the power circuit for power recovery and conditioning, and the data signal is provided to a wireless receiver or a processor for data recovery.

In some variations, the multiplexer may comprise one or more of transmit/receive switches, passive devices (e.g., diodes, relays, MEMS circuits, blockers, passive switches), circulators, frequency selection (e.g., using filters, impedance matching networks), direct wired connections, combinations thereof, and the like.

In some variations, the transmit/receive switches may be driven based on timing control or time multiplexing such that one or more of power signal, data signal and other signals are received by a wireless monitor at different times. In some variations, the transmit/receive switches may be driven based on amplitude selection wherein one or more of power signal, data signal and other signals have different amplitudes. In some variations, the transmit/receive switches may be driven based on frequency selection or frequency multiplexing wherein one or more of power signal, data signal and other signals have different frequencies. In some variations, the transmit/receive switches may be implemented using depletion-mode transistors to operate when the wireless monitor may not have power, stored energy or an established voltage rail.

D. Wireless Device

Generally, a wireless device or external wireless device may refer to any device that is physically separate from a wireless implantable device or a wireless monitor. In some variations, the external wireless device may comprise one or more blocks described herein in the context of the wireless implantable device including, but not limited to, a transducer, a power circuit, an energy storage device, a sensor, a processor, a memory, a wireless transmitter, a wireless receiver, a multiplexer circuit, combinations thereof, and the like. Variations of these blocks as explained herein in the context of a wireless implantable device are applicable here as well.

In some variations, the transducer of the external wireless device may comprise a plurality of ultrasonic transducer elements or an ultrasonic array configured to exchange wireless signals (transmit and/or receive) with one or more wireless implantable devices. As another example, in some variations, the transducer of the external wireless device may comprise one or more RF coils and/or RF antennas. In some variations, the processor of the external wireless device may perform one or more of processing data and/or signals received from one or more wireless monitors, processing data received from one or more other wireless devices, combinations thereof, and the like.

In some variations, an external wireless device may perform one or more functions including, but not limited to, transmitting one or more of wireless power, data and other signals to one or more wireless implantable devices, receiving one or more of wireless data and other signals from one or more wireless implantable devices, processing data and/or signals, performing sensing and/or actuation (e.g., measuring blood pressure, heart rate, heart rate variability, ECG, EKG, thoracic impedance, breathing rate or respiration, patient activity levels, heart sounds, temperature, body weight, blood glucose, blood oxygen, combinations thereof, and the like), storing data or information in memory, communicating with other external wireless devices (e.g., tablet, phone, computer) via wires and/or using wireless links (e.g., Bluetooth), displaying or providing data or information (e.g., visual display on a screen or a monitor, audio signals), generating alerts/notifications (e.g., visual, audio, vibration) to a user (e.g., patient, nurse, doctor), combinations thereof, and the like.

In some variations, an external wireless device may be located at one or more locations including, but not limited to, outside the body (e.g., as a wearable device, a strap, a belt, a handheld device, a probe connected to a measurement setup, a device placed on skin, a device attached to skin using an adhesive, a device attached to skin using other techniques, a device not touching the patient, a laptop, a computer, a mobile phone, a smartwatch, and the like), permanently implanted inside the body (e.g., implanted under the skin, along the outer wall of an organ, under a muscle, outside the heart wall, and the like), temporarily implanted (e.g., for a predetermined amount of time) inside the body (e.g., located on a catheter or a probe inserted through a blood vessel, esophagus or the chest wall, used during surgery or procedure), combinations thereof, and the like. In some variations, the external wireless device may have different shapes or forms, including but not limited to, planar, conformal to the body or an organ, flexible, stretchable, flat, shaped like a probe, and the like.

In some variations, the external wireless device may further comprise a communication device configured to permit a user and/or health care professional to control one or more of the devices of the wireless system. The communication device may comprise a network interface configured to connect the external wireless device to another system (e.g., Internet, remote server, database) by wired or wireless connection. In some variations, the external wireless device may be in communication with other devices (e.g., cell phone, tablet, computer, smartwatch, and the like) via one or more wired and/or wireless networks. In some variations, the network interface may comprise one or more of a radiofrequency receiver/transmitter, an optical (e.g., infrared) receiver/transmitter, an acoustic or ultrasonic receiver/transmitter, and the like, configured to communicate with one or more devices and/or networks. The network interface may communicate by wires and/or wirelessly with one or more of the external wireless device, network, database, and server.

The network interface may comprise RF circuitry configured to receive and/or transmit RF signals. The RF circuitry may convert electrical signals to/from electromagnetic signals and communicate with communication networks and other communication devices via the electromagnetic signals. The RF circuitry may comprise well-known circuitry for performing these functions, including but not limited to, an antenna system, an RF transceiver, one or more amplifiers, a tuner, one or more oscillators, a mixer, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VOIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

The communication device may further comprise a user interface configured to permit a user (e.g., subject or patient, predetermined contact such as a partner, family member, health care professional, etc.) to control the external wireless device. The communication device may permit a user to interact with and/or control an external wireless device directly and/or remotely. For example, a user interface of the external wireless device may include an input device for a user to input commands and an output device for a user to receive output (e.g., blood pressure readings on a display device).

In some variations, an output device of the user interface may output one or more of information about the coupling of an external wireless device to tissue or skin, information about the wireless link between the external wireless device and the wireless monitor (e.g., has a reliable link been established), data (e.g., physiological parameter data) measured by one or more of the wireless monitor and the external wireless device, combinations thereof, and the like. In some variations, an output device of the user interface may comprise one or more of a display device and audio device. Data analysis generated by a server may be displayed by the output device (e.g., display) of the external wireless device. Data used in finding a transducer configuration or ensuring that an external wireless device is sufficiently coupled to tissue may be received through the network interface and output visually and/or audibly through one or more output devices of the external wireless device. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

In some variations, an audio device may audibly output one or more of any data, commands, instructions to a user, alarms, notifications, and the like. For example, the audio device may output an audible alarm when the link between a wireless monitor and an external wireless device is disturbed or interrupted, and manual adjustment by a user may be needed. In some variations, an audio device may comprise at least one of a speaker, piezoelectric audio device, magnetostrictive speaker, and/or digital speaker. In some variations, a user may communicate with other users using the audio device and a communication channel. For example, a user may form an audio communication channel (e.g., VOIP call) with a remote health care professional.

In some variations, the user interface may comprise an input device (e.g., touch screen) and output device (e.g., display device) and be configured to receive input data from one or more of the wireless monitor, an external wireless device, network, database, and server. For example, user control of an input device (e.g., keyboard, buttons, touch screen) may be received by the user interface and may then be processed by a processor and memory for the user interface to output a control signal to the wireless monitor. Some variations of an input device may comprise at least one switch configured to generate a control signal. For example, an input device may comprise a touch surface for a user to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio data and recognize a user voice as a control signal.

A haptic device may be incorporated into one or more of the input and output devices to provide additional sensory output (e.g., force feedback) to the user. For example, a haptic device may generate a tactile response (e.g., vibration) to confirm user input to an input device (e.g., touch surface). As another example, haptic feedback may notify that user input is overridden by the external wireless device.

a. Sub-Array

A sub-array may generally refer to any subset of a plurality of transducer elements of a wireless device. In some variations, a sub-array may comprise one or more of a set of adjacent transducer elements, a set of alternating transducer elements (e.g., every second element), a set of every 'n$^{th}$' transducer elements, or any subset of transducer elements of a transducer array. For example, a sub-array may comprise a set of transducer elements selected for efficiently transferring wireless power to a wireless implantable device based on a feedback signal, as described in detail herein. In some variations, a sub-array may comprise a single transducer element of the external wireless device. In some variations, a sub-array may comprise all transducer elements of the external wireless device.

In some variations, sub-arrays may comprise a disjoint set of transducer elements. For example, an external wireless device may comprise a linear 1D array with array elements labeled 1, 2, 3, and so on, where sub-arrays may be comprised of element numbers 1-8, 9-16, 17-24, and so on. In some variations, sub-arrays may comprise an overlapping set of transducer elements. For example, for the example of a linear 1D array, sub-arrays may be comprised of element numbers 1-8, 2-9, 3-10, and so on. In some variations, sub-arrays may have different sizes. For example, different sub-arrays of the same external wireless device may comprise one or more of different number of transducer elements (e.g., some sub-arrays may comprise 4 transducer elements, some sub-arrays may comprise 16 transducer elements), transducer elements with different sizes, combinations thereof, and the like. In some variations, the selection of transducer elements for a predetermined sub-array of the external wireless device may be based upon feedback signal data, as described in detail herein.

b. Transducer Configuration

A transducer configuration (e.g., a transducer array configuration, a configuration of a transducer array) may generally refer to one or more transducer elements of a wireless device configured to exchange one or more of wireless power, data, a command, and a signal with another wireless device. A transducer configuration may also refer to the parameters and settings of the one or more transducer elements (e.g., one or more transducer elements of a transducer array) configured to transmit a signal (e.g., the frequency, amplitude, phase, time delay, duration, and the like, with which the one or more transducer elements may be configured to transmit a signal), and/or to receive a signal (e.g., phase shift, time delay, gain, and the like, with which the one or more transducer elements may be configured to receive a signal). In some variations, a transducer configuration may be selected by a processor of a wireless device (e.g., an external wireless device) based on a feedback signal received from another wireless device (e.g., a wireless implantable device).

In some variations, a transducer configuration configured to transmit wireless signals to a wireless device may be referred to as a transmit transducer configuration (TTC). In some variations, a transducer configuration configured to receive wireless signals from a wireless device may be referred to as a receive transducer configuration (RTC). In some variations, a transducer configuration selected by a processor of a wireless device based on a feedback signal received from another wireless device may be referred to as an optimal transducer configuration (OTC) that may be improved relative to a default transducer configuration, but which may not necessarily be the most optimal transducer configuration. In some variations, a set of transducer elements of the wireless device, along with the driving signals for each of those transducer elements, that may be selectively configured for powering a wireless implantable device and/or transmitting other downlink signals to the wireless implantable device, may be collectively referred to as a sub-array powering snapshot. In some variations, a set of transducer elements of the wireless device configured to receive uplink signals (e.g., data) from a wireless implantable device, along with parameters related to receiving signals, or conditioning received signals, such as gain, phase-shift, delay, filtering, time window for receiving signals, and the like, may be collectively referred to as a sub-array uplink data snapshot.

c. User Prompt

A user prompt (also referred to as user feedback) may generally refer to one or more instructions, notifications, recommendations, alerts, and the like provided by a wireless device to a user. A user prompt may serve a number of purposes including, but not limited to communicating data about the state of charge (SoC) and/or depth of discharge (DoD) of a wireless implantable device's energy storage device, and/or an external wireless device's battery, asking a user to recharge the battery, communicating data about the data transfer and/or an exchange of wireless signals between two wireless devices (e.g., percent data transfer complete), asking a user to manually adjust or reposition a wireless device on a patient's body, combinations thereof, and the like. In some variations, a user prompt may comprise one or more of feedback signal data (e.g., apodizations of one or more transducer elements of a transducer array), link scan signal data, a transducer array configuration, a property of a first data signal, a property of a second data signal, a property of a combined data signal, a property of a delayed and summed data signal, decoded data bits, a property of a pre-distorted data signal, a property of a test signal, combinations thereof, and the like. In some variations, a user prompt may be provided using one or more of visual instructions, audio instructions, vibrations, notifications (e.g., alert, push notification, email, and the like, on the phone, computer, and the like), combinations thereof, and the like. Variations of the communication device, user interface, input device, output device, etc., as described herein, may be used for providing a user prompt.

In some variations, the user prompt (e.g., visual instructions) may comprise one or more of an image, photo, and stylized representation (e.g., schematic, cartoon, diagram) of a patient's chest (e.g., showing one or more of chest, arms, neck, head), current device configuration (e.g., position, angle, tilt, and the like) of the wireless device, target device configuration (e.g., position, angle, rotation, tilt, and the like) of the wireless device, a map showing current/target positions, instructions displayed in the form of text (e.g., a sentence asking the user to move the wireless device towards the patient's left arm, right arm, head, and the like: numbers or percentage representing power received by a wireless device, SoC and/or DoD of the battery, and the like), arrows directing a user to move, rotate and/or adjust a wireless device, LEDs (e.g., steady, blinking), combinations thereof, and the like. For example, in some variations, the current position, as well as a target position, of the wireless device may be overlaid on the image of the chest. A user may be instructed to move the wireless device until it reaches the target position.

In some variations, audio instructions may comprise one or more of voice commands (e.g., asking the user to move the wireless device towards the patient's left arm, asking the user to recharge the wireless device's battery, notifying a user of completed data transfer between two wireless devices), beeps, alarms, combinations thereof, and the like.

d. Network

In some variations, the systems, devices, and methods described herein may be in communication with other wireless devices via, for example, one or more networks, each of which may be any type of network (e.g., wired network, wireless network). The communication may or may not be encrypted. A wireless network may refer to any type of digital network that is not connected by cables of any kind. Examples of wireless communication in a wireless network include, but are not limited to cellular, radio, satellite, and microwave communication. However, a wireless network may be connected to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some variations, the network may be used for remote processing of any data or information used by the wireless system described herein. For example, a processor that may process any data or information related to the wireless system may be located in the same housing as a wireless implantable device and/or in the same housing as an external wireless device, in a separate housing in the same room or building as the wireless implantable device, in a remote location from the wireless implantable device and the external wireless device (e.g., a different building, city, country), any combinations thereof, and the like. Processing of data or information related to the wireless system may be performed in real-time as the data (e.g., feedback signal data, physiological data) is received or recorded, or it may be performed at a different time.

E. Wireless Signals

A wireless signal as used herein may generally refer to any wireless signal exchanged between two devices such as a wireless implantable device and an external wireless device. In some variations, a wireless signal may comprise one or more of wireless power or power signal, a downlink data signal, a downlink command, an interrogation signal, a feedback signal, a link scan signal, an uplink data signal, an uplink command, a reflection signal, a backscatter signal, and the like.

a. Feedback Signal

A feedback signal may generally refer to any signal received by a wireless device (e.g., an external wireless device) from another wireless device (e.g., a wireless implantable device). In some variations, a feedback signal may be generated in response to another signal (e.g., interrogation signal). In some variations, a wireless device (e.g., a wireless implantable device) may be configured to transmit one or more feedback signals without being interrogated by another wireless device. For instance, a wireless implantable device may be configured to periodically transmit feedback signals, which may also be referred to as beacon signals in some variations.

In some variations, a feedback signal may be generated using one or more of mechanical waves (e.g., ultrasonic, acoustic, vibrational), magnetic fields (e.g., inductive), electric fields (e.g., capacitive), electromagnetic waves (e.g., RF, optical), galvanic coupling, surface waves, and the like. In some variations, a feedback signal may be generated in the form of a continuous wave (CW) signal or a pulsed wave (PW) signal. In some variations, the feedback signal may be generated using any known digital or analog modulation techniques such as ASK, FSK, PSK, AM, FM, PM, pulse modulation, PAM, PIMD, PPM, PCM, PDM, and the like. In some variations, an ultrasonic feedback signal may comprise a carrier frequency of between about 20 kHz to about 20 MHZ. In some variations, an ultrasonic feedback signal pulse may comprise a pulse duration between about 1 us to about 1 ms.

In some variations, a feedback signal may comprise one or more pulses. For example, a wireless implantable device may be configured to transmit a single ultrasonic pulse as a feedback signal (e.g., comprising one or more cycles of a carrier frequency), or it may periodically transmit a plurality of ultrasonic pulses. Such an ultrasonic pulse may be used by an external wireless device for triangulation or localization of the wireless implantable device and/or for estimating a link gain between the external wireless device and the wireless implantable device, as described in more detail herein. In some variations, a feedback signal may comprise a plurality of cycles of a carrier frequency. For example, the duration of a feedback signal may be greater than about 5 cycles of a carrier frequency of the feedback signal. In some variations, a feedback signal may comprise a pulse signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, one or more cycles of a carrier frequency of the pulse signal, combinations thereof, and the like. In some variations, the pulse signal may comprise sinusoidal cycles of a carrier frequency. In some variations, the pulse signal may comprise one or more of a 2-level square wave, a 3-level square wave, a 5-level square wave, a multi-level square wave, combinations thereof, and the like. In some variations, the feedback signal may be generated by a multi-level pulser circuit (e.g., a 3-level pulser) of the first device.

In some variations, a feedback signal may comprise data encoded using a modulation technique (e.g., digital modulation). For example, in some variations, a wireless implantable device may encode onto a feedback signal, one or more of the following including, but not limited to, the power or voltage received by one or more transducers of the wireless implantable device (e.g., after digitization of the power or voltage), the wireless implantable device's battery and/or capacitor voltage, energy state of the wireless implantable device, stored energy on a power source of the wireless implantable device (e.g., battery, capacitor), battery charging current, DC voltage generated by the wireless implantable device's power circuit, combinations thereof, and the like. As another example, in some variations, a wireless implantable device may encode a unique identification (ID) number or code onto a feedback signal. In some variations, a feedback signal may encode a time delay. For example, in some variations, a feedback signal may encode the time delay (e.g., after digitization) between receipt of an interrogation and/or power signal from an external wireless device and transmission of the feedback signal to the external wireless device.

In some variations, a feedback signal may comprise one or more of a reflection signal and a backscatter signal. These signals may be generated upon reflection or backscattering of an interrogation signal, or any other signal transmitted by an external wireless device, off one or more wireless implantable devices and/or one or more tissue structures (such as ribs, lungs, boundaries between two tissue types, and the like). Reflections from a wireless implantable device may comprise one or more reflections from one or more of the housing, coating or encapsulation of the wireless implantable device, the wireless implantable device transducer (e.g., ultrasonic transducer), surface of a wireless implantable device (e.g., front, back, side, outer, inner), any part of a wireless implantable device, combinations thereof, and the like. In some variations, the reflection signals may comprise ultrasonic reflection signals generated upon reflection of an ultrasonic signal transmitted by a sub-array of the external wireless device into tissue.

b. Link Scan Signal

A link scan signal may generally refer to any signal transferred in a wireless link that may be processed to determine a property of the wireless link. A link scan signal may be transmitted by any device of a wireless system. For example, a link scan signal may be transmitted by one or more of a wireless implantable device and an external wireless device. For example, a link scan signal may be an impulse signal transmitted by a wireless implantable device and received by an external wireless device. A processor of the external wireless device may be configured to process the received impulse signal to determine an impulse response of the wireless link or system.

In some variations, a link scan signal may comprise parameters or properties (e.g., signal modality, type, modulation, and the like) similar to those described for the feedback signal. In some variations, a link scan signal may be generated using one or more of mechanical waves (e.g., ultrasonic, acoustic, vibrational), magnetic fields (e.g., inductive), electric fields (e.g., capacitive), electromagnetic waves (e.g., RF, optical), galvanic coupling, surface waves, and the like. In some variations, a link scan signal may comprise one or more of an impulse signal, a pulse signal, a feedback signal, a predetermined digital code and a continuous-wave signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, one or more cycles of a carrier frequency of the pulse signal, combinations thereof, and the like. In some variations, a pulse signal may comprise sinusoidal cycles of a carrier frequency. In some variations, a pulse signal may comprise one or more of a 2-level square wave, a 3-level square wave, a 5-level square wave, a multi-level square wave, combinations thereof, and the like. In some variations, the link scan signal may be generated by a multi-level pulser circuit (e.g., a 3-level pulser) of the first device. In some variations, an ultrasonic link scan signal may comprise a carrier frequency of between about 20 kHz to about 20 MHz.

In some variations, a link scan signal may comprise data encoded using a modulation technique (e.g., digital modulation). In some variations, a link scan signal may comprise one or more of a reflection signal and a backscatter signal. For example, a link scan signal may comprise a reflection signal from a wireless implantable device corresponding to a signal transmitted by an external wireless device into tissue.

c. Data Signal

A data signal may generally refer to any signal transferred in a wireless link for data communication. A data signal may be transmitted by any device of a wireless system. For example, a data signal may be transmitted by one or more of a wireless implantable device and an external wireless device. A data signal may comprise one or more of an uplink data signal and a downlink data signal. An uplink data signal may refer to a data signal from a wireless implantable device to an external wireless device. A downlink data signal may refer to a data signal from an external wireless device to a wireless implantable device.

In some variations, a data signal may comprise parameters or properties (e.g., signal modality, type, modulation, and the like) similar to those described for the feedback signal. In some variations, a data signal may be generated using one or more of mechanical waves (e.g., ultrasonic, acoustic, vibrational), magnetic fields (e.g., inductive), electric fields (e.g., capacitive), electromagnetic waves (e.g., RF, optical), galvanic coupling, surface waves, and the like. In some variations, a data signal may be generated in the form of a continuous wave (CW) signal or a pulsed wave (PW) signal. In some variations, the data signal may comprise one or more of digital data and analog data. In some variations, the data signal may be generated using any known digital or analog modulation techniques such as ASK, FSK, PSK, AM, FM, PM, pulse modulation, PAM, PIMD, PPM, PCM, PDM, and the like. In some variations, an ultrasonic data signal may comprise a carrier frequency of between about 20 kHz to about 20 MHz. In some variations, a data bit of a data signal (e.g., an ultrasonic data signal) may comprise a pulse duration (or bit duration) between about 1 us to about 1 ms. In some variations, a data signal may comprise one or more of a reflection signal and a backscatter signal. For example, a data signal may comprise backscatter communication.

In some variations, a data signal may encode one or more of a physiological parameter (e.g., information about a physiological parameter sensed by a wireless implantable device), a parameter of a wireless device (e.g., voltage of an energy storage device of a wireless implantable device, a frequency of a wireless device, an ID of a wireless device, and the like), a parameter of a wireless link (e.g., link gain), data generated by a processor of a wireless device (e.g., feedback signal data), data generated by a user (e.g., a user command), a wireless command or instruction, combinations thereof, and the like.

II. Methods

Described herein are methods for exchanging wireless signals in a wireless system, using any of the systems and devices described herein. Generally, a wireless system or device may implement one or more of the methods described herein, or any sub-set of the one or more methods described herein, or a combination of methods or sub-sets thereof. One or more methods described here, or steps therein, may be applied to a plurality of wireless implantable devices and/or wireless monitors.

Wireless signals exchanged in a wireless system comprising heterogeneous media (e.g., ribs, lungs, muscle, and the like) may experience reflections off different objects or structures in the medium. Such reflections may cause undesired destructive and/or constructive interference of wireless signals due to multipath interference. Solutions are provided herein for mitigating and/or accounting for the effect of multipath interference in order to efficiently and/or reliably transfer wireless signals (e.g., power, data, commands, and the like) in a wireless system.

In some variations, exchanging wireless signals in a wireless system may be facilitated by transmitting a feedback signal from a first device of the wireless system to a second device of the wireless system. In some variations, a method of exchanging wireless signals in a wireless system may comprise one or more of the following steps, including but not limited to, transmitting a feedback signal with a first duration from a first device of the wireless system to a second device of the wireless system, receiving the feedback signal for a second duration using one or more transducer elements of a transducer array of the second device, processing the feedback signal received in the second duration using one or more transducer elements of the transducer array to generate feedback signal data using a processor of the second device, determining a transducer array configuration of the second device based at least in part on the feedback signal data using the processor of the second device, and exchanging one or more wireless signals with the first device using the transducer array configuration of the second device.

In some variations, a method of exchanging wireless signals in a wireless system may comprise one or more of the following steps, including but not limited to, transmitting a feedback signal from a first device of the wireless system to a second device of the wireless system, receiving the feedback signal using a first transducer array of the second device, extracting one or more portions of the received feedback signals, received by one or more transducer elements of the first transducer array of the second device, using a processor of the second device, processing the extracted one or more portions of the received feedback signals using the processor of the second device to generate feedback signal data, determining a second transducer array configuration of the second device based at least in part on the feedback signal data, and exchanging one or more wireless signals with the first device using the second transducer array configuration of the second device.

In some variations, exchanging wireless signals in a wireless system may be facilitated by transmitting a link scan signal from a first device of the wireless system to a second device of the wireless system. In some variations, a method of exchanging wireless signals in a wireless system may comprise one or more of the following steps, including but not limited to, transmitting a link scan signal from a first device of a wireless system to a second device of the wireless system, receiving the link scan signal using a first transducer array of the second device, processing the received link scan signals, received by one or more transducer elements of the first transducer array of the second device, using a processor of the second device to generate link scan signal data, determining a second transducer array configuration of the second device based at least in part on the link scan signal data, and exchanging one or more wireless signals with the first device using the second transducer array configuration of the second device.

In some variations, exchanging wireless signals in a wireless system may be facilitated by transmitting both a link scan signal and a feedback signal from a first device of the wireless system to a second device of the wireless system. In some variations, a method of exchanging wireless signals in a wireless system may comprise one or more of the following steps, including but not limited to, transmitting a link scan signal and a feedback signal from a first device of the wireless system to a second device of the wireless system, receiving the link scan signal and the feedback signal using a first transducer array of the second device, processing the received link scan signals and the received feedback signals, received by one or more transducer elements of the first transducer array of the second device, using a processor of the second device to generate feedback signal data, determining a configuration of a second transducer array of the second device based at least in part on the feedback signal data, and exchanging one or more wireless signals with the first device using the configuration of the second transducer array of the second device.

Also described herein are methods of exchanging wireless signals based on defocusing an acoustic beam. Methods of closed-loop powering to target a requisite voltage and/or power level at a first device when transmitting wireless power to it from a second device, are also described herein.

Also described herein are methods of wireless data communication between two or more devices of a wireless system. In some variations, wireless data communication between two wireless devices may utilize a link scan signal. In some variations, a method of decoding a data signal in a wireless system may comprise the following steps, including but not limited to, transmitting a link scan signal and a first data signal from a first device of the wireless system to a second device of the wireless system, receiving the link scan signal and the first data signal using one or more transducer elements of the second device, processing the received link scan signal and the received first data signal using a processor of the second device to generate a second data signal, and decoding the first data signal based at least in part on the second data signal.

In some variations, wireless data communication between a first device and a second device of a wireless system may utilize selection of one or more transducer elements of the second device. In some variations, a method of decoding data signals in a wireless system may comprise the following steps, including but not limited to, transmitting a link scan signal and a first data signal from a first device of the wireless system to a second device of the wireless system, receiving the link scan signal and the first data signal using one or more transducer elements of the second device, processing one or more of the received link scan signal and the received first data signal using a processor of the second device to select one or more transducer elements of the second device, and decoding the first data signal based at least in part on the selected one or more transducer elements of the second device.

In some variations, wireless data communication between two wireless devices may utilize a pre-distorted data signal. In some variations, a method of decoding signals in a wireless system may comprise the following steps, including but not limited to, transmitting a link scan signal from a first device of the wireless system to a second device of the wireless system, receiving the link scan signal using one or more transducer elements of the second device, processing the received link scan signal using a processor of the second device to generate link scan signal data, generating a pre-distorted data signal based on the link scan signal data using the processor of the second device, transmitting the pre-distorted data signal from the second device to the first device, receiving the pre-distorted data signal using one or more transducer elements of the first device, and processing the received pre-distorted data signal using a processor of the first device to generate decoded data.

Also described herein are methods of calibrating a wireless system. In some variations, a method of calibrating a wireless system may comprise the following steps, including but not limited to, transmitting one or more test signals comprising one or more carrier frequencies from a first device of the wireless system to a second device of the wireless system, receiving the one or more test signals using the second device, processing the one or more received test signals using a processor of the second device to generate test signal data, determining one or more selected carrier frequencies using the processor of the second device based at least in part on the test signal data, transmitting one or more wireless commands from the second device to the first device comprising information corresponding to the one or more selected carrier frequencies, and storing information corresponding to the one or more selected carrier frequencies in a memory of the first device.

A. Exchanging Wireless Signals with a Wireless Device

In some variations, beamforming may be performed in a wireless system for establishing a reliable and/or efficient wireless link between two or more wireless devices. In some variations, a wireless signal, such as a feedback signal, propagating wirelessly from a first device of a wireless system may be received by a second device of the wireless system. Such a received signal may be processed by a processor of the second device in order to determine a transducer configuration of the second device for exchanging wireless signals with the first device. For example, the transducer configuration may comprise a set of elements of a transducer array of the second device, and their corresponding signal strengths and delays or phases, for transmitting wireless power to the first device. The determination of such a transducer configuration may be challenging in wireless links or systems that experience multipath interference due to reflections of wireless signals propagating in the wireless link off heterogeneous media and structures. For example, ultrasound signals propagating in the thorax may experience multipath interference due to reflection and/or scattering of ultrasonic waves off ribs, lungs and/or other tissue boundaries. Since conventional ultrasonic beamforming techniques may not account for multipath interference, using such techniques for delivering wireless power or energy to a wireless implantable device may result in diminished total power or energy delivery due to potential destructive interference of ultrasonic waves reaching the wireless implantable device from one or more reflectors in the medium. Solutions are provided herein to overcome such a challenge.

a. Exchanging Wireless Signals Based on a Feedback Signal

In some variations, wireless devices in a wireless system may exchange wireless signals based on a feedback signal propagating from a first device of the wireless system to a second device of the wireless system.

Figure 3:
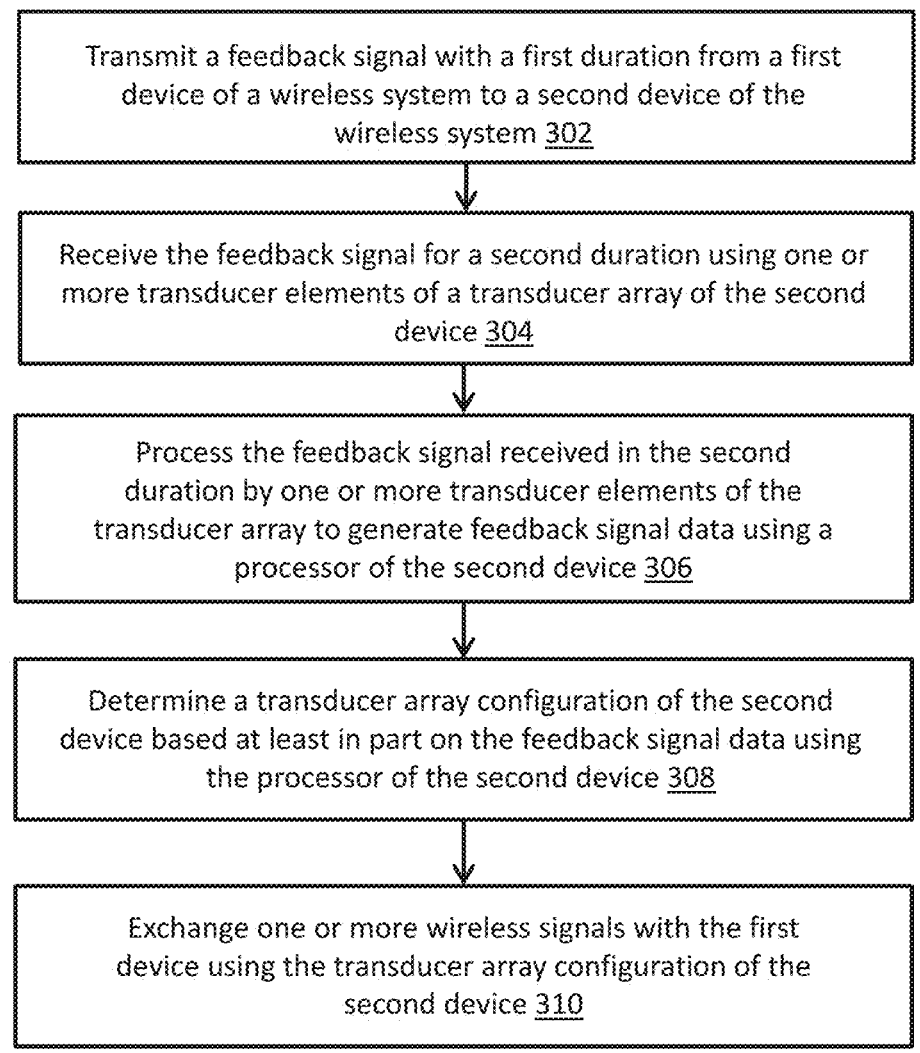
FIG. 3 is a flowchart of an illustrative variation of a method of exchanging wireless signals with a device based on a feedback signal.

FIG. 3 is a flowchart that generally describes a variation of a method of exchanging wireless signals with a device based on a feedback signal (300). In some variations, determining a transducer array configuration of the second device based at least in part on feedback signal data (e.g., that characterizes a wireless link between the first device and the second device), may allow focused wireless signals (e.g., ultrasonic waves) to be transmitted by the second device, thereby resulting in a reliable and/or efficient wireless link between the second device and the first device. The method (300) may comprise the steps of transmitting a feedback signal with a first duration from a first device of the wireless system to a second device of the wireless system (302), receiving the feedback signal for a second duration using one or more transducer elements of a transducer array of the second device (304), processing the feedback signal received in the second duration by one or more transducer elements of the transducer array to generate feedback signal data using a processor of the second device (306), determining a transducer array configuration of the second device based at least in part on the feedback signal data using the processor of the second device (308), and exchanging one or more wireless signals with the first device using the transducer array configuration of the second device (310).

In some variations, the feedback signal may comprise one or more analog pulses. In some variations, processing the feedback signal may comprise extracting analog features of the feedback signal such as one or more of amplitude, phase, time delay, time of arrival, duration, number of cycles, frequency, power, energy, combinations thereof, and the like.

In some variations, the received feedback signal may be processed on a subset of transducer elements (e.g., some or all) on which the feedback signal is received. In some variations, the transducer elements selected to process the received feedback signals may be predetermined. In some variations, the transducer elements selected to process the received feedback signals may be selected based on one or more properties of one or more of the received feedback signals, other signals in the wireless system, properties of the transducer elements, combinations thereof, and the like. For instance, the transducer elements selected to process the received feedback signals may be selected based on a signal strength of the received feedback signal, a signal-to-noise ratio of the received feedback signal, an energy of the received feedback signal in one or more frequency bands, a predetermined apodization of the transducer element, a moving mean of the feedback signal amplitude, a signal strength of an interferer, a signal strength of multipath interference, and a multipath time. Apodization may refer to relative amplitude weightings applied to different transducer elements of a transducer array for transmitting and/or receiving wireless signals. For example, a transducer element having an apodization value of 0.7 may be configured to transmit a signal amplitude that is about 70%, or equivalently a power level that is about 49%, relative to another transducer element having an apodization value of 1.0. In some variations, multipath time may refer to a time duration over which multipath reflections or multipath interference in a wireless link may dissipate below a predetermined threshold (e.g., a predetermined power level).

In some variations, the second duration may be greater than the first duration. In some variations, the second duration may be predetermined based on one or more of multipath propagation in the wireless link, multipath time, signal attenuation in the medium, propagation speed of wireless signals in the medium, calibration of the system by transmitting a signal through the system and measuring the time required for multipath echoes to dissipate, combinations thereof, and the like. In some variations, the second duration may be determined by the processor of the second device based on a property of the received feedback signal (e.g., by measuring the time required for multipath echoes in the received feedback signal to dissipate). In some variations, the second duration of the received feedback signal may be smaller than the first duration of the transmitted feedback signal. For instance, the transmitted feedback signal may comprise a pulse signal comprising a plurality of cycles of a carrier frequency and the second duration of the received feedback signal may comprise a portion of the pulse signal comprising one or more cycles with a settled signal amplitude (e.g., an amplitude where multipath echoes have dissipated).

In some variations, the method (300) may comprise detecting an onset (e.g., rising edge, time of arrival) of the received feedback signal on one or more transducer elements of the transducer array using one or more of envelope detection, predetermined timing, coherent detection (e.g., using mixing), comparison of the received feedback signal amplitude to a threshold level, combinations thereof, and the like. In some variations, onset detection may comprise using one or more of envelope detection, predetermined timing (e.g., based on the time at which the first device may transmit the feedback signal and signal propagation delay from the first device to the second device), coherent detection, and comparison of the received feedback signal amplitude to a threshold level (e.g., a predetermined threshold).

In some variations, the feedback signal data may comprise one or more of an absolute amplitude or magnitude, a relative amplitude or magnitude, an absolute signal strength, a relative signal strength, signal energy in one or more frequency bands, an apodization, an absolute phase, a relative phase, an absolute time delay, a relative time delay, an absolute time of arrival, a relative time of arrival, a frequency, a time duration, number of cycles, an absolute signal-to-noise ratio, a relative signal-to-noise ratio of the feedback signal received within the second duration by one or more transducer elements of the transducer array, combinations thereof, and the like. For instance, in some variations, times of arrival of the received feedback signals on one or more transducer elements may comprise detecting an absolute timing of a rising edge of the received feedback signal, or a timing of a rising edge of the received feedback signal relative to a reference transducer element. In some variations, the reference transducer element may be determined based on one or more of the received feedback signal's amplitude, energy, signal-to-noise ratio or signal-to-interference ratio, an apodization of the transducer element, combinations thereof, and the like. For instance, the reference transducer element may be the transducer element which receives the strongest amplitude or SNR of the feedback signal.

In some variations, the transducer array configuration may comprise one or more of a selection of transducer elements, an apodization, a signal strength, a voltage level, a current level, a pulse width, pulse width modulation, a duty cycle of a signal, a phase, a time delay, a frequency, a transmit duration applied to one or more transducer elements of the transducer array for transmitting wireless signals to the first device, combinations thereof, and the like. In some variations, the transmitted wireless signals may comprise one or more of power, data, commands, one or more other signals (e.g., a pulse), combinations thereof, and the like. In some variations, the second device may comprise one or more pulser circuits to drive the one or more transducer elements of the transducer array for transmitting wireless signals. In some variations, the output or transmit signal of the pulser circuit may comprise one or more signal levels (e.g., a 2-level pulser output or a square wave, 3-level pulser output, 5-level pulser output, combinations thereof, and the like). In some variations, the multi-level pulser output may comprise a pulse width or a duty cycle which may be modulated (e.g., pulse width modulation) to modulate the transmit power.

In some variations, a transducer array configuration may comprise a set of parameters (e.g., transducer element phases) based on a parameter (e.g., phases) of the feedback signal. For example, the phases applied to the one or more transducer elements of the transducer array for transmitting wireless signals to the first device may be based on one or more of the relative phases of the received feedback signal in the second duration at a predetermined frequency and the time of arrival of the feedback signal received on the one or more transducer elements. Additionally or alternatively, the time delays applied to the one or more transducer elements of the transducer array for transmitting wireless signals to the first device may be based on one or more of the relative phases of the received feedback signal in the second duration at a predetermined frequency and the time of arrival of the feedback signal received on the one or more transducer elements. In some variations, the predetermined frequency may comprise one or more of a carrier frequency of the feedback signal, a harmonic of the carrier frequency, a sub-harmonic of the carrier frequency, yet another frequency in the frequency band of the received feedback signal, combinations thereof, and the like. In some variations, the time delay applied to a transducer element may comprise the sum of the relative time of arrival of the feedback signal (e.g., relative to a reference transducer element) rounded off to a period of the carrier frequency of the feedback signal and the time delay or phase corresponding to the relative phase of the received feedback signal (e.g., relative to a reference transducer element) received in the second duration at the carrier frequency of the feedback signal. For instance, this may facilitate alignment of the rising and/or falling edges of wireless signals (e.g., ultrasonic pressure waves) as well as the steady-state phases of the wireless signals received by a transducer element of the first device from different transducer elements of the second device. In some variations, aligning the rising and/or falling edges may allow shortening bit durations of OOK-modulated downlink data bits transmitted by a second device (e.g., an external device) to a first device (e.g., an implantable medical device), thereby, allowing higher data rates and faster data communication. In some variations, the relative phases of the received feedback signal in the second duration at the predetermined frequency may be the relative phases of the portion of the feedback signal with a settled amplitude (e.g., where multipath reflections have dissipated below a predetermined threshold, the amplitude within about 5% of its steady-state value). In some variations, the transmit phases or time delays may be applied using one or more of a number of clock cycles, a delay line, a digitally controlled phase or time delay, an analog phase or time delay, combinations thereof, and the like. In some variations, the transmit phases may be wrapped (e.g., limited to [0, $2\pi$) or [$-\pi$, $\pi$) radians). In some variations, the transmit phases may be unwrapped.

In some variations, the received feedback signal may comprise a time duration with a settled amplitude. In some variations, the first duration of the transmitted feedback signal may be greater than a multipath time of the wireless link (e.g., to allow multipath reflections to subside resulting in a settled amplitude of the received feedback signal). In some variations, the first duration of the transmitted feedback signal may be greater than about 5 cycles of the carrier frequency of the feedback signal. In some variations, the feedback signal may comprise one or more of an impulse signal and a pulse signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, one or more cycles of a carrier frequency of the pulse signal, combinations thereof, and the like.

In some variations, processing the feedback signal or determining the transducer array configuration of the second device may comprise one or more of a time domain analysis, a frequency domain analysis, an interpolation analysis, combinations thereof, and the like. In some variations, the time domain analysis may comprise one or more of cross-correlation and time reversal. For instance, the feedback signal (or a portion of the feedback signal with a settled amplitude) received on a transducer element may be cross-correlated with the feedback signal (or a portion of the feedback signal with a settled amplitude) received on another transducer element in order to determine their relative phase difference or time delay. In some variations, the relative phase difference or time delay may be reversed and applied to the transducer elements for transmitting wireless signals to the first device (e.g., to accomplish focusing of power or continuous-wave signals at the transducer of the first device).

In some variations, the frequency domain analysis may comprise computing one or more of a Fourier transform, a discrete Fourier transform (DFT), a discrete-time Fourier transform (DTFT), combinations thereof, and the like, at one or more predetermined frequencies. In some variations, computing one or more of the Fourier transform, the discrete Fourier transform (DFT) and the discrete-time Fourier transform (DTFT) at the one or more predetermined frequencies may comprise using one or more of a fast Fourier transform (FFT) algorithm, a Goertzel algorithm, combinations thereof, and the like. In some variations, applying the Goertzel algorithm at one or more predetermined frequencies may be computationally more efficient compared to determining a Fourier transform or DFT in a wide frequency band. In some variations, the one or more predetermined frequencies may be based on one or more feedback signal frequencies (e.g., a carrier frequency of the feedback signal). In some variations, determining the one or more predetermined frequencies may be based on one or more of a time domain analysis and a frequency domain analysis of the feedback signal received in one or more of the first duration, the second duration and a third duration by one or more transducer elements of the transducer array. For instance, the third duration may comprise one or more cycles of the carrier frequency of the received feedback signal. In some variations, an onset (e.g., rising edge) of the feedback signal pulse received on one or more transducer elements may be detected and the third duration may be determined based on one or more of the onset time (e.g., timing of the rising edge of the feedback signal pulse) and a predetermined pulse width of the feedback signal. For instance, the third duration may start at the onset time or a fixed time offset after the onset time (e.g., one or more cycles of the carrier frequency after the onset time) and end after one or more cycles (e.g., 5 cycles) of the carrier frequency of the received feedback signal.

In some variations, the interpolation analysis may comprise interpolating one or more of feedback signal data and the transducer array configuration from one or more transducer elements to other one or more transducer elements (e.g., neighboring transducer elements). For instance, such interpolation analysis may be based upon one or more interpolation techniques such as spline interpolation, linear interpolation, cubic interpolation, combinations thereof, and the like. In some variations, predetermined spatial locations of the transducer elements may be used for interpolation (e.g., compute transmit phases based on path length differences for feedback signal propagation from the first device to different transducer elements of the second device). In some variations, interpolation may allow transmitting wireless signals on one or more transducer elements that were not configured to receive the feedback signal or process the received feedback signal.

In some variations, determining a transducer array configuration of the second device may comprise using at least one of the feedback signal data and a predetermined power of the transmitted feedback signal to determine one or more of a link efficiency and transmit power for transmitting wireless signals to the first device. For instance, a method of closed-loop powering as described herein may be used to determine one or more of a link efficiency (e.g., uplink and/or downlink link efficiency) and transmit power for transmitting wireless signals from the second device to the first device.

In some variations, the one or more wireless signals exchanged with the first device may comprise the same or different one or more frequencies compared to the one or more frequencies of the feedback signal. For instance, the feedback signal may comprise a carrier frequency $f_1$, and a frequency domain analysis of the received feedback signal may be performed to generate feedback signal data (e.g., magnitude, phase, and the like, of the received feedback signal) at a frequency $f_2$, where $f_1$ may not be not equal to $f_2$. In some variations, the feedback signal data may be generated at the frequency $f_1$ and/or a frequency $f_2$, and a transducer array configuration (e.g., transmit phase or time delay, apodization, transmit signal strength, transmit signal pulse width, etc.) may be determined at a frequency $f_2$ (e.g., by scaling magnitudes and phases at frequency $f_1$ to frequency $f_2$), where $f_1$ may not be equal to $f_2$ (e.g., $f_2$ may be a harmonic of $f_1$, a sub-harmonic of $f_1$ or an arbitrary frequency relative to $f_1$).

In some variations, the transducer elements configured to receive the feedback signal and the transducer array configuration used to exchange wireless signals with the first device may comprise one or more common transducer elements. In some variations, the transducer elements used for receiving the feedback signal and the transducer array configuration used to exchange wireless signals with the first device may comprise different transducer elements. In some variations, interpolation (e.g., based on neighboring transducer elements) may be used to determine the configuration of one or more transducer elements used for exchanging wireless signals with the first device if the one or more transducer elements were not used for receiving or processing the feedback signal.

In some variations, the first device may comprise an implantable medical device, and the second device may comprise an external wireless device configured to be disposed physically separate from the first device. In some variations, the first device may comprise an external wireless device, and the second device may comprise an implantable medical device configured to be disposed physically separate from the first device.

In some variations, the method (300) may comprise transmitting the feedback signal or a plurality of feedback signals from the first device at one or more predetermined repetition intervals. In some variations, the predetermined repetition interval may correspond to a time duration over which the wireless link may be quasi-static (e.g., the time duration over which a link efficiency may vary by less than about 3 dB) or the first device may be relatively stationary with respect to the first device. In some variations, the first duration of the transmitted feedback signal may be the same or different in different repetition intervals. In some variations, the second duration of the received feedback signal may be the same or different in different repetition intervals. In some variations, the method (300) may comprise transmitting a wireless command from the second device to the first device and transmitting the feedback signal from the first device to the second device in response to receiving the wireless command. In some variations, the wireless command may comprise one or more of a wireless signal, a pulse signal, a plurality of pulse signals, a signal with encoded data bits (e.g., using on-off keying (OOK) modulation), combinations thereof, and the like. In some variations, the transmitted feedback signal may comprise a reflection signal or a backscatter signal in response to a wireless signal transmitted by the second device to the first device. In some variations, the transmitted feedback signal may comprise one or more of an ultrasonic signal, an acoustic signal, a vibrational signal, a radio-frequency signal, an electromagnetic signal, a magnetic signal, an electric signal, an optical signal, combinations thereof, and the like. In some variations, the transmitted feedback signal may be an ultrasonic or acoustic signal with a carrier frequency between about 20 kHz to about 20 MHz. In some variations, the first duration of the transmitted feedback signal may be between about 1 us to 1 ms (e.g., comprising a pulse signal with one or more cycles of a carrier frequency). In some variations, the second duration of the received feedback signal may be between about 1 us to 100 ms (e.g., 500 us to capture multipath reflections of the transmitted feedback signal pulse).

In some variations, the method (300) may comprise transmitting one or more data signals from the first device to the second device. In some variations, the method (300) may further comprise selecting one or more transducer elements (e.g., some or all) of the transducer array of the second device for processing the one or more data signals using the processor of the second device. In some variations, selecting the one or more transducer elements of the transducer array of the second device may be based on one or more of a signal strength of the received feedback signal, a signal-to-noise ratio of the received feedback signal, an energy of the received feedback signal in one or more frequency bands, an apodization of the transducer element, a moving mean of the feedback signal amplitude, a signal strength of an interferer, a signal strength of multipath interference, a multipath time, combinations thereof, and the like. In some variations, the method (300) may comprise transmitting one or more data signals from the second device to the first device.

Figure 4:
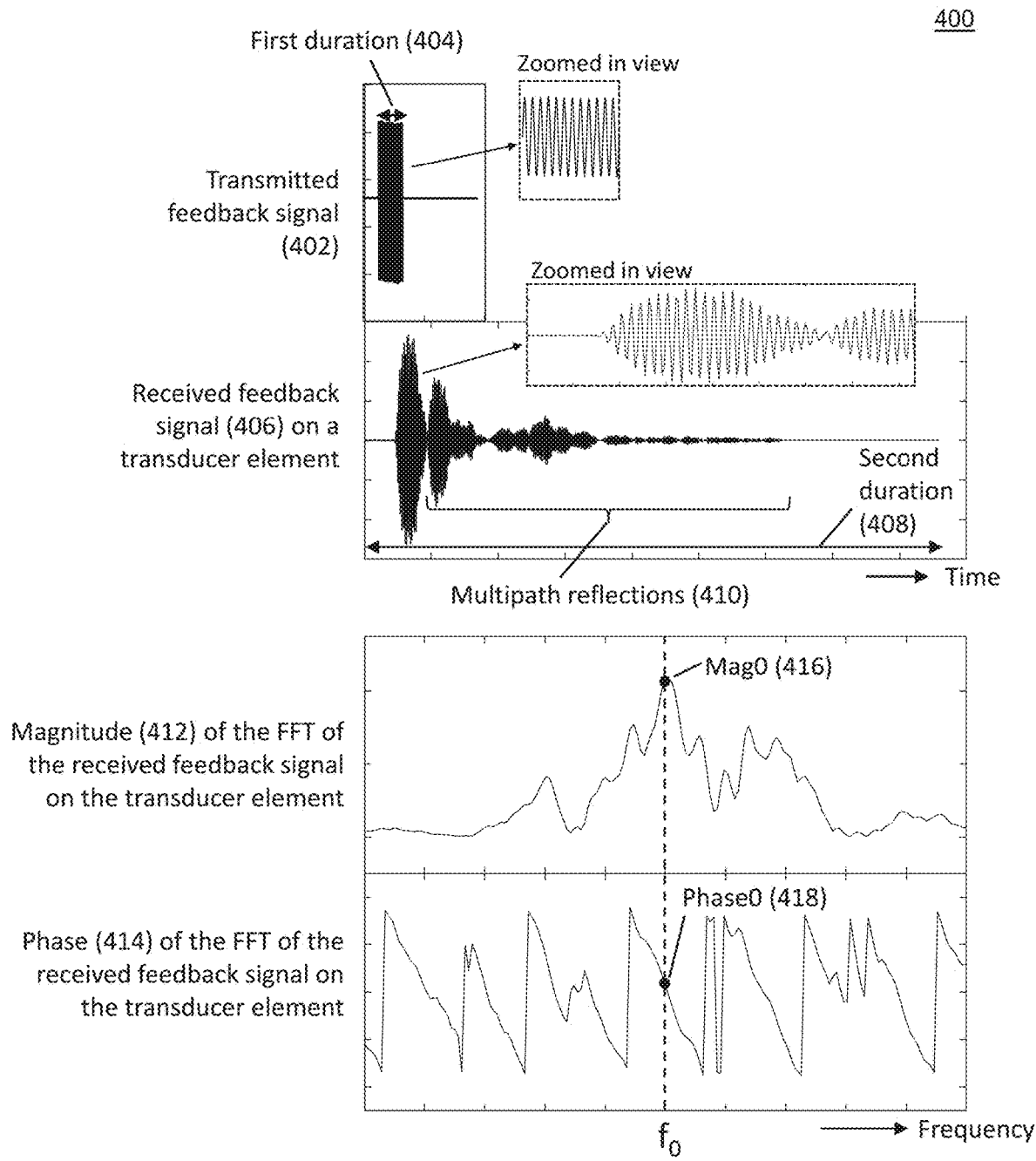
FIG. 4 is a timing diagram of an illustrative variation of a feedback signal and feedback signal data.

FIG. 4 shows a timing diagram of an illustrative variation of a feedback signal used in a method of exchanging wireless signals with a wireless device (400). As shown, a transmitted feedback signal (402) from a first device (e.g., a wireless implantable device) may comprise a first duration (404). Upon wireless propagation through the medium between the first device and the second device (e.g., heterogeneous tissue structures), the transmitted feedback signal (402) may be subject to multipath interference. The feedback signal (406) received by a transducer element during a second duration (408) is also shown. The feedback signal (406) received during the second duration (408) may comprise multipath reflections (410) due to the multipath interference in the wireless link. In some variations, the second duration (408) may be greater than a time duration required for multipath reflections (410) or echoes to dissipate (e.g., for the strength of multipath reflections to dissipate by a certain level, such as 30 dB, below the strength of the first received feedback signal pulse, or below a predetermined threshold level). A processor of the second device may be configured to process the received feedback signal (406) in the frequency domain. For instance, the processor may be configured to compute one or more of a magnitude (412) and a phase (414) of the Fourier transform of the received feedback signal (406) in the second duration (or in a third duration obtained by zero padding the received feedback signal), using one or more of an FFT algorithm and a Goertzel algorithm at one or more predetermined frequencies. In some variations, the processor may be configured to generate feedback signal data comprising one or more of a magnitude value Mag0 (416), and a phase value Phase0 (418), of the received feedback signal (406) at one or more predetermined frequencies, such as a carrier frequency of the transmitted feedback signal denoted by $f_0$ in FIG. 4. As an example, feedback signal data corresponding to the received feedback signals of three transducer elements of the transducer array may comprise magnitudes of [85.8, 61.5, 32.0] in arbitrary units, and phases of [19.3, −89.6, 72.5] in degrees. Based on the feedback signal data, the processor may determine the transducer array configuration comprising the apodizations or transmit signal strengths of [1.00, 0.72, 0.37] in arbitrary units, and transmit phases of [0, −108.9, 53.2] degrees for transmitting wireless signals on the three transducer elements to the first device. The apodizations may be computed by normalizing the magnitudes to the maximum magnitude. The transmit phases may be computed as phase differences relative to a reference transducer element.

Figure 5:
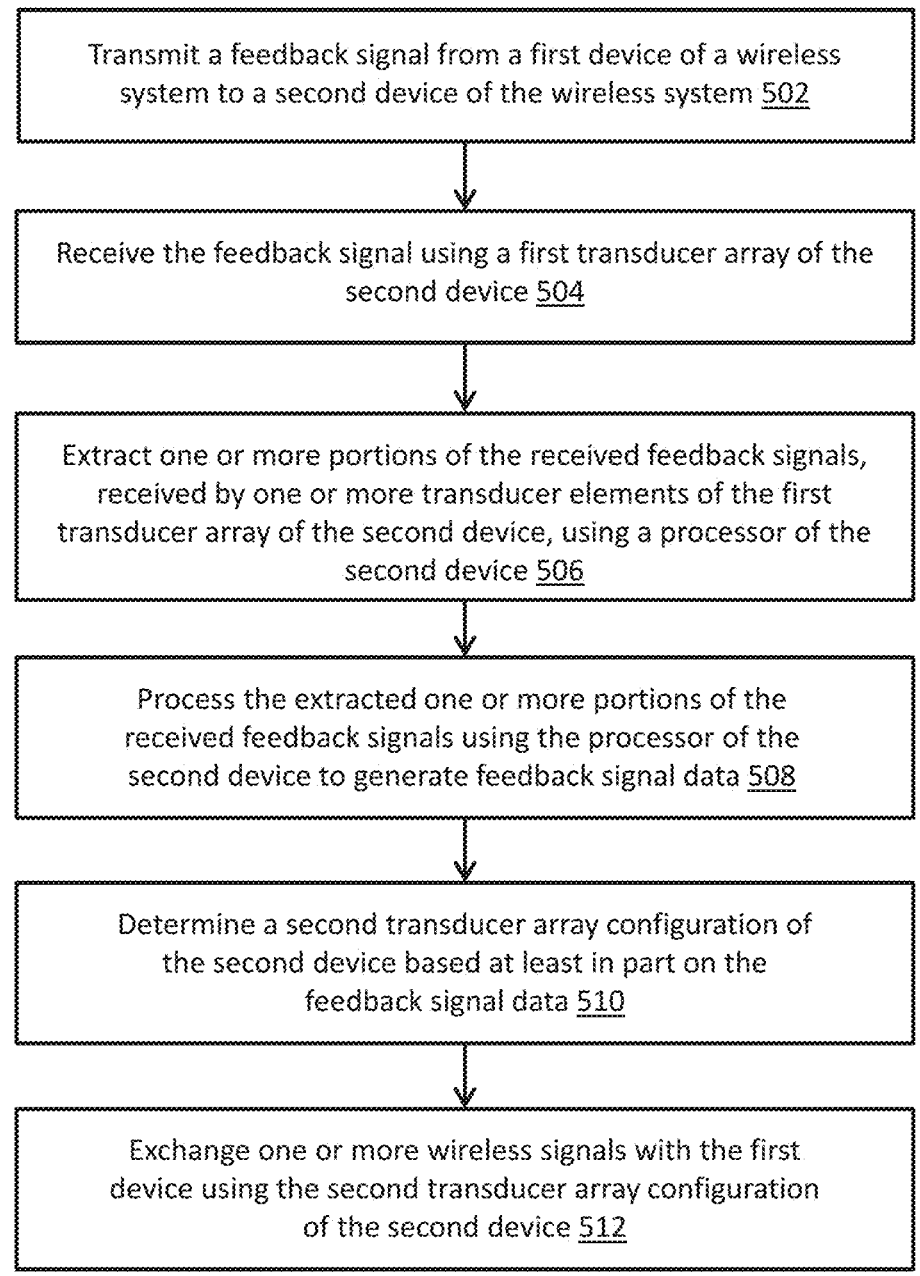
FIG. 5 is a flowchart of an illustrative variation of another method of exchanging wireless signals with a device based on a feedback signal.

FIG. 5 is a flowchart that generally describes a variation of a method of exchanging wireless signals with a device based on a feedback signal (500). The method (500) may comprise the steps of transmitting a feedback signal from a first device of a wireless system to a second device of the wireless system (502), receiving the feedback signal using a first transducer array of the second device (504), extracting one or more portions of the received feedback signals, received by one or more transducer elements of the first transducer array of the second device, using a processor of the second device (506), processing the extracted one or more portions of the received feedback signals using the processor of the second device to generate feedback signal data (508), determining a second transducer array configuration of the second device based at least in part on the feedback signal data (510), and exchanging one or more wireless signals with the first device using the second transducer array configuration of the second device (512). The feedback signal, the transducer array, the processor, the transducer array configuration, the feedback signal data, and the wireless signals, as described herein, are applicable to any of the methods described herein. In some variations, the extracted one or more portions of the received feedback signal may have a duration less than a duration of the received feedback signal.

Figure 6:
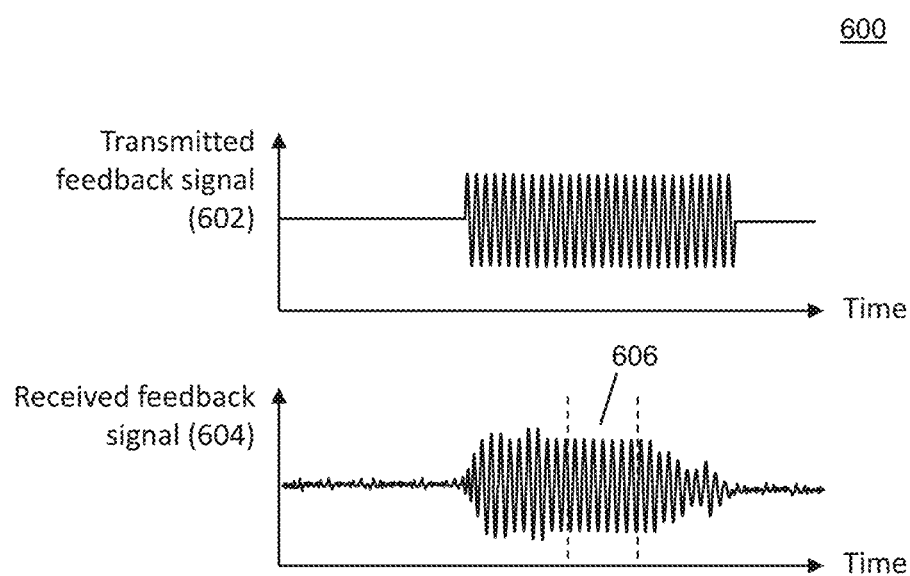
FIG. 6 is a timing diagram of an illustrative variation of a received feedback signal with a settled amplitude.

FIG. 6 shows a timing diagram of an illustrative variation of a feedback signal used in a method of exchanging wireless signals with a wireless device (600). As shown, a transmitted feedback signal (602) from a first device (e.g., a wireless implantable device) may undergo multipath interference in the wireless link, such that the received feedback signal (604) by a second device (e.g., an external wireless device) may comprise a varying amplitude level. In some variations, extracting one or more portions of the received feedback signal (604) may comprise finding one or more regions of the received feedback signal waveform with a settled amplitude (606). In some variations, such a region of the received feedback signal (606) may correspond to a duration where all major reflections of the feedback signal in the wireless link may be in steady state. In some variations, such a region of the received feedback signal (606) may occur after the last major reflection of the feedback signal is received by the second device. In some variations, the duration of the transmitted feedback signal (602) may be greater than about 5 cycles of a carrier frequency of the feedback signal. This long duration of the feedback signal may allow settling of the amplitude of the received feedback signal accounting for constructive and/or destructive interference from reflections of the feedback signal in the wireless link. In some variations, the duration of the transmitted feedback signal (602) may be chosen based on the expected positions of reflectors (e.g., ribs, lungs, tissue boundaries, and the like) in the wireless link relative to the positions of the first device and the second device. For instance, in some variations, if reflections in a wireless link are expected to settle within about 100 microseconds (e.g., settling of a signal amplitude within 5% or 1%, and the like), the duration of the feedback signal may be chosen to be about 100 microseconds or greater. In some variations, the duration of the transmitted feedback signal (602) may be chosen based on a multipath time of the link (e.g., time delay between the arrival times of a direct line-of-sight signal or a first reflection, and a last reflection of a signal propagating from a first device to a second device of the wireless system). In some variations, extracting a portion of the received feedback signal may comprise detecting one or more regions of the received feedback signal waveform where the envelope of the received feedback signal may not change outside of a predetermined percentage (e.g., outside of +5%).

Optionally, in some variations, the method (500) may comprise detecting one or more of a rising edge and a falling edge of the received feedback signal prior to extracting one or more portions of the received feedback signal. For instance, a rising edge of the received feedback signal may be detected, a timing of the occurrence of the rising edge may be determined, and a region of the received feedback signal may be extracted starting at a time which may be a predetermined duration after the timing of the occurrence of the rising edge. Such a predetermined duration may be based on a multipath time of the wireless link or time required for reflections in the link to settle. In some variations, the detection of a rising and/or a falling edge of a received feedback signal may be performed by comparing the amplitude envelope and/or energy of the received feedback signal with a predetermined threshold. In some variations, such a comparison to a predetermined threshold may be performed in the time domain and/or in the frequency domain (e.g., after computing a Fourier transform or short-time Fourier transform of the received feedback signal). In some variations, a running window or filter, or a matched filter may be applied to the received feedback signal to detect a rising and/or a falling edge. In some variations, an average amplitude envelope and/or an average energy of the received feedback signal, averaged over a predetermined duration, may be compared to a predetermined threshold in order to detect its rising and/or falling edge. For example, a received feedback signal may be digitized and a rising edge may be detected by checking when a predetermined number of consecutive samples of the received feedback signal's amplitude envelope cross a predetermined threshold.

In some variations, the first transducer array (e.g., ultrasonic array) of the second device may comprise a plurality of transducer elements (e.g., ultrasonic transducer elements). In some variations, extracting one or more portions of the received feedback signal may be performed for the feedback signals received by a subset of the elements of the first transducer array. For instance, transducer elements that may not receive sufficient signal strength of the received feedback signal (e.g., due to signal blockage by ribs) may be omitted from further processing in order to save computational resources. In some variations, extracting one or more portions of the received feedback signal may be performed only for one or more transducer elements of the first transducer array that may receive the highest signal strength or signal-to-noise ratio (SNR) of the feedback signal, or a signal strength or SNR above a predetermined threshold. In some variations, extracting one or more portions of the received feedback signal may be performed only for one or more transducer elements of the first transducer array that may have the highest link gain (or efficiency) with the first device, or a link gain (or efficiency) with the first device above a predetermined threshold. In some variations, extracting one or more portions of the received feedback signal may be performed only for one or more predetermined transducer elements of the first transducer array of the second device.

In some variations, the method (500) may further comprise digitizing the feedback signal received by one or more transducer elements of the first transducer array prior to extracting one or more portions of the received feedback signal. In some variations, the method (500) may further comprise detecting a rising edge of the received feedback signal using analog signal processing prior to digitizing the feedback signal received by one or more transducer elements of the first transducer array. For example, such analog signal processing may comprise one or more of envelope detection (e.g., using an envelope detector circuit), integration (e.g., using a charge-integration based wait timer circuit), comparison to a predetermined threshold (e.g., using a comparator and a reference generator circuit), combinations thereof, and the like. In some variations, extracting one or more portions of the received feedback signal is performed using one or more of digital signal processing, analog signal processing, combinations thereof, and the like.

In some variations, the feedback signal data may comprise one or more of an absolute amplitude or magnitude, a relative amplitude or magnitude, an absolute signal strength, a relative signal strength, signal energy in one or more frequency bands, an apodization, an absolute phase, a relative phase, an absolute time delay, a relative time delay, an absolute time of arrival, a relative time of arrival, a frequency, a time duration, number of cycles, an absolute signal-to-noise ratio, a relative signal-to-noise ratio, combinations thereof, and the like, of the feedback signals received by one or more transducer elements of the first transducer array of the second device. In some variations, the relative amplitude, signal strength, phase and/or time delay of a given transducer element may be relative to another transducer element of the second device. In some variations, determining the configuration of the second transducer array of the second device may comprise determining one or more of an amplitude, a signal strength, a phase, a time delay, a frequency, a time duration, a number of cycles, combinations thereof, and the like, for transmitting wireless signals through one or more transducer elements of the second transducer array. In some variations, determining the one or more of an amplitude, a signal strength, a phase, a time delay, a frequency, a time duration, a number of cycles, combinations thereof, and the like, for transmitting wireless signals through one or more transducer elements of the second transducer array may comprise performing one or more of cross-correlation, time reversal, a frequency domain analysis (e.g., computing one or more of a Fourier transform, DFT, DTFT using one or more of FFT and Goertzel algorithms), an interpolation analysis (e.g., based on neighboring transducer elements), combinations thereof, and the like. In some variations, time reversal may comprise reversing the time delays or phases of received feedback signals, received from a first device by one or more transducer elements of a transducer array of a second device, in order to transmit wireless signals to the first device. In some variations, time reversal may result in focusing of an ultrasonic beam at the first device, which may be advantageous for efficient wireless power delivery to the first device (e.g., a wireless implantable device).

In some variations, cross-correlation as described herein, may comprise computing a sliding dot product of at least two received feedback signals received by at least two transducer elements of the first transducer array of the second device. In some variations, cross-correlation may be performed to determine the relative time delay, lag or phase difference between the at least two received feedback signals. In some variations, the relative time delay, lag or phase difference between the at least two received feedback signals may be reversed when transmitting a wireless signal (e.g., power) from the second device to the first device. In some variations, received feedback signals on one or more transducer elements of the first transducer array may be cross-correlated to the received feedback signal with the highest signal strength or amplitude, SNR and/or link gain. In some variations, received and digitized feedback signals may be resampled (e.g., using upsampling, interpolation, expansion, and the like) prior to cross-correlation in order to change (e.g., increase) the resolution of the relative time delay, lag and/or phase difference computed using cross-correlation. In some variations, one or more received feedback signals may be normalized (e.g., scaling the amplitude of the signal to set its maximum value to 1) prior to cross-correlation. In some variations, in order to reduce computations, cross-correlation between two or more received feedback signals may be performed using a maximum lag (or time shift) based upon a time period of the received feedback signal. For example, a maximum lag for cross-correlation may be set to one time period of the carrier frequency of the feedback signal.

In some variations, determining one or more of the amplitudes and the signal strengths for transmitting wireless signals through one or more transducer elements of the second transducer array may comprise one or more of envelope detection, energy detection in a predetermined frequency band (e.g., a bandwidth centered around the carrier frequency of the transmitted feedback signal), comparing relative signal strengths received on different transducer elements of the first transducer array, combinations thereof, and the like. Such signal processing for determining the transmit amplitudes or signal strengths may be performed on the extracted one or more portions of the received feedback signals. Relative transmit signal strengths computed based on determining the relative amplitudes of a settled region of the received feedback signals may be beneficial for efficiently powering a first device from a second device.

In some variations, determining the one or more of the amplitudes, the signal strengths, the phases and the delays for transmitting wireless signals through one or more transducer elements of the second transducer array may further comprise interpolation of one or more of the amplitudes, the signal strengths, the phases and the delays based on the relative spatial positions of the transducer elements of the first transducer array and the second transducer array. For example, a first transducer array may comprise alternate transducer elements of a one-dimensional second transducer array comprising a plurality of equally spaced transducer elements. In this case, one or more of the amplitudes, the signal strengths, the phases and the delays determined for elements of the first transducer array may be interpolated (e.g., using spline interpolation, linear interpolation, and the like) to determine one or more of the amplitudes, the signal strengths, the phases and the delays for one or more transducer elements of the second transducer array. In some variations, phases may be unwrapped prior to interpolation, in order to obtain a continuous phase signal that is not constrained to its principal value of $(-\pi, \pi]$ or $[0, 2\pi)$ radians. In some variations, determining the configuration of the second transducer array may also comprise a method of closed-loop powering, as described herein.

In some variations, the first device may comprise an implantable medical device and the second device may comprise an external wireless device configured to be disposed physically separate from the first device. In some variations, the first transducer array and the second transducer array may comprise one or more common transducer elements (e.g., the same set of transducer elements). In some variations, the first transducer array may comprise a subset of the second transducer array. In some variations, the first transducer array and the second transducer array may comprise distinct transducer elements. In some variations, the first transducer array and the second transducer array may each comprise an acoustic (e.g., ultrasonic) transducer array.

Figure 7:
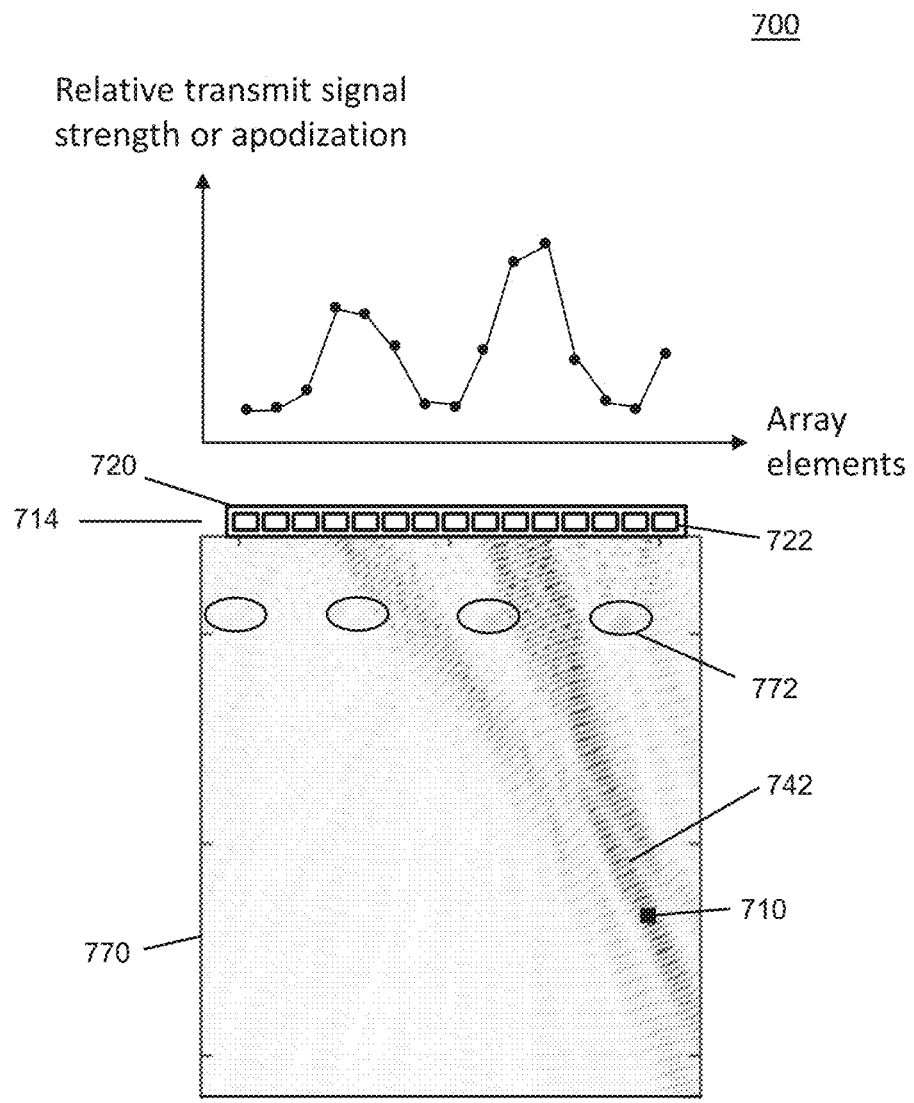
FIG. 7 is a cross-sectional schematic view of an illustrative variation of an ultrasonic beam and transmit signal strengths of an ultrasound transducer array.

FIG. 7 shows a cross-sectional schematic view of a variation of an ultrasonic beam and transmit signal strengths of an ultrasound transducer array (700). The relative transmit signal strength or apodization of the transducer elements (722) of the transducer array (720) of the second device (714) are shown. Apodization may refer to the relative amplitude weighting applied to different transducer elements of a transducer array. The relative transmit signal strengths and corresponding transmit delays (not shown) may be computed using any of the methods described above. This transducer configuration of the second transducer array (720) may result in an ultrasonic beam (742) that may be focused at the location of a wireless implantable device (710) implanted in thoracic tissue (770) comprising the rib cage or ribs (772).

b. Exchanging Wireless Signals Based on a Link Scan Signal

In some variations, transmitting a feedback signal with a long duration (e.g., greater than about 5 cycles of a carrier frequency of the feedback signal) may not be desirable. For instance, it may be desirable to avoid the transmission of a long duration feedback signal from a wireless implantable device due to its limited energy budget (e.g., a miniature implantable device may not have sufficient stored energy, or it may be advantageous to utilize its stored energy for other operations such as sensing or stimulation). This may be especially challenging in wireless systems that experience multipath interference. For instance, as discussed in an example above, in some variations, if the multipath time in a wireless system is about 100 microseconds, then a feedback signal duration greater than or equal to about 100 microseconds may be required to allow settling of the amplitude of the received feedback signal. However, a battery less wireless implantable device may not have sufficient energy to transmit such a long duration feedback signal. Solutions are provided herein to overcome this challenge.

Figure 8:
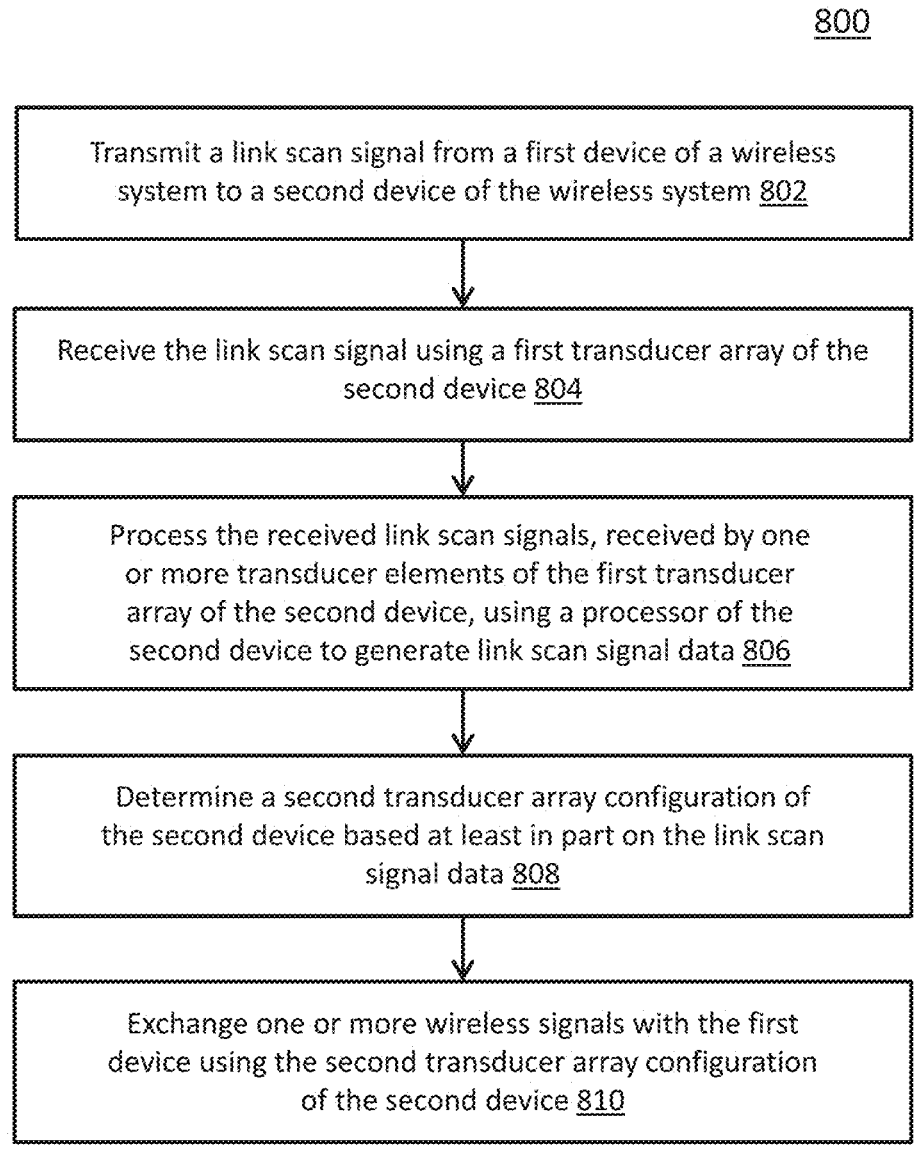
FIG. 8 is a flowchart of an illustrative variation of a method of exchanging wireless signals with a device based on a link scan signal.

In some variations, a method of exchanging wireless signals may be based on a link scan signal, as described herein. FIG. 8 is a flowchart that generally describes a variation of a method of exchanging wireless signals with a device based on a link scan signal (800). The method (800)

may comprise the steps of transmitting a link scan signal from a first device of a wireless system to a second device of the wireless system (802), receiving the link scan signal using a first transducer array of the second device (804), processing the received link scan signals, received by one or more transducer elements of the first transducer array of the second device, using a processor of the second device to generate link scan signal data (806), determining a configuration of a second transducer array of the second device based at least in part on the link scan signal data (808), and exchanging one or more wireless signals with the first device using the second transducer array configuration of the second device (810). The link scan signal, the transducer array, the processor, the transducer array configuration, the link scan signal data, and the wireless signals, as described herein, are applicable to any of the methods described herein.

In some variations, the link scan signal may comprise one or more of an impulse signal, a pulse signal, combinations thereof, and the like. In some variations, the pulse signal may comprise one or more cycles of a carrier frequency of the pulse signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, one or more cycles of a carrier frequency of the pulse signal, combinations thereof, and the like.

In some variations, processing the received link scan signal received by a transducer element of the first transducer array may comprise determining an impulse response of the wireless system. For example, if the transmitted link scan signal comprises an impulse signal, the received link scan signal may comprise an impulse response of the wireless system. In some variations, the impulse response of the wireless system may be determined based upon the received link scan signal and the transmitted link scan signal. For example, the impulse response of the wireless system may be determined by a processor of the second device by performing deconvolution of the received link scan signal with a reference link scan signal (e.g., the transmitted link scan signal). In some variations, the Fourier transform of the received link scan signal may be divided by the Fourier transform of the transmitted link scan signal to determine an impulse response of the wireless system.

In some variations, processing the received link scan signal may further comprise performing convolution of the impulse response of the wireless system corresponding to one or more transducer elements of the first transducer array with one or more template signals. A template signal may be any signal generated and/or received by a processor of the second device. For example, a template signal may comprise a sinusoidal or a rectangular pulse comprising one or more cycles of a carrier frequency. In some variations, the template signal may represent, or may be the same as, a transmitted feedback signal of the method (500) of exchanging wireless signals based on a feedback signal. In some variations, the template signal may comprise a pulse signal. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, one or more cycles of a carrier frequency of the pulse signal, combinations thereof, and the like. In some variations, the duration of the template signal may be greater than about 5 cycles of a carrier frequency of the template signal. In some variations, the same template signal may be used for processing the link scan signals received by different transducer elements of the first transducer array of the second device. In some variations, different template signals may be used for processing the link scan signals received by different transducer elements of the first transducer array of the second device. Considerations for the duration of the feedback signal discussed herein (e.g., feedback signal duration greater than or equal to multipath time of a wireless link) may be applicable to the duration of the template signal as well.

In some variations, the link scan signal data may comprise the output signal of the convolution of the received link scan signal with the template signal, or any property (e.g., amplitude, time delay, phase, frequency, and the like) of the output signal of the convolution. In some variations, the link scan signal data may comprise one or more of an absolute amplitude, a relative amplitude, an absolute signal strength, a relative signal strength, an apodization, an absolute phase, a relative phase, an absolute time delay, a relative time delay, combinations thereof, and the like, of the output signal of the convolution. In some variations, the relative amplitude, signal strength, phase and/or time delay of a given transducer element may be relative to another transducer element of the second device.

Figure 9:
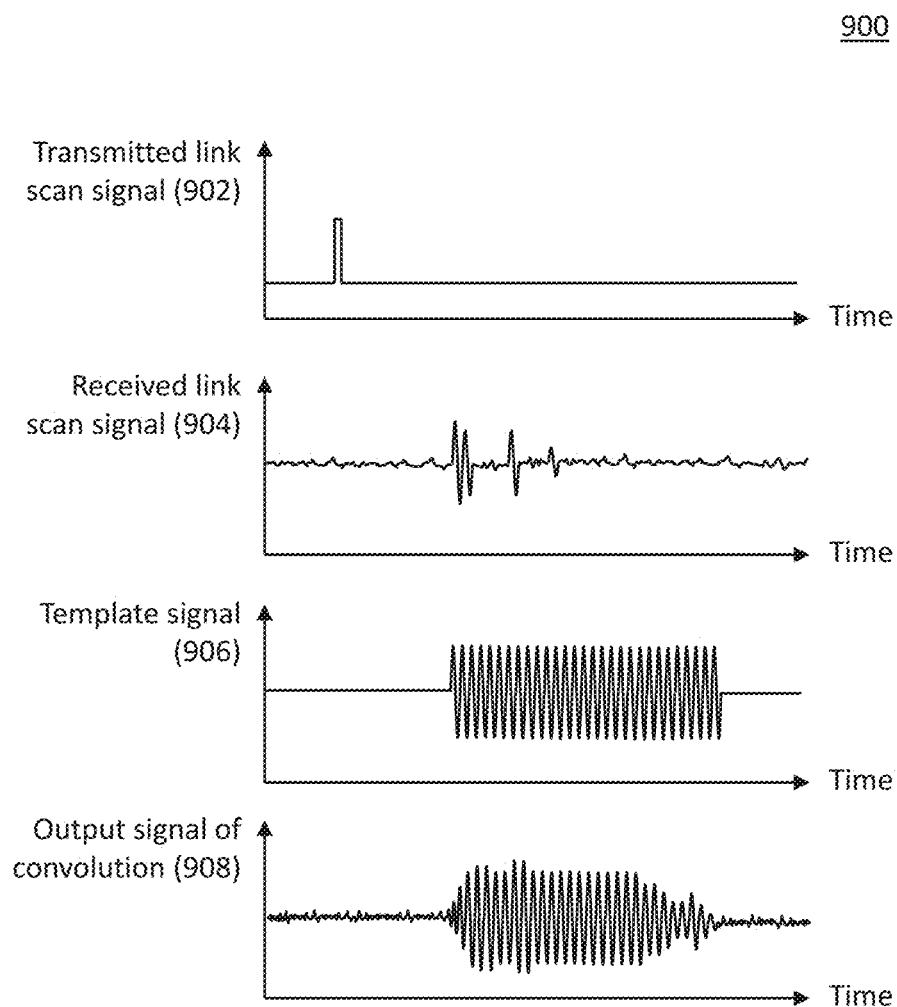
FIG. 9 is a timing diagram of an illustrative variation of signals used in a method of exchanging wireless signals with a device.

FIG. 9 is a timing diagram of an illustrative variation of signals used in the method of exchanging wireless signals using a link scan signal (900). As shown, in some variations, the transmitted link scan signal (902), transmitted by a first device of a wireless system, may comprise a short-duration rectangular pulse that may approximate a Dirac pulse or a Dirac Delta function. Such a link scan signal may be advantageous to measure an impulse response of the wireless system (e.g., to characterize a transfer function of the wireless link of the wireless system) or an approximate impulse response of the wireless system or a scaled impulse response of the wireless system. Also shown is a conceptual representation of the corresponding received link scan signal (904), received by a transducer element of a first transducer array of a second device of the wireless system. The received link scan signal (904) may comprise a carrier frequency and bandwidth based upon a resonance frequency and bandwidth of one or more of the transducer of the first device and the transducer of the second device. Further, the received link scan signal (904) may comprise one or more pulse signals due to multipath interference (reflections of the link scan signal received from one or more reflectors or scatterers in the wireless link). Also shown is an example of a template signal (906) comprising a plurality of cycles of a carrier frequency. The received link scan signal (904) may be convolved with the template signal (906) by a processor of the second device to generate the output signal of the convolution (908). In some variations, the output signal of the convolution (908) may emulate a received feedback signal of the method (500) of exchanging wireless signals based on a feedback signal. In some variations, the output signal of the convolution (908) may be further processed using processing steps similar to those applied to the received feedback signal in the method (500) of exchanging wireless signals based on a feedback signal described herein.

In some variations, determining the configuration of the second transducer array of the second device may comprise determining one or more of an amplitude, a signal strength, a phase, a time delay, combinations thereof, and the like, for transmitting wireless signals through one or more transducer elements of the second transducer array. In some variations, determining one or more of the amplitude, the signal strength, the phase and the time delay for transmitting wireless signals through one or more transducer elements of the second transducer array may comprise performing one or more of cross-correlation, time reversal, combinations thereof, and the like. The steps of cross-correlation and time reversal, as described herein, may be applicable here as well.

In some variations, determining one or more of the amplitude, the signal strength, the phase and the time delay for transmitting wireless signals through one or more transducer elements of the second transducer array may further comprise interpolation of one or more of the amplitudes, the signal strengths, the phases and the time delays based on the relative spatial positions of the transducer elements of the first transducer array and the second transducer array. In some variations, determining the configuration of the second transducer array may comprise a method of closed-loop powering. The steps of interpolation, as described herein, may be applicable here as well.

In some variations, the first device may comprise an implantable medical device and the second device may comprise an external wireless device configured to be disposed physically separate from the first device. In some variations, the first transducer array and the second transducer array may comprise one or more common transducer elements (e.g., the same set of transducer elements). In some variations, the first transducer array may comprise a subset of the second transducer array. In some variations, the first transducer array and the second transducer array may comprise distinct transducer elements. In some variations, the first transducer array and the second transducer array may each comprise an acoustic (e.g., ultrasonic) transducer array.

Figure 10:
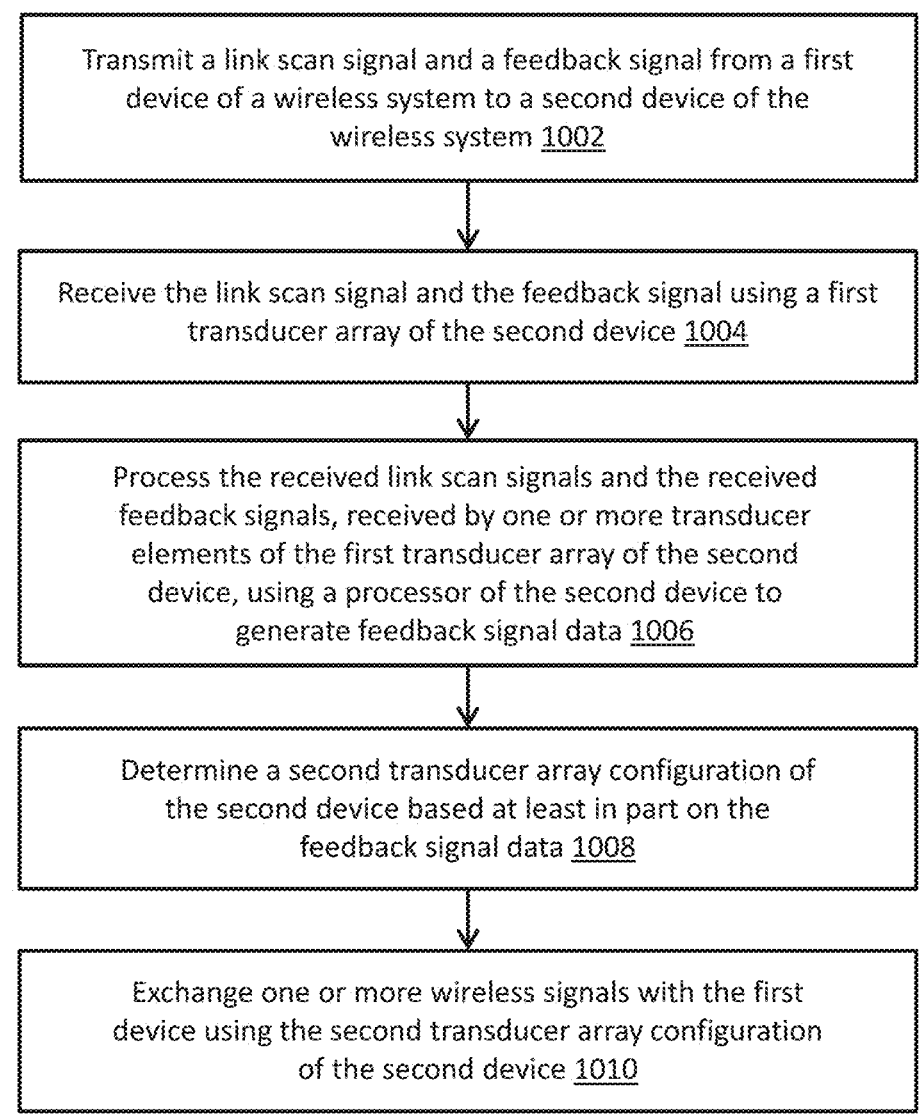
FIG. 10 is a flowchart of an illustrative variation of a method of exchanging wireless signals with a device based on a link scan signal and a feedback signal.

In some variations, the first transducer array (e.g., ultrasonic array) of the second device may comprise a plurality of transducer elements (e.g., ultrasonic transducer elements). In some variations, processing the received link scan signals may be performed for the link scan signals received by a subset of the elements of the first transducer array. For instance, transducer elements that may not receive sufficient signal strength of the received link scan signal (e.g., due to signal blockage by ribs) may be omitted from further processing in order to save computational resources. In some variations, processing the received link scan signals may be performed only for one or more transducer elements of the first transducer array that may receive the highest signal strength or signal-to-noise ratio of the link scan signal, or a signal strength or SNR above a predetermined threshold. In some variations, processing the received link scan signals may be performed only for one or more transducer elements of the first transducer array that may have the highest link gain (or efficiency) with the first device, or a link gain (or efficiency) with the first device above a predetermined threshold. In some variations, processing the received link scan signals may be performed only for one or more predetermined transducer elements of the first transducer array of the second device.

c. Exchanging Wireless Signals Based on a Feedback Signal and a Link Scan Signal In some variations, a method of exchanging wireless signals may be based on a feedback signal and a link scan signal, as described herein. FIG. 10 is a flowchart that generally describes a variation of a method of exchanging wireless signals with a device based on a feedback signal and a link scan signal (1000). The method (1000) may comprise the steps of transmitting a link scan signal and a feedback signal from a first device of the wireless system to a second device of the wireless system (1002), receiving the link scan signal and the feedback signal using a first transducer array of the second device (1004), processing the received link scan signals and the received feedback signals, received by one or more transducer elements of the first transducer array of the second device, using a processor of the second device to generate feedback signal data (1006), determining a configuration of a second transducer array of the second device based at least in part on the feedback signal data (1008), and exchanging one or more wireless signals with the first device using the configuration of the second transducer array of the second device (1010). The feedback signal, the link scan signal, the transducer array, the processor, the transducer array configuration, the feedback signal data, the link scan signal data, and the wireless signals, as described herein, are applicable to any of the methods described herein.

In some variations, processing the received link scan signal and the received feedback signal may comprise performing deconvolution of the received feedback signal with the received link scan signal. In some variations, processing the received link scan signal received by a transducer element of the first transducer array may comprise determining an impulse response of the wireless system. In some variations, processing the received link scan signal and the received feedback signal may comprise performing deconvolution of the received feedback signal with the impulse response of the wireless system or a scaled impulse response of the wireless system. In some variations, the method (1000) may further comprise extracting one or more portions of the output signal of the deconvolution using a processor of the second device. In some variations, extracting the one or more portions of the output signal of the deconvolution may comprise finding one or more regions of the output signal of the deconvolution with a settled amplitude.

In some variations, determining the second transducer array configuration of the second device may comprise determining one or more of an amplitude, a signal strength, a phase and a time delay for transmitting wireless signals through one or more transducer elements of the second transducer array. In some variations, determining the one or more of the amplitude, the signal strength, the phase and the time delay for transmitting wireless signals through one or more transducer elements of the second transducer array may comprise performing one or more of cross-correlation and time reversal. The steps of cross-correlation and time reversal, as described herein, may be applicable here as well.

In some variations, determining one or more of the amplitudes, the signal strengths, the phases and the delays for transmitting wireless signals through one or more transducer elements of the second transducer array may further comprise interpolation of one or more of the amplitudes, the signal strengths, the phases and the delays based on the relative spatial positions of the transducer elements of the first transducer array and the second transducer array. The steps of interpolation, as described herein, may be applicable here as well. In some variations, determining the second transducer array configuration comprises a method of closed-loop powering.

In some variations, the first device may comprise an implantable medical device and the second device may comprise an external wireless device configured to be disposed physically separate from the first device. In some variations, the first transducer array and the second transducer array may comprise one or more common transducer elements (e.g., the same set of transducer elements). In some variations, the first transducer array may comprise a subset of the second transducer array. In some variations, the first transducer array and the second transducer array may comprise distinct transducer elements. In some variations, the first transducer array and the second transducer array may each comprise an acoustic (e.g., ultrasonic) transducer array.

In some variations, certain transducer elements of the first transducer array may be chosen for processing their corresponding feedback signals and link scan signals, using criteria similar to those described for the method (500) of exchanging wireless signals based on a feedback signal and the method (800) of exchanging wireless signals based on a link scan signal.

d. Exchanging Wireless Signals Based on Defocusing

In some variations, a transducer array configuration of a second device determined using methods described above may not be sufficient for exchanging wireless signals with a first device if the first device exhibits excessive movement relative to the second device. For example, a wireless implantable device implanted in the heart may move relative to a stationary external wireless device located on a patient's chest. In some cases, after transmitting a feedback signal and/or a link scan signal, the wireless implantable device may move to a different location relative to the external wireless device, before the external wireless device may process the received feedback signal and/or the received link scan signal and transmit power to the wireless implantable device's original location. This may result in inadequate wireless power delivery to the wireless implantable device and may, thus, significantly limit its functions. Solutions are provided herein to overcome this challenge.

In some variations, defocusing of the wireless beam (e.g., an ultrasonic beam) may be intentionally performed in order to exchange wireless signals with a moving wireless implantable device. This may result in a large beam diameter near the location of the wireless implantable device to accommodate the range of motion of the wireless implantable device over a given time duration.

In some variations, a method of exchanging wireless signals between a first device of a wireless system and a second device of the wireless system may comprise the methods described above based on one or more of a feedback signal and a link scan signal. A transducer array configuration of the second device may be determined comprising one or more of a set of transducer elements of the transducer array, a signal strength, an amplitude, an apodization, a time delay, a phase, combinations thereof, and the like. Such parameters of the transducer configuration may be determined using techniques such as cross-correlation and/or time reversal as described herein. In some variations, the parameters of the transducer configuration may be further adjusted in order to defocus the beam.

In some variations, the aperture and/or the apodization of the transducer array may be adjusted to defocus the beam. In some variations, a smaller sub-aperture or sub-array of the transducer array of the second device may be selected (e.g., by turning off other transducer elements of the array) for exchanging wireless signals with the first device because a smaller aperture may correspond to a wider beam diameter. For example, the sub-array (comprising a contiguous set of transducer elements or a non-contiguous set of transducer elements) may be chosen by selecting transducer elements that received a feedback signal strength greater than a predetermined threshold. In some variations, the sub-array may be chosen by selecting transducer elements with apodization (determined after processing the received feedback signals and/or the received link scan signals) greater than a predetermined threshold (e.g., greater than about 0.5). In some variations, the sub-array may be chosen by selecting transducer elements adjacent to or near the transducer element with the largest or the smallest delay or phase.

In some variations, a plurality of feedback signals and/or link scan signals may be received from a first device corresponding to one or more positions of the first device relative to the second device. Such a plurality of received feedback signals and/or received link scan signals may be processed by a processor of the second device in order to generate a plurality of apodizations and/or delay profiles using one or more of cross-correlation, time reversal, combinations thereof, and the like. In some variations, the transducer array configuration of the second device for exchanging wireless signals with the first device may comprise a mean of the plurality of the apodizations and/or the delay profiles. Such a mean apodization and/or delay profile may result in a wider beam diameter covering the range of motion of the first device. In some variations, the selected delay profile for exchanging wireless signals with the first device may comprise the delay profile corresponding to the wireless implantable device location for which the apodization profile is closest (or most similar) to the mean apodization profile across a plurality of wireless implantable device locations.

In some variations, the phases and/or delays applied to transducer elements of the transducer array may be adjusted to defocus the beam. In some variations, the curvature of the delay or phase profile across the transducer array of the second device may be adjusted (e.g., increased or decreased) in order to shift the focus of an ultrasonic beam to a location between the first device and the second device, or beyond the first device farther away from the second device. By doing so, a wider beam diameter may be achieved near the location of the first device (thereby covering its range of motion), compared to when the beam is directly focused at one of the locations of the first device.

In some variations, the frequency of wireless signals transmitted by the transducer array of the second device may be adjusted to defocus the beam. In some variations, a low frequency may be chosen as it may result in a wider beam diameter due to a larger wavelength. In some variations, a feedback signal may be received by a second device from a first device at a first frequency, but power may be transferred by the second device to the first device at a second frequency, wherein the second frequency may be lower than the first frequency. In some variations, the same apodization and time delays computed based on the feedback signal at the first frequency may be utilized for transmitting wireless signals to the first device at the second frequency. Using a lower second frequency to transfer wireless power may result in a wider beam diameter and lower tissue loss, thereby, allowing reliable power transfer to the first device in spite of its movement relative to the second device.

e. Closed-Loop Powering

A method of closed-loop powering is described herein. In some variations, a method of closed-loop powering may be used to target a requisite power level at the first device when transmitting wireless power from a second device to the first device in a wireless system. The absolute signal strengths transmitted by transducer elements of a transducer array of the second device, or total transmit power of the second device, may be determined based on a method of closed-loop powering.

In some variations, the power of a feedback signal transmitted by a first device may be known and denoted by $P_{TX,fb}$. The power of the feedback signal received by the second device may be denoted by $P_{RX,fb}$. A processor of the second device may be configured to compute an uplink link gain or uplink link efficiency, $\eta_{uplink}$ (i.e., gain or efficiency for signals propagating from the first device to the second device). The uplink link efficiency may be given by:

$$\eta_{uplink} = \frac{P_{RX,fb}}{P_{TX,fb}} \quad (1)$$

In some variations, a downlink link efficiency, $\eta_{downlink}$ (i.e., gain or efficiency for signals propagating from the second device to the first device), may be estimated based on the measured uplink link efficiency, $\eta_{uplink}$. In some variations, based on reciprocity in a wireless link, the downlink link efficiency may be determined to be equal, or approximately equal, to the uplink link efficiency. In some variations, the downlink link efficiency may be different from the uplink link efficiency (e.g., if the link gain comprises one or more non-reciprocal gain components). The downlink link efficiency, $\eta_{downlink}$, may be related to a target received power level ($P_{RX,power}$) at the first device when wirelessly powering the first device from the second device, and the transmit power from the second device ($P_{TX,power}$) using:

$$\eta_{downlink} = \frac{P_{RX,power}}{P_{TX,power}} \quad (2)$$

Assuming that the downlink link efficiency is equal to the uplink link efficiency for reciprocal systems, the required transmit power level from the second device may be computed as:

$$P_{TX,power} = P_{RX,power} \times \frac{P_{TX,fb}}{P_{RX,fb}} \quad (3)$$

In some variations, a total transmit power level of the transducer array of the second device may be selected to be greater than the value computed using the equation above, in order to keep sufficient margin for link variations or aberrations. Based on the computed total transmit power level of the transducer array, the absolute transmit signal strengths for individual transducer elements of the array may be determined based on their relative signal strengths and impedance of the transducer elements.

In some variations, the total transmit power level required at the second device may be determined based on feedback from the first device. For example, the first device may be configured to digitize its received voltage or power level, and transmit this digitized voltage or power level to the second device via one or more feedback signals, wherein the second device may adjust (increase or decrease) its transmit power in order to achieve a requisite voltage or power level at the first device.

In some variations, the first device may comprise an implantable medical device and the second device may comprise an external wireless device configured to be disposed physically separate from the first device.

B. Decoding Wireless Data Signals

In some variations, wireless data communication in a wireless system may be affected by multipath interference due to reflections of wireless signals propagating in the wireless link off heterogeneous media and structures. Multipath interference may result in corruption of the wireless data signal waveforms received by the receiving device of the wireless system. Decoding of such wireless data signals using conventional techniques may result in undesirable bit errors. For example, a wireless implantable device implanted in the heart may sense a physiological parameter (e.g., pressure), digitize it, and transmit the digitized physiological parameter data via an ultrasonic uplink data signal to an external wireless device. The ultrasonic uplink data signals may experience multipath interference due to reflection and/or scattering of ultrasonic waves off ribs, lungs and/or other tissue boundaries. This may result in corruption of the uplink data signal waveform received by the external wireless device, leading to bit errors in the decoded physiological parameter data, which may result in inadequate or inaccurate management of the patient's disease. Solutions are provided herein to overcome such a challenge.

Figure 11:
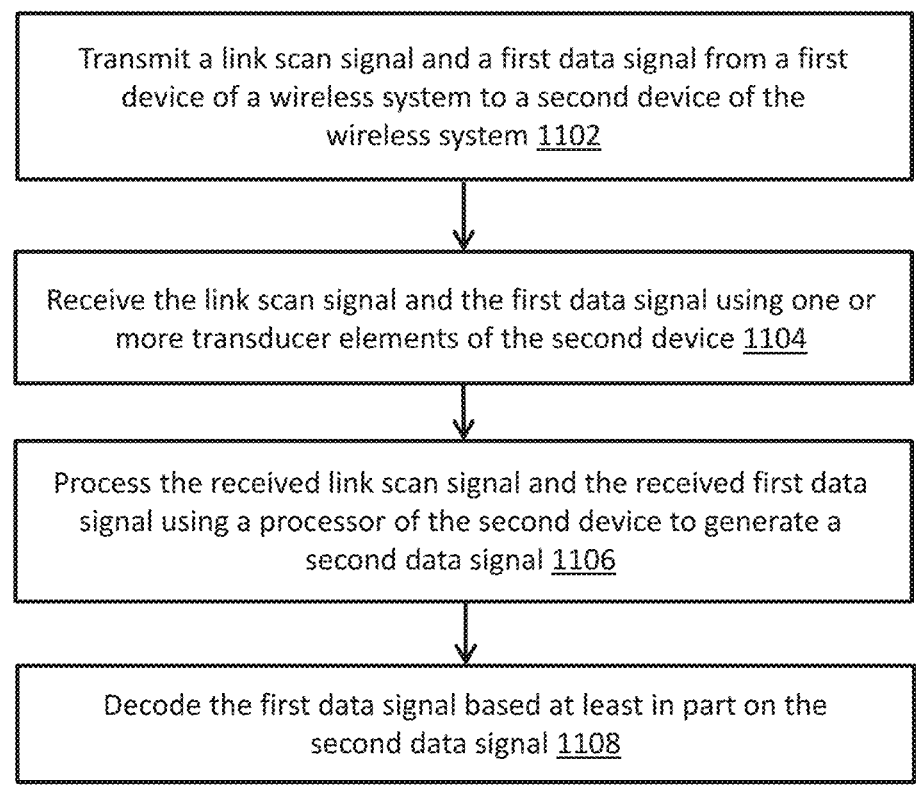
FIG. 11 is a flowchart of an illustrative variation of a method of decoding a data signal in a wireless system.

In some variations, wireless data communication between two wireless devices may utilize a link scan signal. FIG. 11 is a flowchart that generally describes a variation of a method of decoding a data signal in a wireless system (1100). The method (1100) may comprise the steps of transmitting a link scan signal and a first data signal from a first device of the wireless system to a second device of the wireless system (1102), receiving the link scan signal and the first data signal using one or more transducer elements of the second device (1104), processing the received link scan signal and the received first data signal using a processor of the second device to generate a second data signal (1106), and decoding the first data signal based at least in part on the second data signal (1108). The link scan signal, the data signal (the first data signal, the second data signal), the transducer elements and the processor, as described herein, are applicable to any of the methods described herein.

In some variations, the link scan signal may comprise one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals, a plurality of pulse signals, combinations thereof, and the like. In some variations, the pulse signal may comprise one or more of a rectangular pulse, a Dirac pulse, a sinusoidal pulse, a triangular pulse, a trapezoidal pulse, a raised cosine pulse, a sinc pulse, a Gaussian pulse, one or more cycles of a carrier frequency of the pulse signal, combinations thereof, and the like. In some variations, the link scan signal may comprise a portion of the first data signal. For instance, the link scan signal may comprise one or more headers and/or one or more footer sections of the first data signal. In some variations, there may be a time delay between the link scan signal and the first data signal (e.g., a time delay to capture multipath reflections of an impulse signal, feedback signal or pulse signal). In some variations, there may be no time gap between the link scan signal and the first data signal (e.g., they may be contiguous waveforms).

In some variations, the first data signal may comprise one or more of an uplink data signal and a downlink data signal. In some variations, the first data signal may comprise one or more of on-off keying (OOK) modulation, amplitude-shift keying (ASK) modulation, pulse-position modulation (PPM), frequency-shift keying (FSK) modulation, phase-shift keying (PSK) modulation, quadrature amplitude modulation (QAM), combinations thereof, and the like.

In some variations, processing a received link scan signal and/or a received first data signal, received by one or more transducer elements, and described in any method herein, may comprise one or more of analog signal processing, digital signal processing, signal amplification, low-pass filtering (e.g., anti-alias filtering), digitization, deconvolution of a received data signal with a received link scan signal or an impulse response of the wireless system, bandpass filtering (e.g., to reject out-of-band thermal noise and thereby improve SNR), matched filtering (e.g., to detect bits, header, footer, and the like, in a data signal), cross-correlation (e.g., to determine relative lag or delay between two data signals in order to delay and sum them), auto-correlation, signal combining (e.g., to improve the SNR of the data signal), delaying and summing two or more data signals (e.g., to improve SNR), digital demodulation (e.g., OOK demodulation), comparison to a predetermined threshold, combinations thereof and the like.

In some variations, the link scan signals and the first data signals received by different transducer elements or channels of the second device may first be individually processed (e.g., using amplification, digitization, low-pass filtering, deconvolution, matched filtering, cross-correlation, combinations thereof, and the like) to generate a second data signal corresponding to each of the processed channels. One or more of the second data signals from different channels may then be combined with each other (e.g., using cross-correlation to determine relative lags, delaying and summing to combine signals, combinations thereof, and the like), followed by decoding the data from the combined signal (e.g., by applying a matched filter to the combined signal, and comparing the envelope of the output to a predetermined threshold to detect a '1' or a '0' bit depending on the result of comparison). The reason for signal combining may be to improve the SNR and/or signal-to-interference ratio (SIR) in order to reduce the number of bit errors or bit error rate in the decoded data. In some variations, instead of performing signal combining operation on all processed channels, certain channels may be selected for signal combining. In some variations, such channels selected for signal combining may be the channels for which the second data signal may have the highest SNR, SIR, SNR above a predetermined threshold, SIR above a predetermined threshold, a correct value for header bits of the data stream, combinations thereof, and the like.

In some variations, upon generating a second data signal corresponding to each of the processed channels, instead of signal combining followed by data decoding, data decoding may be performed on a plurality of the second data signals. In some variations, the final result for decoded data bits may be determined based upon majority occurrence of bits (e.g., if the first decoded bit for majority of the processed channels is '1', then the first decoded bit may be designated as '1'). In some variations, the received link scan signals and the received first data signals from a plurality of channels may be combined prior to processing and generation of a second data signal. For example, the received link scan signals and the received first data signals from a plurality of channels or transducer elements of the transducer array of the second device may be delayed and summed based upon one or more of delays computed using cross-correlation, delays determined from processing feedback signals, delays determined or used in a previous iteration of a method of decoding wireless data signals described herein, delays determined or used in a previous iteration of a method of exchanging wireless signals described herein, combinations thereof, and the like.

In some variations, the processor of the second device may be configured to detect an onset (e.g., rising edge, time of arrival) of one or more of the received link scan signal and the received first data signal. In some variations, onset detection may comprise using one or more of envelope detection, predetermined timing (e.g., based on knowledge of the time at which the first device may transmit the link scan signal or first data signal and signal propagation delay from the first device to the second device), coherent detection, and comparison of the received feedback signal amplitude to a threshold level (e.g., a predetermined threshold).

In some variations, processing the received link scan signal and the first data signal may comprise selecting one or more time durations of one or more of the received link scan signal and the received first data signal prior to further processing based on one or more of a predetermined timing, signal onset detection, detection of one or more of a signal rising edge and a signal falling edge, detection of one or more of a header component and a footer component of a signal, a multipath time and a drift in the frequency of the received first data signal. In some variations, the timing of the rising edge of one or more of the link scan signal (e.g., a feedback signal pulse) and the first data signal may be detected (e.g., using envelope detection and comparing the envelope to a predetermined threshold), and the time duration for processing the link scan signal and the first data signal may be selected based on predetermined fixed time offsets before and after the time of the rising edge. The fixed time offset before the timing of the rising edge may be determined based on the difference between the minimum and maximum propagation delays of wireless signals between the first device and different transducer elements of the second device. The fixed time offset after the timing of the rising edge may be determined based on one or more of a duration of the link scan signal transmitted by the first device, a duration of the first data signal transmitted by the first device, a duration of multipath interference (e.g., multipath time), and detection of an end (e.g., falling edge, footer, and the like) of one or more of the link scan signal and the first data signal.

In some variations, one or more signals processed herein may be zero padded prior to further processing (e.g., to conform to a predetermined number of samples for digital processing operations such as FFT computation). For instance, signals may be zero padded prior to deconvolution and/or convolution operations as described herein. In some variations, one or more signals processed herein may be filtered (e.g., using one or more of a band-pass filter, a low-pass filter, a high-pass filter, an all-pass filter, a notch filter and a band-reject filter). In some variations, one or more signals processed herein may undergo one or more of a conversion from time domain to frequency domain (e.g., using FFT operation) and a conversion from frequency domain to time domain (e.g., using inverse FFT operation), in order to perform the processing in one or more of frequency domain or time domain. In some variations, one or more signals processed herein may be up-sampled, down-sampled or re-sampled prior to further processing. For instance, two signals may be up-sampled (e.g., increase the signal's sampling frequency using one or more interpolation techniques such as spline interpolation) prior to cross-correlation in order to obtain a finer temporal resolution of their relative lags or time delays. In some variations, one or more signals processed herein may be scaled or normalized prior to further processing. For instance, two signals may both be normalized (e.g., spanning an amplitude range from −1 to +1) prior to cross-correlation or deconvolution.

In some variations, processing the received link scan signal may comprise determining an impulse response or a scaled impulse response of the wireless system. Determining the impulse response may characterize a transfer function of the wireless link, which may allow accurate data decoding in the presence of multipath interference, as described herein. In some variations, the received link scan signal may itself represent the impulse response or the scaled impulse response of the wireless system (e.g., when the link scan signal may comprise an impulse signal). In some variations, the scaled impulse response of the wireless system may comprise an impulse response of the wireless system scaled by a predetermined factor which may have a value of 1 or a value other than 1.

In some variations, determining a scaled impulse response (e.g., transfer function of a wireless system or wireless link) of the wireless system may comprise deconvolving the scaled received link scan signal (e.g., a feedback signal) with a scaled reference link scan signal (e.g., a reference feedback signal) using one or more of frequency domain (or Laplace domain) analysis and time domain analysis.

In some variations, a scaled signal described herein (e.g., an impulse response, a received feedback signal, a reference feedback signal, a received link scan signal, a reference link scan signal, a received first data signal, a second data signal, a combined data signal, combinations thereof, and the like) may comprise the signal scaled by one or more of the signal's amplitude in time domain, the signal's amplitude at a frequency, the signal's energy in one or more frequency bands, signal-to-noise ratio, an apodization of the corresponding transducer element on which the signal is received, a predetermined scaling factor (e.g., a scaling factor of 1 or a value other than 1), a scaling factor for normalization, combinations thereof, and the like. In some variations, scaling of a signal (e.g., reducing the signal's maximum amplitude) may be performed prior to an operation (e.g., multiplication by another signal or convolution with another signal) in order to avoid saturation of the resulting signal's amplitude relative to an amplitude limit (e.g., a maximum number of bits in an FPGA register). In some variations, scaling signals by their SNR value prior to combining the signals may allow generating a combined signal with a higher SNR compared to the combined signal obtained without prior scaling of the signals.

In some variations, the scaled reference link scan signal may represent the link scan signal transmitted by the first device (i.e., before the link scan signal propagates through the wireless link). In some variations, the scaled reference link scan signal may comprise an idealized link scan signal (e.g., an ideal impulse, an ideal rectangular pulse). In some variations, the method of decoding data signals in a wireless system may comprise preloading (or storing) the scaled reference link scan signal (e.g., a scaled reference feedback signal) using one or more of a frequency domain representation and a time domain representation into a memory of the second device. For instance, this may be possible in systems where the link scan signal transmitted by the first device is known a priori to the second device (e.g., one or more of the frequency, duration, number of cycles, amplitude, phase, combinations thereof, and the like, of the transmitted link scan signal may be known a priori).

In some variations, the method of decoding data signals in a wireless system may comprise generating one or more of a frequency domain representation and a time domain representation of the scaled reference link scan signal (e.g., a scaled reference feedback signal) based on one or more properties of one or more of the received link scan signal and the received first data signal. In some variations, the property of one or more of the received link scan signal and the received first data signal may comprise one or more of a frequency, a duration, a number of cycles, an amplitude, a phase, and a time of arrival. For instance, the processor of the second device may be configured to detect a carrier frequency of one or more of the received link scan signal and the received first data signal (on one or more transducer elements), and generate a pulse signal based on the detected carrier frequency and a predetermined number of cycles. This may be useful in systems where the carrier frequency used by the first device for signal transmission may not be known a priori to the second device.

In some variations, deconvolution may be performed in one or more of time domain and Laplace or frequency domain. For instance, deconvolving a time domain signal a(t) with another time domain signal b(t) in the Laplace or frequency domain may comprise converting the time domain signals to frequency domain signals (e.g., A(f) and B(f)) and computing the division A(f)/B(f)). For instance, an impulse response (IR) of the wireless system may be determined by dividing the FFT of the received feedback signal by the FFT of a reference (or transmitted) feedback signal. In some variations, one or more deconvolution operations described herein may additionally comprise one or more of a regularization and adding a noise floor in order to avoid division by zero (or division by very small numbers) or to reject an artifact in the output of deconvolution.

In some variations, processing the received link scan signal and the received first data signal may comprise deconvolving a scaled received first data signal with one or more of the scaled impulse response and a scaled received link scan signal, using one or more of a frequency domain analysis and a time domain analysis, to generate the second data signal.

In some variations, processing the received link scan signal (e.g., in impulse signal, a feedback signal, a pulse signal) and the received first data signal may comprise deconvolving a scaled received first data signal with a scaled received link scan signal, using one or more of a frequency domain analysis and a time domain analysis, to generate the second data signal or its scaled version. For instance, the received link scan signal may represent an impulse response or a pulse response of the wireless system. In some variations, the link scan signal may comprise one or more of an impulse signal, a feedback signal, a pulse signal, a pulse signal representing a single data bit of the first data signal (e.g., a pulse representing a '1' bit of OOK modulation), a pulse signal representing a plurality of data bits of the first data signal, a plurality of impulse signals, a plurality of pulse signals, combinations thereof, and the like.

In some variations, deconvolution may be performed to accomplish one or more of rejecting multipath interference and aligning signals in time. In some variations, the second data signal may comprise one or more of an output signal of deconvolution (e.g., in time domain, frequency domain, or both), a train of impulses, a train of pulses, combinations thereof, and the like.

Figure 12:
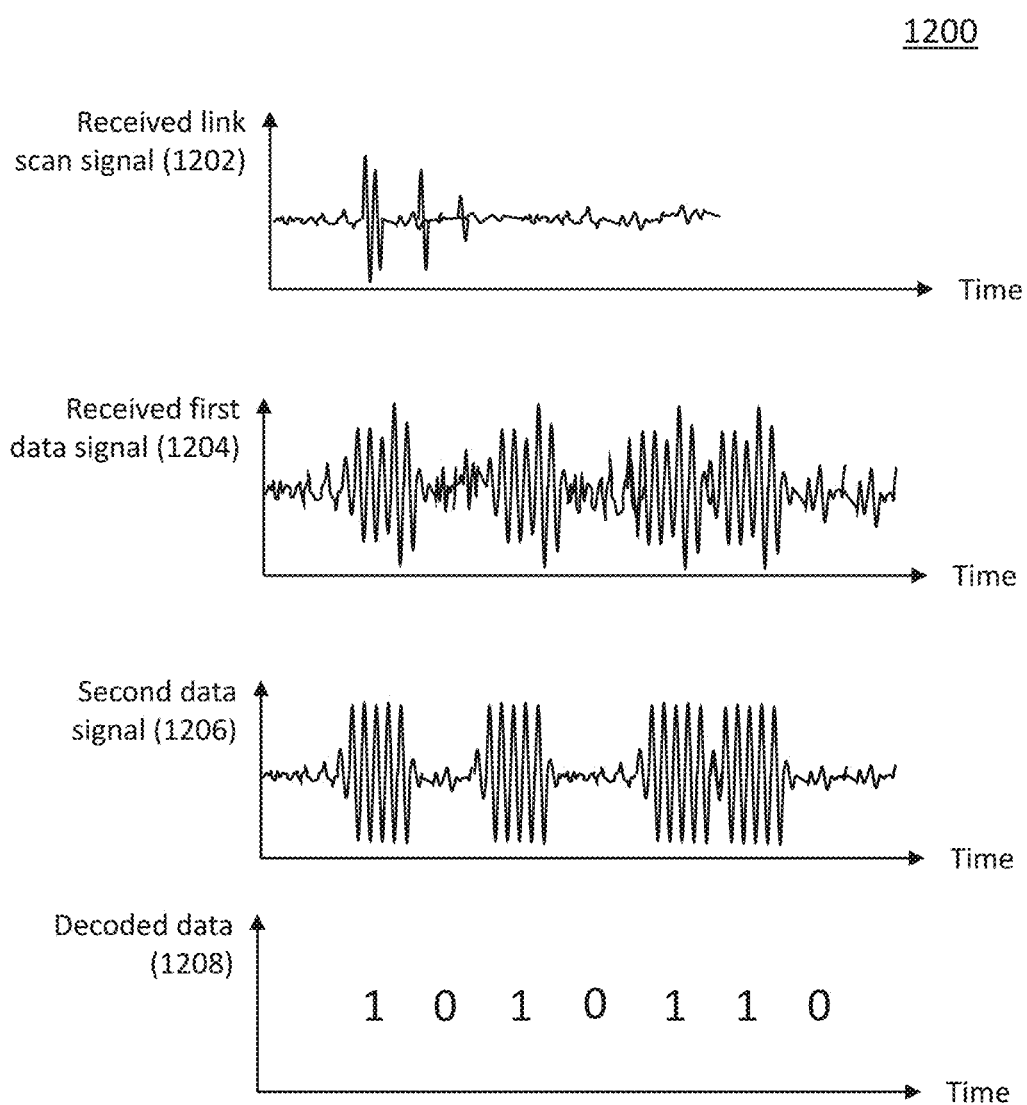
FIG. 12 is a timing diagram of an illustrative variation of signals used in a method of decoding a data signal in a wireless system.

FIG. 12 shows a timing diagram of a variation of signals that may be used in a method of decoding a data signal in a wireless system (1200). A received link scan signal (1202) is shown, which may comprise one or more pulses due to multipath interference in the wireless link. A received first data signal (1204) using OOK modulation is also shown, which may be corrupted or may have a low signal-to-interference ratio (SIR), or SNR, due to multipath interference. It may be challenging to decode such a received first data signal (1204) using conventional OOK demodulation techniques. In some variations, the received first data signal (1204) may be deconvolved using the received link scan signal (1202), which may represent an impulse response of the wireless system. In some variations, deconvolution may be performed in the time domain and/or in the frequency domain. The output signal of the deconvolution, or the second data signal (1206), is also shown in FIG. 12. Upon inspection of the received first data signal (1204) and the second data signal (1206), it may be noted that deconvolution may help with rejecting or reducing multipath interference or improving the SIR or SNR of the data signal. Performing OOK demodulation on the second data signal (1206) may result in accurate data recovery as shown by the decoded data (1208) in FIG. 12. In some variations, one or more of coherent OOK demodulation techniques (e.g., using mixing), non-coherent OOK demodulation techniques (e.g., using envelope detection), combinations thereof, and the like, may be used for decoding.

Figure 13:
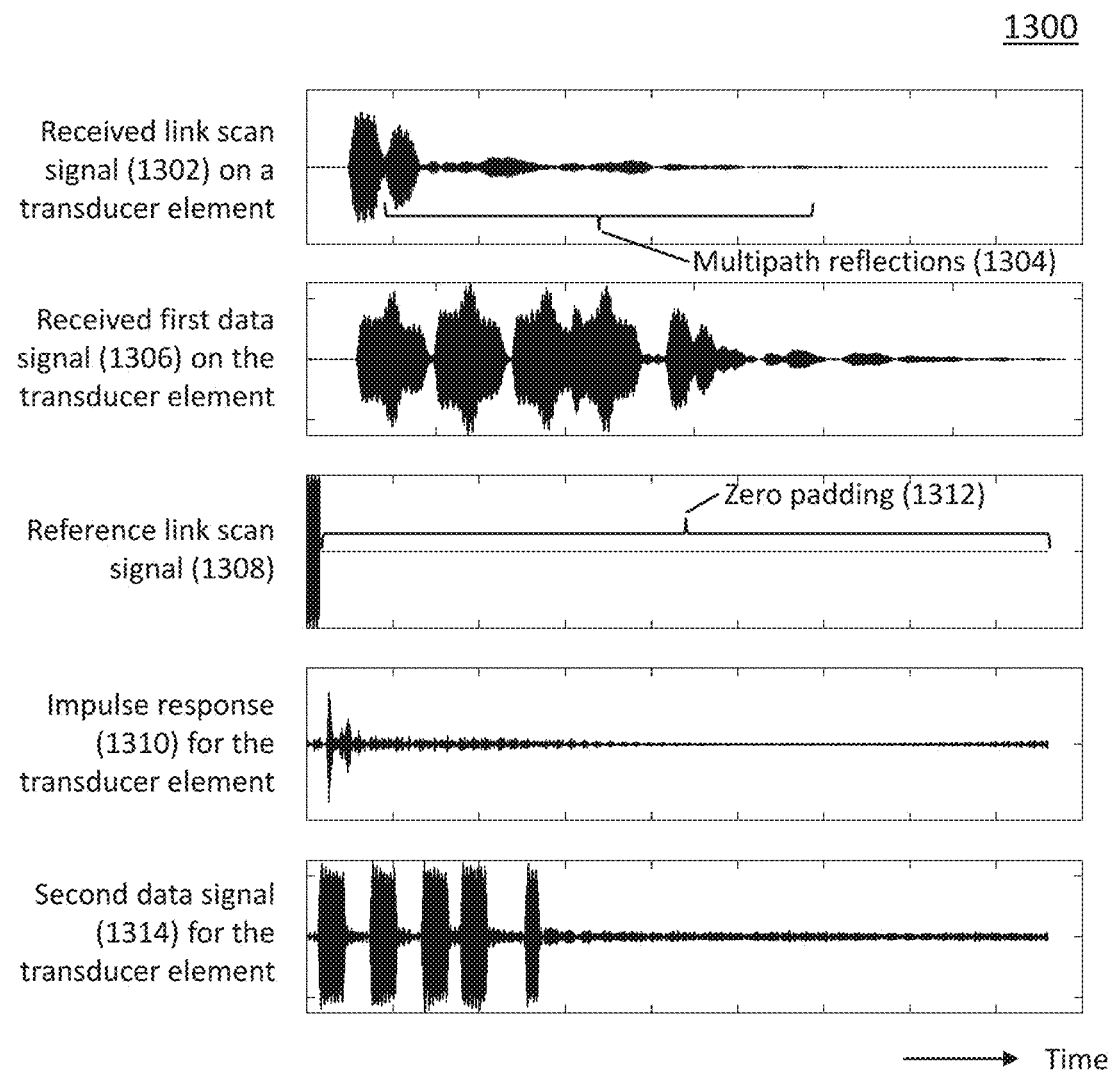
FIG. 13 is a timing diagram of another illustrative variation of signals used in a method of decoding a data signal in a wireless system.

FIG. 13 shows a timing diagram of another variation of signals that may be used in a method of decoding a data signal in a wireless system (1300). A received link scan signal (1302) of a transducer element is shown, which may comprise a received feedback signal pulse (e.g., comprising one or more cycles of a carrier frequency) and its multipath reflections (1304) due to multipath interference in the wireless link. A received first data signal (1306) of the transducer element based on OOK modulation is also shown, which may be corrupted or may have a low signal-to-interference ratio (SIR) or SNR due to multipath interference. It may be challenging to decode such a received first data signal (1306) of the transducer element using conventional OOK demodulation techniques. In some variations, an impulse response (1310) of the transducer element may be determined by deconvolving the received link scan signal (1302) on the transducer element with a reference link scan signal (1308). For instance, the reference link scan signal (1308) may comprise one or more cycles of a carrier frequency representing the link scan signal transmitted by the first device. In some variations, the received first data signal (1306) on the transducer element may be deconvolved with the impulse response (1310) for the transducer element to generate a second data signal (1314) for the transducer element, or an output signal of the deconvolution operation, in order to reject or reduce the multipath interference present in the received first data signal (1306) on the transducer element. In some variations, deconvolution operations described herein may be performed in one or more of time domain and frequency domain. In some variations. OOK demodulation may be further performed on the second data signal (1314) for the transducer element to accurately decode the first data signal (e.g., using operations similar to those described for a combined data signal in FIG. 14).

In some variations, the method of decoding data signals in a wireless system may comprise filtering one or more of the link scan signal, the first data signal and the second data signal using one or more of a band-pass filter, a low-pass filter, a high-pass filter, an all-pass filter, a notch filter, a band-reject filter, combinations thereof, and the like. In some variations, filtering may allow one or more of reduction or rejection of thermal noise, reducing the strength of an interferer, rejecting an interferer, combinations thereof, and the like.

In some variations, methods to combine selected second data signals may be needed to improve the resulting SNR or SIR and, thus, reduce the probability of error in decoding data bits. In some variations, the method of decoding data signals in a wireless system may further comprise selecting two or more of the second data signals for combining into a single data signal based on one or more of a header check, a footer check, relative strengths of the two or more second data signals, relative signal-to-noise ratios of the two or more second data signals, relative strengths of residual interference present in the two or more second data signals, cross-correlation values of the two or more second data signals to a reference second data signal, combinations thereof, and the like. For instance, the selected two or more second data signals may comprise two or more second data signals with the correct header bits (e.g., upon decoding header bits and comparing them to predetermined header bits). Screening second data signals based on a header check may be a computationally efficient way to screen second data signals before combining, in order to achieve a higher SNR or SIR for accurate bit decoding. In some variations, the second data signals or the corresponding transducer elements of the second device may be sorted or ranked according to one or more of relative strengths of the second data signals, relative signal-to-noise ratios of the second data signals, relative signal-to-interference ratios of the second data signals, relative strengths of residual interference present in the second data signals, cross-correlation value of a second data signal to a reference second data signal, combinations thereof, and the like. For instance, the second data signals with high ranks (e.g., high SNR or SIR) may be used for further processing (e.g., signal combining). In some variations, the reference second data signal may be determined based on one or more of the second data signal's amplitude, energy, signal-to-noise ratio or signal-to-interference ratio, the corresponding first data signal's amplitude, energy, signal-to-noise ratio or signal-to-interference ratio, the corresponding link scan signal's amplitude, energy, signal-to-noise ratio or signal-to-interference ratio, an apodization of the corresponding transducer element on which the link scan signal or the first data signal may be received, combinations thereof, and the like. For instance, the reference second data signal may be the second data signal with the highest SNR or SIR.

In some variations, processing the received link scan signals and the received first data signals may further comprise applying matched filtering to one or more of the output signals of the deconvolution (or second data signals). For example, a matched filter comprising a sinusoidal pulse with a duration equal to the bit width may be applied to the output signal of the deconvolution (or second data signal) in order to determine a time reference for decoding and/or to designate the bits as '1' or '0'. In some variations, a matched filter corresponding to a header and/or footer of the data stream may be applied to the output signal of the deconvolution in order to detect the timing and/or presence of the header and/or the footer in the data signal. In some variations, the first data signal may comprise a plurality of headers, footers and/or predetermined bits or words at intermediate locations in the bit stream of the first data signal (e.g., for ease of time synchronization or determining bit locations while performing decoding of data bits on the second device, which may be especially useful for decoding a long data stream comprising a large number of data bits).

In some variations, processing the received link scan signals and the received first data signals may further comprise combining two or more of the output signals of the deconvolution (or second data signals) using one or more of cross-correlation, delaying and summing, combinations thereof, and the like. Such two or more output signals of the deconvolution may be generated by processing the link scan signals and the first data signals received by two or more transducer elements of the transducer array of the second device. Combining signals in this way from different transducer elements may result in improved SIR or SNR for the combined signal compared to the SIRs or SNRs of the individual signals, thereby allowing accurate data recovery or reducing bit error rate (since the number or probability of bit errors may be inversely related to SIR or SNR). In some variations, the time gaps resulting from delaying one signal with respect to the other may be zero padded. In some variations, the method of decoding data signals in a wireless system may comprise combining two or more second data signals or scaled second data signals using one or more of summing, delaying and summing, averaging, delaying and averaging, combinations thereof, and the like, to generate one or more combined data signals. In some variations, the signals to be combined may be sorted, ordered or ranked (e.g., S1, S2, S3, and so on), and different delay and sum combinations may be computed (e.g., S1+S2. S1+S2+S3, and so on). In some variations, such sorting, ordering or ranking may be based upon a cross-correlation value (or similarity) of a signal to a reference signal (e.g., the signal with the highest SNR or SIR). In some variations, the method of decoding data signals in a wireless system may further comprise selecting a combined data signal (e.g., a delayed and summed combination of second data signals) for decoding data bits based on one or more of the combined data signal's amplitude in time domain, the combined data signal's amplitude at a frequency, the combined data signal's energy in one or more frequency bands, the combined data signal's signal-to-noise ratio, combinations thereof, and the like. In some variations, the method may further comprise decoding data bits based at least upon one or more combined data signals using one or more of OOK demodulation. ASK demodulation. PPM demodulation, FSK demodulation. PSK demodulation, QAM demodulation, envelope detection, matched filtering, comparison of the amplitude of the one or more combined data signals to a predetermined threshold, sampling the amplitude of the one or more combined data signals at fixed time offsets, combinations thereof, and the like.

Figure 14:
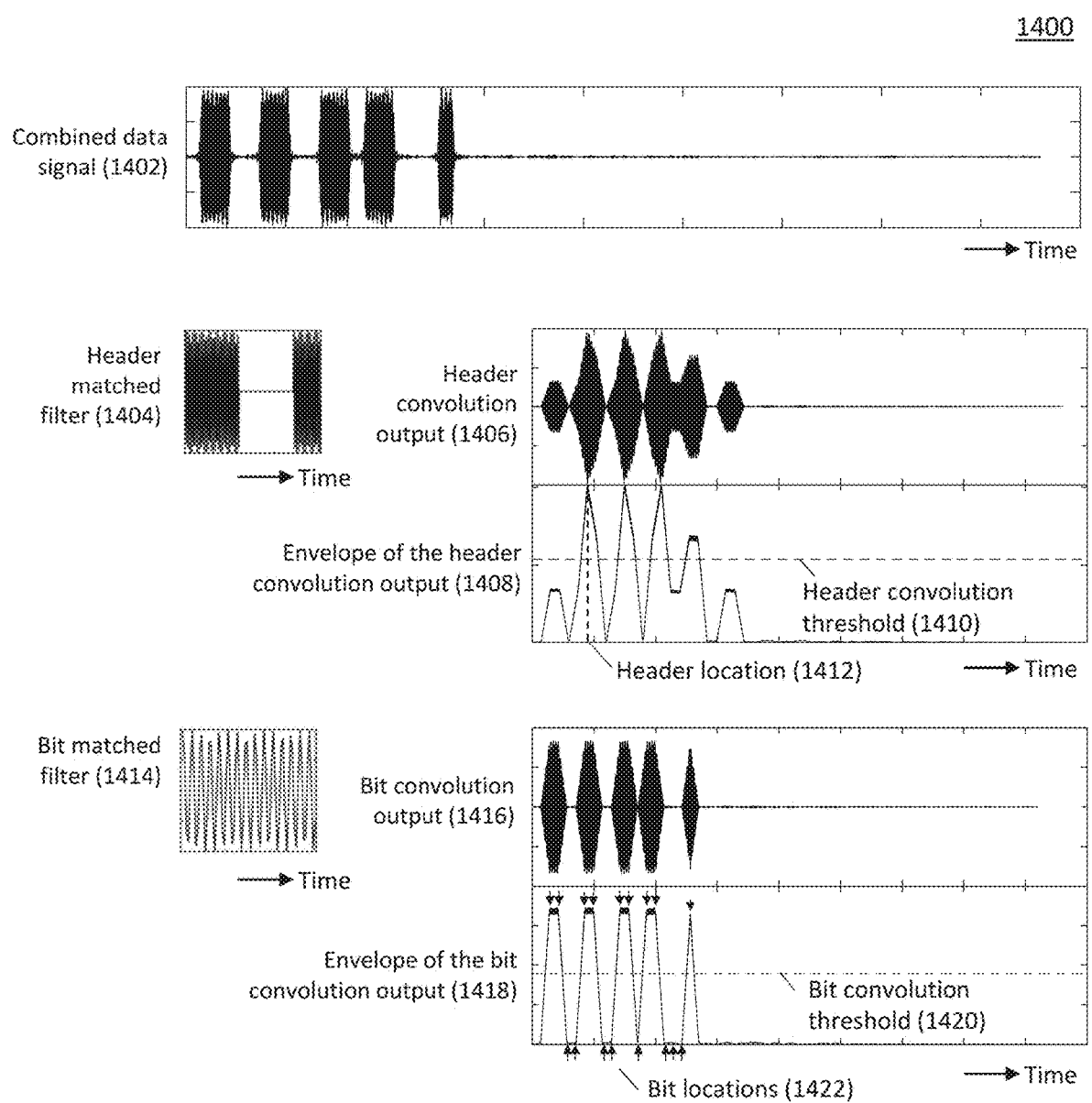
FIG. 14 is a timing diagram of an illustrative variation of signals used in a method of decoding a data signal in a wireless system based on a combined data signal and matched filtering.

FIG. 14 is a timing diagram of an illustrative variation of signals used in a method of decoding a data signal in a wireless system based on a combined data signal and matched filtering, Similar operations, as illustrated by FIG. 14, may be performed on one or more second data signals, such as one or more output signals of deconvolution of one or more first data signals with one or more impulse responses, for decoding the one or more first data signals. A combined data signal (1402) is shown, which may be the result of delaying and summing two or more second data signals (e.g., outputs of deconvolution of the received first data signals with the impulse responses). In some variations, the combined data signal (1402) may be convolved (e.g., in time domain or in frequency domain) with a header matched filter (1404) to generate a header convolution output (1406). In some variations, the header matched filter (1404) may comprise a reference OOK data signal (e.g., comprising one or more pulses) corresponding to predetermined header bits (e.g., 11001) known to be present at the beginning of the first data signal. In some variations, an envelope of the header convolution output (1408) may be determined (e.g., by squaring the header convolution output and applying a low-pass filter, or using other envelope detection techniques). The envelope of the header convolution output (1408) may be compared to a header convolution threshold (1410) to determine a header location (1412) comprising the timing of the first peak of the envelope of the header convolution output (1408) that crosses the header convolution threshold (1410). In some variations, the combined data signal (1402) may be convolved (e.g., in the time domain or in the frequency domain) with a bit matched filter (1414) to generate a bit convolution output (1416). In some variations, the bit matched filter (1414) may comprise a reference OOK data signal (e.g., comprising a single pulse) corresponding to a predetermined single '1' bit. In some variations, an envelope of the bit convolution output (1418) may be determined (e.g., by squaring the header convolution output and applying a low-pass filter, or using other envelope detection techniques). In some variations, bit locations (1422), as illustrated by arrows in FIG. 14, may be determined based on one or more of the header location (1412), the number of header bits, predetermined bit durations (i.e., the duration, number of cycles of a carrier frequency, or a number of clock cycles corresponding to a '1' and/or a '0' bit), combinations thereof, and the like. For instance, a location of a first bit may be determined based on the header location (1412), the number of header bits (e.g., 5) and the duration of a single bit, and locations of other bits may be determined based on fixed timing offsets corresponding to the duration of a single bit starting from the location of the first bit. In some variations, values of the envelope of the bit convolution output (1418) at the bit locations (1422) may be compared to a bit convolution threshold (1420) to decode each bit as a '1' (e.g., for envelope value greater than the bit convolution threshold) or a '0' (e.g., for envelope value smaller than the bit convolution threshold). In some variations, one or more of the header matched filter (1404), the bit matched filter (1414), the header convolution threshold (1410), and the bit convolution threshold (1420), may be predetermined and preloaded (e.g., stored) in a memory of the second device. In some variations, one or more of the header matched filter (1404) and the bit matched filter (1414) may be preloaded (e.g., stored) in a time domain representation and/or a frequency domain representation. In some variations, one or more of the header matched filter (1404), the bit matched filter (1414), the header convolution threshold (1410), and the bit convolution threshold (1420), may be computed by a processor of the second device during execution of a method of decoding a data signal (e.g., upon detecting a carrier frequency of one or more of the link scan signal and the first data signal).

In some variations, the method of decoding data signals in a wireless system may comprise decoding data bits corresponding to one or more second data signals (e.g., the output signal of deconvolution of the first data signal with an impulse response of the wireless system) using one or more of OOK demodulation. ASK demodulation. PPM demodulation. FSK demodulation. PSK demodulation, QAM demodulation, envelope detection, matched filtering, comparison of the amplitude of the one or more second data signals to a predetermined threshold, and sampling the amplitude of the one or more second data signals at fixed time offsets, combinations thereof, and the like. In some variations, the method may further comprise selecting one or more second data signals prior to decoding data bits based on a header check, a footer check, relative strengths of the one or more second data signals, relative signal-to-noise ratios of the one or more second data signals, relative strengths of residual interference present in the one or more second data signals, cross-correlation values of the one or more second data signal to a reference second data signal, combinations thereof, and the like. In some variations, the method may further comprise determining one or more of a majority occurrence (or majority vote) for a bit value, a weighted majority occurrence for a bit value, a mean bit value, a weighted mean bit value among the decoded data bit values corresponding to two or more second data signals, combinations thereof, and the like. In some variations, decoding bits based on majority occurrence may be less computationally intensive compared to combining second data signals to generate a plurality of combined signals, selecting a combined signal with the highest SNR, and decoding bits based on the combined signal with the highest SNR. In some variations, determining the weighted majority occurrence or weighted mean bit value may comprise scaling the bit value by one or more of an apodization of the transducer element on which the corresponding link scan signal or the corresponding first data signal is received, an amplitude, an energy, a signal-to-noise ratio, a time delay, a phase and a multipath time of one or more of the second data signal, the corresponding first data signal, the corresponding link scan signal, combinations thereof, and the like. For instance, an average of decoded '1' and '0' bit values across transducer elements or channels may be computed and compared to a predetermined threshold (e.g., 0.5) for final assignment of a '1' or '0' decoded bit value.

In some variations, the method of decoding data signals in a wireless system may comprise reporting an error or an indication that it may not be possible to decode bits reliably. Such an error or indication may be generated based on one or more of a header check, a footer check, a bit error rate, strengths of the link scan signals, signal-to-noise ratios of the link scan signals, signal-to-interference ratios of the link scan signals, energy of the link scan signals in one or more frequency bands, a moving mean of the link scan signal amplitude, strengths of the first data signals, signal-to-noise ratios of the first data signals, signal-to-interference ratios of the first data signals, energy of the first data signals in one or more frequency bands, a moving mean of the first data signal amplitude, strengths of the second data signals, signal-to-noise ratios of the second data signals, signal-to-interference ratios of the second data signals, energy of the second data signals in one or more frequency bands, a moving mean of the second data signal amplitude, a signal strength of an interferer, a signal strength of multipath interference, a multipath time, apodization of the one or more transducer elements, combinations thereof, and the like.

In some variations, the one or more link scan signals may be transmitted by the first device prior to transmitting the one or more first data signals. For example, in some variations, a plurality of first data signals may be transmitted by the first device after transmitting a link scan signal. In some variations, the one or more first data signals may be transmitted by the first device prior to transmitting the one or more link scan signals. In some variations, the one or more link scan signals may be transmitted by the first device both before and after transmitting the one or more first data signals.

In some variations, the first device may comprise an implantable medical device, the second device may comprise an external wireless device configured to be disposed physically separate from the first device, and the first data signal may comprise an uplink data signal. In some variations, the first device may comprise an external wireless device, the second device may comprise an implantable medical device configured to be disposed physically separate from the first device, and the first data signal may comprise a downlink data signal.

In some variations, the method of decoding data signals in a wireless system may further comprise transmitting one or more of the link scan signal and the first data signal from the first device of the wireless system to the second device of the wireless system at one or more predetermined repetition intervals. In some variations, this may allow reliable data transfer between the first device (e.g., a wireless cardiovascular implantable device) and the second device (e.g., an external wireless device) in the presence of relative motion between the first device and the second device (e.g., due to heart beat and breathing). In some variations, the one or more predetermined repetition intervals may be determined based on a speed of relative motion between the first device and the second device. In some variations, the predetermined repetition interval may correspond to a time duration over which the wireless link may be quasi-static (e.g., the time duration over which a link efficiency may vary by less than about 3 dB) or the first device may be relatively stationary with respect to the first device. In some variations, the first device may transmit one link scan signal (e.g., one feedback signal pulse) corresponding to a plurality of first data signals (e.g., transmit a link scan signal comprising a feedback signal pulse before transmitting a plurality of first data signals, and the like). In some variations, the first device may transmit a plurality of link scan signals corresponding to a single first data signal (e.g., transmit a link scan signal comprising a feedback signal pulse before and after transmitting a first data signal, and the like). In some variations, the method may further comprise transmitting a wireless command from the second device to the first device, and transmitting the link scan signal and the first data signal from the first device to the second device in response to receiving the wireless command by the first device. In some variations, the wireless command may comprise one or more of a wireless signal, a pulse signal, a plurality of pulse signals, a signal with encoded data bits (e.g., using OOK modulation), combinations thereof, and the like. In some variations, one or more of the one or more transmitted link scan signals and the one or more transmitted first data signals may comprise a reflection signal or a backscatter signal in response to receiving a wireless signal transmitted by the second device to the first device.

In some variations, one or more of the transmitted link scan signal and the first data signal may comprise one or more of an ultrasonic signal, an acoustic signal, a vibrational signal, a radio-frequency signal, an electromagnetic signal, a magnetic signal, an electric signal, an optical signal, combinations thereof, and the like.

Figure 15:
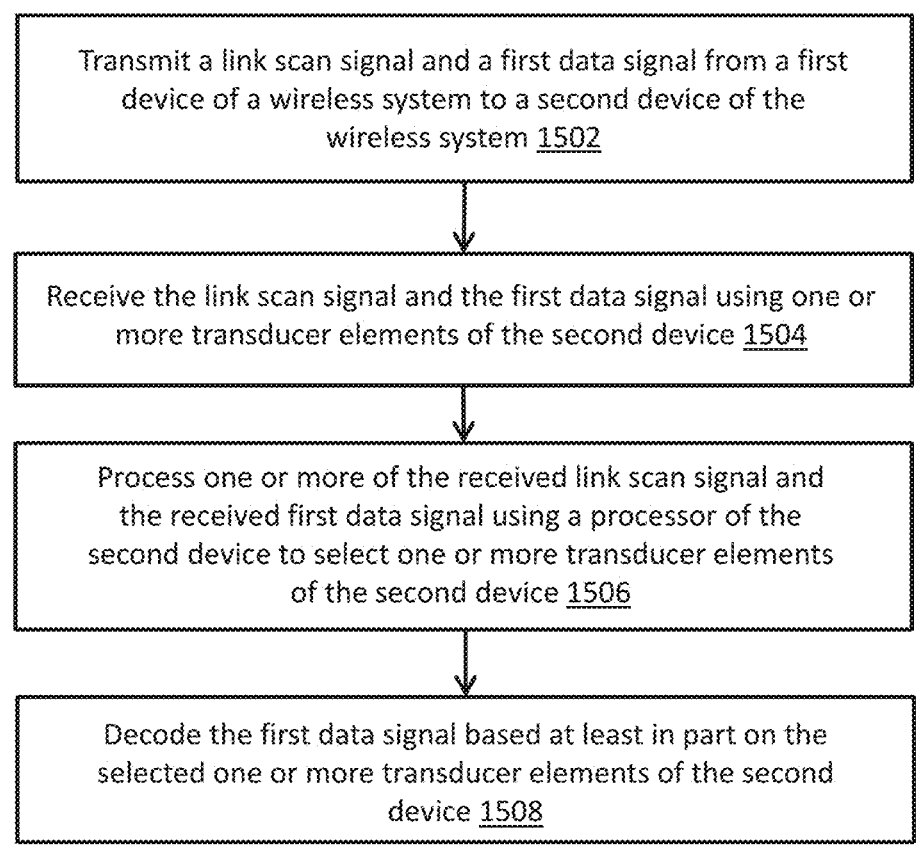
FIG. 15 is a flowchart of another illustrative variation of a method of decoding a data signal in a wireless system.

FIG. 15 is a flowchart that generally describes a variation of a method of decoding a data signal in a wireless system (1500). The method may comprise the steps of transmitting a link scan signal and a first data signal from a first device of the wireless system to a second device of the wireless system (1502), receiving the link scan signal and the first data signal using one or more transducer elements of the second device (1504), processing one or more of the received link scan signal and the received first data signal to select one or more transducer elements of the second device (1506), and decoding the first data signal based at least in part on the selected one or more transducer elements of the second device (1508). In some variations, the link scan signal may comprise one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals, a plurality of pulse signals, combinations thereof, and the like. In some variations, selecting the one or more transducer elements of the second device may be based on one or more of a header check, a footer check, a bit error rate, relative strengths of the link scan signals, relative signal-to-noise ratios of the link scan signals, relative signal-to-interference ratios of the link scan signals, energy of the link scan signals in one or more frequency bands, a moving mean of the link scan signal amplitude, relative strengths of the first data signals, relative signal-to-noise ratios of the first data signals, relative signal-to-interference ratios of the first data signals, energy of the first data signals in one or more frequency bands, a moving mean of the first data signal amplitude, a signal strength of an interferer, a signal strength of multipath interference, a multipath time, an apodization of the one or more transducer elements, combinations thereof, and the like. In some variations, upon selecting the one or more transducer elements of the second device, the received link scan signals and the received first data signals received on the selected transducer elements may be processed using one or more operations described herein (e.g., signal combining, matched filtering, data decoding using OOK demodulation, band-pass filtering, combinations thereof, and the like).

In some variations, bit durations of a data signal may be selected to allow multipath interference to settle (e.g., bit duration greater than a multipath time in the wireless link). In some variations, a high frequency may be used for a data signal (e.g., higher than the frequency of a power signal) to reduce the effect of multipath interference (e.g., due to higher signal attenuation in tissue at higher frequencies). In some variations, the first data signal may comprise pulse position modulation (PPM) and the link scan signal may be used for time synchronization (e.g., to detect a timing of the PPM pulses).

In some variations, the received first data signals may be combined using one or more of summing, delaying and summing, averaging, delaying and averaging, combinations thereof, and the like, to generate one or more combined signals. This may be done in order to improve the SNR or SIR of the combined signal relative to one or more first data signals. In some variations, the delays for delaying and summing or delaying and averaging may be computed based on arrival times of one or more of the received link scan signals and the received first data signals on the one or more transducer elements of the second device. In some variations, envelope detection may be performed on one or more of the received link scan signals and the received first data signals, and the envelope may be compared to a predetermined threshold to detect an onset, arrival time or rising edge of the signals, which may be used for delaying the signals before combining and summing the signals.

Figure 16:
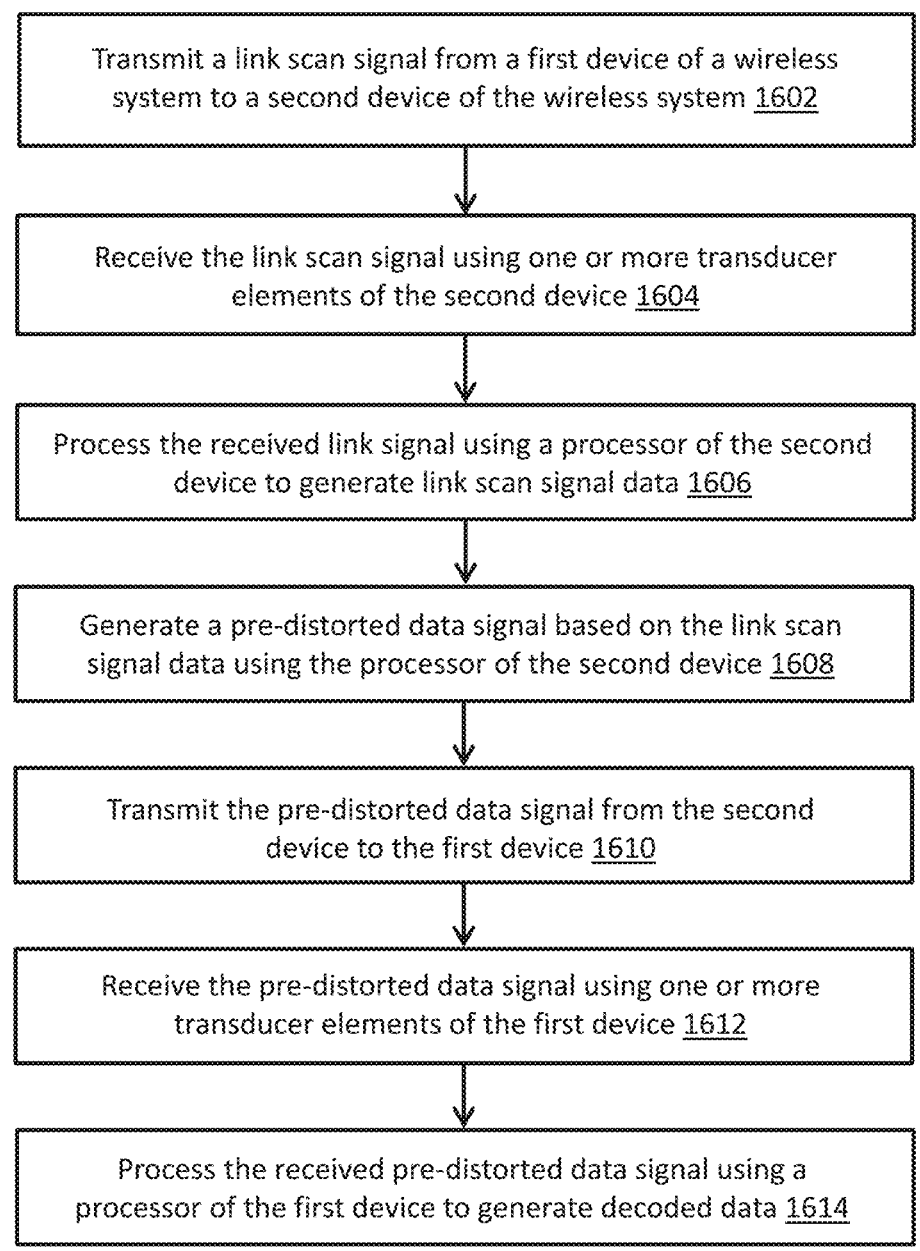
FIG. 16 is a flowchart of an illustrative variation of a method of decoding a data signal in a wireless system based on a pre-distorted data signal.

FIG. 16 shows a flowchart of yet another variation of a method of decoding a data signal in a wireless system (1600). The method (1600) may comprise the steps of transmitting a link scan signal from a first device of the wireless system to a second device of the wireless system (1602), receiving the link scan signal using one or more transducer elements of the second device (1604), processing the received link scan signal using a processor of the second device to generate link scan signal data (1606), generating a pre-distorted data signal based on the link scan signal data using the processor of the second device (1608), transmitting the pre-distorted data signal from the second device to the first device (1610), receiving the pre-distorted data signal using one or more transducer elements of the first device (1612), and processing the received pre-distorted data signal using a processor of the first device to generate decoded data (1614). The link scan signal, the data signal, the link scan signal data, the transducer elements and the processor, as described herein, are applicable to any of the methods described herein.

In some variations, the link scan signal may comprise an impulse signal, and generating the pre-distorted data signal may comprise performing deconvolution of a data signal (e.g., an ideal OOK data waveform without any multipath interference) with the received link scan signal. In some variations, the link scan signal data may comprise an impulse response of the wireless system, and generating the pre-distorted data signal may comprise performing deconvolution of a data signal (e.g., an ideal OOK data waveform without any multipath interference) with the impulse response of the wireless system. When the pre-distorted data signal travels from the second device to the first device, it may undergo convolution with the impulse response of the wireless system. Thus, the received pre-distorted data signal, that is received by the first device, may resemble the original data signal (i.e., the ideal OOK data waveform without any multipath interference), thereby, allowing mitigation of any signal corruption due to multipath interference. In some variations, time reversal may be applied to the one or more received link scan signals, and the resulting one or more time reversed signals may be used to transmit one or more data signals to the first device, as opposed to generating and transmitting the pre-distorted data signal.

In some variations, the first device may comprise an implantable medical device, the second device may comprise an external wireless device configured to be disposed physically separate from the first device, and the pre-distorted data signal may comprise a downlink data signal. In some variations, the first device may comprise an external wireless device, the second device may comprise an implantable medical device configured to be disposed physically separate from the first device, and the pre-distorted data signal may comprise an uplink data signal.

Figure 17:
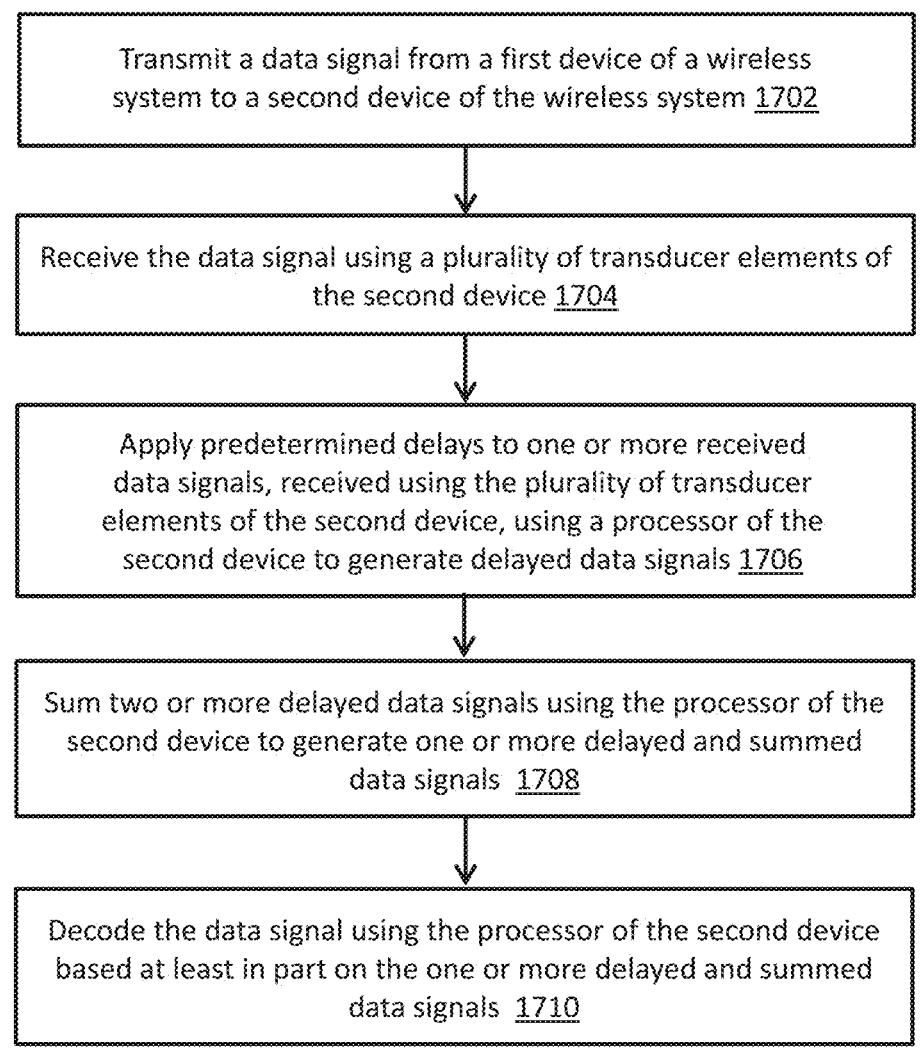
FIG. 17 is a flowchart of an illustrative variation of a method of decoding a data signal in a wireless system based on a delayed and summed data signal.

FIG. 17 shows a flowchart of yet another variation of a method of decoding a data signal in a wireless system (1700). The method (1700) may comprise the steps of transmitting a data signal from a first device of the wireless system to a second device of the wireless system (1702), receiving the data signal using a plurality of transducer elements of the second device (1704), applying predetermined delays to one or more received data signals, received using the plurality of transducer elements of the second device, using a processor of the second device to generate delayed data signals (1706), summing two or more delayed data signals using the processor of the second device to generate one or more delayed and summed data signals (1708), and decoding the data signal using the processor of the second device based at least in part on the one or more delayed and summed data signals (1710). The data signal, the transducer elements, and the processor, as described herein, are applicable to any of the methods described herein.

In some variations, the method (1700) may further comprise transmitting a feedback signal from the first device to the second device prior to transmitting the data signal, receiving the feedback signal using one or more transducer elements of the second device, processing the received feedback signal using the processor of the second device to generate feedback signal data, and computing the predetermined delays based at least in part on the feedback signal data. In some variations, the method (1700) may further comprise transmitting a link scan signal from the first device to the second device prior to transmitting the data signal, receiving the link scan signal using one or more transducer elements of the second device, processing the received link scan signal using the processor of the second device to generate link scan signal data, and computing the predetermined delays based at least in part on the link scan signal data. The feedback signal, the link scan signal, the data signal, the transducer elements, the processor, the feedback signal data, and the link scan signal data, as described herein, are applicable to any of the methods described herein.

In some variations, the first device may comprise an implantable medical device, the second device may comprise an external wireless device configured to be disposed physically separate from the first device, and the data signal may comprise an uplink data signal. In some variations, the first device may comprise an external wireless device, the second device may comprise an implantable medical device configured to be disposed physically separate from the first device, and the data signal may comprise a downlink data signal.

In some variations, the processor of the second device may be configured to select one or more transducer elements of the second device for further processing of one or more of the link scan signal and the first data signal based on one or more properties of one or more of the link scan signal and the first data signal.

In some variations, upon decoding a data signal, a processor of one or more of the second device and the first device of the wireless system may be configured to perform one or more of error detection, error correction, combinations thereof, and the like (e.g., using error correcting codes or ECC, cyclic redundancy check or CRC, and the like). In some variations, upon detecting a data signal, a processor of one or more of the second device and the first device may be configured to generate one or more of an acknowledgment signal (ACK) and a negative acknowledgment signal (NACK). For instance, a processor of the second device may be configured to generate an ACK signal upon detecting zero bit errors in the decoded first data signal (e.g., after performing a cyclic redundancy check), and transmit the ACK signal to the first device using the transducer array configuration of the second device as described herein. Variations of the data signal, as described herein, may be applicable to one or more of the ACK signal and the NACK signal.

C. Calibrating a Wireless System

In some variations, a wireless implantable device may comprise a transducer having a resonance frequency, and a wireless transmitter comprising an oscillator circuit having an oscillator frequency. In some variations, the oscillator frequency may vary significantly across different wireless implantable device due to device-to-device variations (e.g., due to chip-to-chip variations caused by variations in the integrated circuit manufacturing process). In some devices, the resonance frequency of the transducer of the wireless implantable device may not match the oscillator frequency due to its excessive variations, which may result in a low output power for any uplink signals transmitted by the wireless implantable device. In such cases, calibration and/or adjustment of the oscillator frequency may be desired. However, conventional methods of calibrating the oscillator frequency by testing the wireless implantable device and/or its components on the bench may be time-consuming and/or expensive and may not account for overall wireless system performance. Solutions are provided herein to mitigate this challenge.

Figure 18:
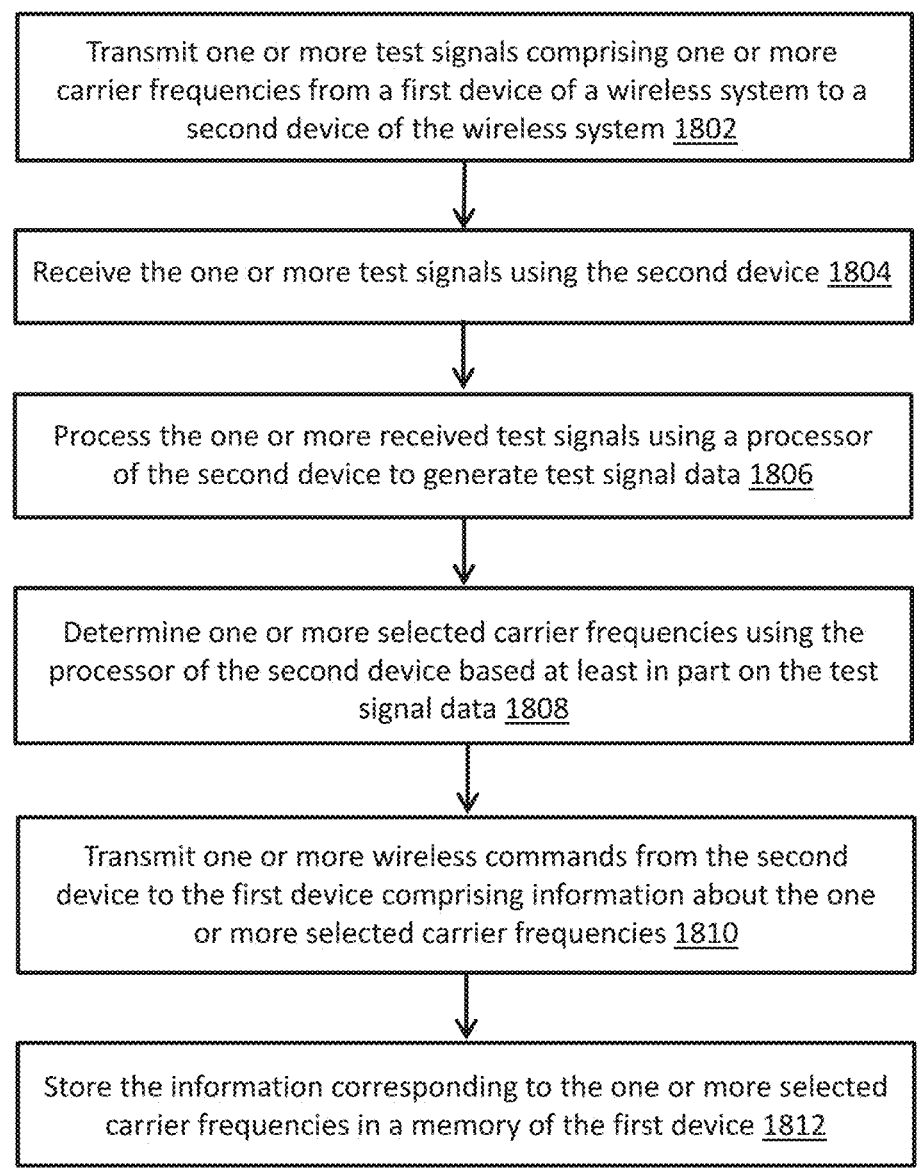
FIG. 18 is a flowchart of an illustrative variation of a method of calibrating a wireless system.

FIG. 18 is a flowchart that generally describes a variation of a method of calibrating a wireless system (1800). The method (1800) may comprise the steps of transmitting one or more test signals comprising one or more carrier frequencies from a first device of the wireless system to a second device of the wireless system (1802), receiving the one or more test signals using the second device (1804), processing the one or more received test signals using a processor of the second device to generate test signal data (1806), determining one or more selected carrier frequencies using the processor of the second device based at least in part on the test signal data (1808), transmitting one or more wireless commands from the second device to the first device comprising information corresponding to the one or more selected carrier frequencies (1810), and storing information corresponding to the one or more selected carrier frequencies in a memory of the first device (1812). A test signal may be any signal transmitted from a device of a wireless system to another device of the wireless system in order to test one or more characteristics of the wireless link between the two devices. For example, a test signal may comprise a sinusoidal and/or a rectangular signal comprising one or more cycles of a carrier frequency of the test signal, or one or more cycles of an oscillator frequency of the first device (e.g., a wireless implantable device). In some variations, test signal data may comprise any property of the test signal (e.g., amplitude, signal strength, frequency, phase, and the like) and/or any characteristic of the wireless link (e.g., link efficiency).

In some variations, the method (1800) may further comprise transmitting a wireless signal comprising the one or more selected carrier frequencies from the first device to the second device. In some variations, the transmitted wireless signal may comprise one or more of a feedback signal, a link scan signal, an uplink data signal, combinations thereof, and the like.

In some variations, determining one or more selected carrier frequencies may comprise determining one or more carrier frequencies at which a parameter of the received test signal may have a value greater than a predetermined threshold. In some variations, the parameter of the received test signal may comprise one or more of a signal strength, a signal amplitude, a signal power, a signal energy, a signal-to-noise ratio, a signal-to-interference ratio, a link efficiency, a link gain, combinations thereof, and the like. In some variations, the memory of the first device may comprise one or more of a non-volatile memory, a volatile memory, combinations thereof, and the like. In some variations, a non-volatile memory may be configured for permanently storing information corresponding to the one or more selected carrier frequencies and/or for storing information corresponding to the one or more selected carrier frequencies until a next calibration operation.

Figure 19:
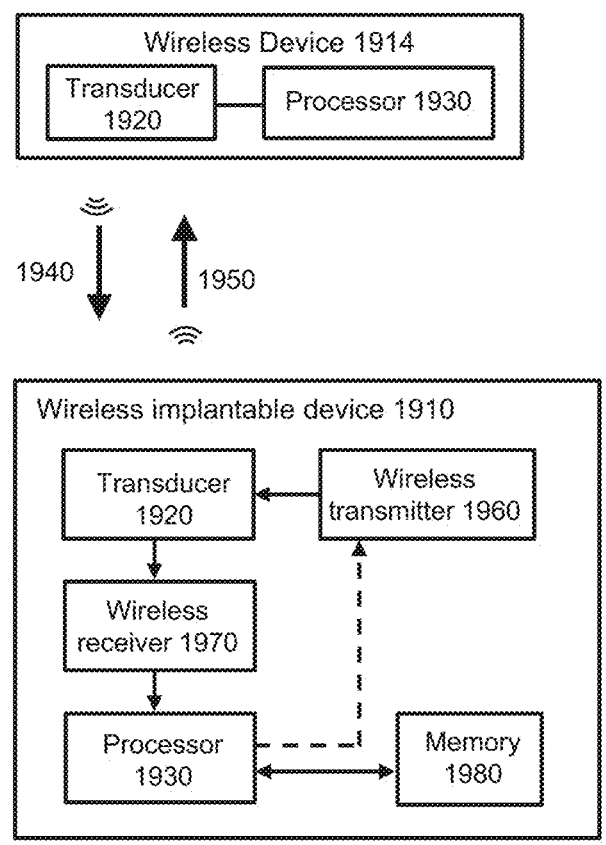
FIG. 19 is a schematic block diagram of an illustrative variation of a wireless system configured for calibration.

FIG. 19 shows a schematic block diagram of a wireless system configured for calibration (1900). The system (1900) may comprise a wireless device (1914) comprising a transducer (1920) and a processor (1930). The system may further comprise a wireless implantable device (1910) comprising a transducer (1920), a wireless transmitter (1960), a wireless receiver (1970), a processor (1930), and a memory (1980). In some variations, the processor (1930) of the wireless implantable device (1910) may be configured to control the wireless transmitter (1960) to transmit one or more test signals (1950) comprising one or more carrier frequencies via the transducer (1920) of the wireless implantable device (1910). The transducer (1920) of the wireless device (1914) may be configured to receive the one or more test signals (1950). The processor (1930) of the wireless device (1914) may be configured to process the one or more received test signals (1950) to generate test signal data. In some variations, the processor (1930) of the wireless device (1914) may be further configured to determine one or more selected carrier frequencies based at least in part on the test signal data. The processor (1930) of the wireless device (1914) may be further configured to control the transducer (1920) of the wireless device (1914) to transmit one or more wireless commands to the wireless implantable device (1910) via one or more downlink signals (1940), wherein the one or more wireless commands may comprise information corresponding to the one or more selected carrier frequencies. The wireless receiver (1970) of the wireless implantable device (1910) may be configured to receive the one or more wireless commands via the transducer (1920). In some variations, the processor (1930) may be configured to store the information corresponding to the one or more selected carrier frequencies in the memory (1980) of the wireless implantable device (1910). Optionally, in some variations, the processor (1930) may be configured to control the wireless transmitter (1960) to transmit one or more wireless signals at one or more selected carrier frequencies.

Exemplary Embodiments

Embodiment A1. A system configured to exchange wireless power or data, comprising:
- a first device configured to transmit a feedback signal with a first duration; and
- a second device comprising a transducer array and a processor, wherein
- the transducer array is configured to receive the feedback signal on one or more transducer elements of the transducer array for a second duration,
- the processor is configured to process the feedback signal received in the second duration by one or more transducer elements of the transducer array to generate feedback signal data, and determine a transducer array configuration based at least in part on the feedback signal data, and
- the second device is configured to exchange one or more wireless signals with the first device using the transducer array configuration.

Embodiment A2. The system of claim A1, wherein the second duration is greater than the first duration.

Embodiment A3. The system of claim A1, wherein the processor is further configured to detect an onset of the received feedback signal on one or more transducer elements of the transducer array using one or more of envelope detection, predetermined timing, coherent detection, and comparison of the received feedback signal amplitude to a predetermined threshold level.

Embodiment A4. The system of claim A1, wherein the feedback signal data comprises one or more of an absolute amplitude or magnitude, a relative amplitude or magnitude, an absolute signal strength, a relative signal strength, signal energy in one or more frequency bands, an apodization, an absolute phase, a relative phase, an absolute time delay, a relative time delay, an absolute time of arrival, a relative time of arrival, a frequency, a time duration, number of cycles, an absolute signal-to-noise ratio, and a relative signal-to-noise ratio of the feedback signal received within the second duration by one or more transducer elements of the transducer array.

Embodiment A5. The system of claim A1, wherein the transducer array configuration comprises one or more of a selected set of transducer elements, apodizations, signal strengths, voltage levels, current levels, pulse widths, pulse width modulations, duty cycles, phases, time delays, frequencies and transmit durations applied to one or more transducer elements of the transducer array for transmitting wireless signals to the first device.

Embodiment A6. The system of claim A5, wherein the phases applied to the one or more transducer elements of the transducer array for transmitting wireless signals to the first device are based on one or more of the relative phases of the received feedback signal in the second duration at a predetermined frequency and the time of arrival of the feedback signal received on the one or more transducer elements.

Embodiment A7. The system of claim A5, wherein the time delays applied to the one or more transducer elements of the transducer array for transmitting wireless signals to the first device are based on one or more of the relative phases of the received feedback signal in the second duration at a predetermined frequency and the time of arrival of the feedback signal received on the one or more transducer elements.

Embodiment A8. The system of claim A1, wherein the received feedback signal comprises a time duration and a settled amplitude.

Embodiment A9. The system of claim A1, wherein the feedback signal comprises one or more of an impulse signal and a pulse signal.

Embodiment A10. The system of claim A1, wherein the processor is configured to process the feedback signal or determine the transducer array configuration using one or more of a time domain analysis, a frequency domain analysis, and an interpolation analysis.

Embodiment A11. The system of claim A10, wherein the time domain analysis comprises one or more of cross-correlation and time reversal.

Embodiment A12. The system of claim A10, wherein the frequency domain analysis comprises computing one or more of a Fourier transform, a discrete Fourier transform (DFT) and a discrete-time Fourier transform (DTFT) at one or more predetermined frequencies.

Embodiment A13. The system of claim A12, wherein the processor is configured to use a fast Fourier transform (FFT) algorithm for computing one or more of the Fourier transform, the discrete Fourier transform (DFT) and the discrete-time Fourier transform (DTFT) at the one or more predetermined frequencies.

Embodiment A14. The system of claim A12, wherein the one or more predetermined frequencies are based on one or more feedback signal frequencies.

Embodiment A15. The system of claim A12, wherein the processor is configured to determine the one or more predetermined frequencies based on one or more of a time domain analysis and a frequency domain analysis of the feedback signal received in one or more of the first duration, the second duration and a third duration by one or more transducer elements of the transducer array.

Embodiment A16. The system of claim A1, wherein the processor is configured to use at least one of the feedback signal data and a predetermined power of the transmitted feedback signal to determine one or more of a link efficiency and transmit power for transmitting wireless signals to the first device.

Embodiment A17. The system of claim A1, wherein the one or more wireless signals exchanged with the first device comprise a first set of frequencies and the feedback signal comprises a second set of frequencies, the first set of frequencies different from the second set of frequencies.

Embodiment A18. The system of claim A1, wherein a first set of transducer elements configured to receive the feedback signal comprises one or more common transducer elements with a second set of transducer elements corresponding to the transducer array configuration configured to exchange wireless signals with the first device.

Embodiment A19. The system of claim A1, wherein a first set of transducer elements configured to receive the feedback signal comprises different transducer elements than a second set of transducer elements corresponding to the transducer array configuration configured to exchange wireless signals with the first device.

Embodiment A20. The system of claim A1, wherein the first device comprises an implantable medical device, and the second device comprises an external wireless device configured to be disposed physically separate from the first device.

Embodiment A21. The system of claim A1, wherein the first device comprises an external wireless device, and the second device comprises an implantable medical device configured to be disposed physically separate from the first device.

Embodiment A22. The system of claim A1, wherein the first device is configured to transmit the feedback signal at one or more predetermined repetition intervals.

Embodiment A23. The system of claim A1, wherein the second device is further configured to transmit a wireless command to the first device, and the first device is configured to transmit the feedback signal in response to receiving the wireless command.

Embodiment A24. The system of claim A1, wherein the transmitted feedback signal comprises a reflection signal or a backscatter signal in response to receiving a wireless signal transmitted by the second device to the first device.

Embodiment A25. The system of claim A1, wherein the transmitted feedback signal comprises one or more of an ultrasonic signal, an acoustic signal, a vibrational signal, a radio-frequency signal, an electromagnetic signal, a magnetic signal, an electric signal, and an optical signal.

Embodiment A26. The system of claim A1, wherein the first device is further configured to transmit one or more data signals to the second device.

Embodiment A27. The system of claim A26, wherein the processor is further configured to select one or more transducer elements of the transducer array of the second device for processing the one or more data signals.

Embodiment A28. The system of claim A27, wherein the processor is configured to select the one or more transducer elements of the transducer array of the second device based on one or more of a signal strength of the received feedback signal, a signal-to-noise ratio of the received feedback signal, an energy of the received feedback signal in one or more frequency bands, an apodization of the transducer element, a moving mean of the feedback signal amplitude, a signal strength of an interferer, a signal strength of multipath interference, and a multipath time.

Embodiment B1. A method of exchanging wireless signals in a wireless system, comprising:
  transmitting a feedback signal with a first duration from a first device of the wireless system to a second device of the wireless system;
  receiving the feedback signal for a second duration using one or more transducer elements of a transducer array of the second device;
  processing the feedback signal received in the second duration using one or more transducer elements of the transducer array to generate feedback signal data using a processor of the second device;
  determining a transducer array configuration of the second device based at least in part on the feedback signal data using the processor of the second device; and
  exchanging one or more wireless signals with the first device using the transducer array configuration of the second device.

Embodiment B2. The method of claim B1, wherein the second duration is greater than the first duration.

Embodiment B3. The method of claim B1, further comprising detecting an onset of the received feedback signal on one or more transducer elements of the transducer array using one or more of envelope detection, predetermined timing, coherent detection, and comparison of the received feedback signal amplitude to a predetermined threshold level.

Embodiment B4. The method of claim B1, wherein the feedback signal data comprises one or more of an absolute amplitude or magnitude, a relative amplitude or magnitude, an absolute signal strength, a relative signal strength, signal energy in one or more frequency bands, an apodization, an absolute phase, a relative phase, an absolute time delay, a relative time delay, an absolute time of arrival, a relative time of arrival, a frequency, a time duration, number of cycles, an absolute signal-to-noise ratio, and a relative signal-to-noise ratio of the feedback signal received within the second duration by one or more transducer elements of the transducer array.

Embodiment B5. The method of claim B1, wherein the transducer array configuration comprises one or more of a selection of a set of transducer elements, an apodization, a signal strength, a voltage level, a current level, a pulse width, pulse width modulation, a duty cycle of a signal, a phase, a time delay, a frequency and a transmit duration applied to one or more transducer elements of the transducer array for transmitting wireless signals to the first device.

Embodiment B6. The method of claim B5, wherein the phases applied to the one or more transducer elements of the transducer array for transmitting wireless signals to the first device are based on one or more of the relative phases of the received feedback signal in the second duration at a predetermined frequency and the time of arrival of the feedback signal received using the one or more transducer elements.

Embodiment B7. The method of claim B5, wherein the time delays applied to the one or more transducer elements of the transducer array for transmitting wireless signals to the first device are based on one or more of the relative phases of the received feedback signal in the second duration at a predetermined frequency and the time of arrival of the feedback signal received using the one or more transducer elements.

Embodiment B8. The method of claim B1, wherein the received feedback signal comprises a time duration and a settled amplitude.

Embodiment B9. The method of claim B1, wherein the feedback signal comprises one or more of an impulse signal and a pulse signal.

Embodiment B10. The method of claim B1, wherein processing the feedback signal or determining the transducer array configuration of the second device comprises one or more of a time domain analysis, a frequency domain analysis, and an interpolation analysis.

Embodiment B11. The method of claim B10, wherein the time domain analysis comprises one or more of cross-correlation and time reversal.

Embodiment B12. The method of claim B10, wherein the frequency domain analysis comprises computing one or more of a Fourier transform, a discrete Fourier transform (DFT) and a discrete-time Fourier transform (DTFT) at one or more predetermined frequencies.

Embodiment B13. The method of claim B12, wherein computing one or more of the Fourier transform, the discrete Fourier transform (DFT) and the discrete-time Fourier transform (DTFT) at the one or more predetermined frequencies comprises using a fast Fourier transform (FFT) algorithm.

Embodiment B14. The method of claim B12, wherein the one or more predetermined frequencies are based on one or more feedback signal frequencies.

Embodiment B15. The method of claim B12, further comprising determining the one or more predetermined frequencies based on one or more of a time domain analysis and a frequency domain analysis of the feedback signal received in one or more of the first duration, the second duration and a third duration using one or more transducer elements of the transducer array.

Embodiment B16. The method of claim B1, wherein determining a transducer array configuration of the second device comprises using at least one of the feedback signal data and a predetermined power of the transmitted feedback signal to determine one or more of a link efficiency and a transmit power for transmitting wireless signals to the first device.

Embodiment B17. The method of claim B1, wherein the one or more wireless signals exchanged with the first device comprise a first set of frequencies and the feedback signal comprises a second set of frequencies, the first set of frequencies different from the second set of frequencies.

Embodiment B18. The method of claim B1, wherein a first set of transducer elements configured to receive the feedback signal comprises one or more common transducer elements with a second set of transducer elements corresponding to the transducer array configuration configured to exchange wireless signals with the first device.

Embodiment B19. The method of claim B1, wherein a first set of transducer elements configured to receive the feedback signal comprises different transducer elements than a second set of transducer elements corresponding to the transducer array configuration configured to exchange wireless signals with the first device.

Embodiment B20. The method of claim B1, wherein the first device comprises an implantable medical device, and the second device comprises an external wireless device configured to be disposed physically separate from the first device.

Embodiment B21. The method of claim B1, wherein the first device comprises an external wireless device, and the second device comprises an implantable medical device configured to be disposed physically separate from the first device.

Embodiment B22. The method of claim B1, further comprising transmitting the feedback signal from the first device at one or more predetermined repetition intervals.

Embodiment B23. The method of claim B1, further comprising transmitting a wireless command from the second device to the first device and transmitting the feedback signal from the first device to the second device in response to receiving the wireless command.

Embodiment B24. The method of claim B1, wherein the transmitted feedback signal comprises a reflection signal or a backscatter signal in response to receiving a wireless signal transmitted by the second device to the first device.

Embodiment B25. The method of claim B1, wherein the transmitted feedback signal comprises one or more of an ultrasonic signal, an acoustic signal, a vibrational signal, a radio-frequency signal, an electromagnetic signal, a magnetic signal, an electric signal, and an optical signal.

Embodiment B26. The method of claim B1, further comprising transmitting one or more data signals from the first device to the second device.

Embodiment B27. The method of claim B26, further comprising selecting one or more transducer elements of the transducer array of the second device for processing the one or more data signals using the processor of the second device.

Embodiment B28. The method of claim B27, comprising selecting the one or more transducer elements of the transducer array of the second device based on one or more of a signal strength of the received feedback signal, a signal-to-noise ratio of the received feedback signal, an energy of the received feedback signal in one or more frequency bands, an apodization of the transducer element, a moving mean of the feedback signal amplitude, a signal strength of an interferer, a signal strength of multipath interference, and a multipath time.

Embodiment C1. A system configured for wireless data communication, comprising:
 a first device configured to transmit a link scan signal and a first data signal; and
 a second device comprising one or more transducer elements, and a processor, wherein
  the one or more transducer elements are configured to receive the link scan signal and the first data signal from the first device, and
  the processor is configured to process the received link scan signal and the received first data signal to generate a second data signal, and decode the first data signal based at least in part on the second data signal.

Embodiment C2. The system of claim C1, wherein the link scan signal comprises one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals and a plurality of pulse signals.

Embodiment C3. The system of claim C2, wherein the pulse signal or the feedback signal comprises one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

Embodiment C4. The system of claim C1, wherein the first data signal comprises one or more of on-off keying (OOK) modulation, amplitude-shift keying (ASK) modulation, pulse-position modulation (PPM), frequency-shift keying (FSK) modulation, phase-shift keying (PSK) modulation, and quadrature amplitude modulation (QAM).

Embodiment C5. The system of claim C1, wherein the processor is further configured to select one or more time durations of one or more of the received link scan signal and the received first data signal based on one or more of a predetermined timing, signal onset detection, detection of one or more of a signal rising edge and a signal falling edge, detection of one or more of a header component and a footer component of a signal, a multipath time and a drift in a frequency of one or more of the received link scan signal and the received first data signal.

Embodiment C6. The system of claim C1, wherein the processor is configured to process the received link scan signal to determine a scaled impulse response of the wireless system.

Embodiment C7. The system of claim C6, wherein the link scan signal comprises a feedback signal and the processor is configured to determine a scaled impulse response of the wireless system by deconvolving the scaled received feedback signal with a scaled reference feedback signal using one or more of frequency domain computation and time domain computation.

Embodiment C8. The system of claim C7, wherein one or more of the scaled impulse response, the scaled received feedback signal, and the scaled reference feedback signal are scaled by one or more of an amplitude in the time domain, an amplitude at a frequency, an energy in one or more frequency bands, a signal-to-noise ratio for one or more of the impulse response, the received feedback signal, and the reference feedback signal, an apodization of the corresponding transducer element, a predetermined scaling factor, and a normalization scaling factor.

Embodiment C9. The system of claim C7, wherein the second device comprises a memory preloaded with one or more of a frequency domain representation and a time domain representation of the scaled reference feedback signal.

Embodiment C10. The system of claim C7, wherein the processor is further configured to generate one or more of a frequency domain representation and a time domain representation of the scaled reference feedback signal based on one or more properties of one or more of the received link scan signal and the received first data signal.

Embodiment C11. The system of claim C10, wherein the one or more properties of one or more of the received link scan signal and the received first data signal comprise one or more of a frequency, a duration, a number of cycles, an amplitude, a phase, and a time of arrival.

Embodiment C12. The system of claim C6, wherein the processor is configured to process the received link scan signal and the received first data signal by deconvolving a scaled received first data signal with one or more of the scaled impulse response and a scaled received link scan signal, using one or more of a frequency domain analysis and a time domain analysis, to generate the second data signal.

Embodiment C13. The system of claim C12, wherein one or more of the scaled received first data signal, the scaled impulse response and the scaled received link scan signal are scaled by an amplitude in the time domain, an amplitude at a frequency, an energy in one or more frequency bands, a signal-to-noise ratio for one or more of the received first data signal, the impulse response, and the received link scan signal, an apodization of the corresponding transducer element, a predetermined scaling factor, and a normalization scaling factor.

Embodiment C14. The system of claim C1, wherein the processor is configured to process the received link scan signal and the received first data signal by deconvolving a scaled received first data signal with a scaled received link scan signal using one or more of a frequency domain analysis and a time domain analysis, to generate the second data signal.

Embodiment C15. The system of claim C14, wherein the link scan signal comprises one or more of an impulse signal, a feedback signal, a pulse signal, a pulse signal representing a single data bit of the first data signal, a pulse signal representing a plurality of data bits of the first data signal, a plurality of impulse signals and a plurality of pulse signals.

Embodiment C16. The system of claim C1, wherein the processor is further configured to filter one or more of the link scan signal, the first data signal and the second data signal using one or more of a band-pass filter, a low-pass filter, a high-pass filter, an all-pass filter, a notch filter and a band-reject filter.

Embodiment C17. The system of claim C1, wherein the processor is further configured to select two or more second data signals for signal combining based on one or more of a header check, a footer check, relative strengths of the two or more second data signals, relative signal-to-noise ratios of the two or more second data signals, relative signal-to-interference ratios of the two or more second data signals, relative strengths of residual interference present in the two or more second data signals, and cross-correlation values of the two or more second data signals to a reference second data signal.

Embodiment C18. The system of claim C17, wherein the processor is further configured to determine the reference second data signal based on one or more of the second data signal's amplitude, energy, signal-to-noise ratio or signal-to-interference ratio, the corresponding first data signal's amplitude, energy, signal-to-noise ratio or signal-to-interference ratio, the corresponding link scan signal's amplitude, energy, signal-to-noise ratio or signal-to-interference ratio, and an apodization of the corresponding transducer element on which the link scan signal or the first data signal is received.

Embodiment C19. The system of claim C1, wherein the processor is further configured to combine two or more scaled second data signals using one or more of summing, delaying and summing, averaging, and delaying and averaging to generate one or more combined data signals.

Embodiment C20. The system of claim C19, wherein the scaled second data signal is scaled by one or more of an amplitude in the time domain, an amplitude at a frequency, an energy in one or more frequency bands, a signal-to-noise ratio of the second data signal, an apodization of the corresponding transducer element, a predetermined scaling factor, and a normalization scaling factor.

Embodiment C21. The system of claim C19, wherein the processor is further configured to select a combined data signal for decoding data bits based on one or more of the combined data signal's amplitude in time domain, the combined data signal's amplitude at a frequency, the combined data signal's energy in one or more frequency bands, and the combined data signal's signal-to-noise ratio.

Embodiment C22. The system of claim C19, wherein the processor is further configured to decode data bits based at least upon one or more combined data signals using one or more of OOK demodulation, ASK demodulation, PPM demodulation, FSK demodulation, PSK demodulation, QAM demodulation, envelope detection, matched filtering, comparison of the amplitude of the one or more combined data signals to a predetermined threshold, and sampling the amplitude of the one or more combined data signals at fixed time offsets.

Embodiment C23. The system of claim C1, wherein the processor is further configured to decode data bits corresponding to one or more second data signals using one or more of OOK demodulation, ASK demodulation, PPM demodulation, FSK demodulation, PSK demodulation, QAM demodulation, envelope detection, matched filtering, comparison of the amplitude of the one or more second data signals to a predetermined threshold, and sampling the amplitude of the one or more second data signals at fixed time offsets.

Embodiment C24. The system of claim C23, wherein the processor is further configured to select one or more second data signals prior to decoding data bits based on a header check, a footer check, relative strengths of the one or more second data signals, relative signal-to-noise ratios of the one or more second data signals, relative strengths of residual interference present in the one or more second data signals, and cross-correlation values of the one or more second data signals to a reference second data signal.

Embodiment C25. The system of claim C23, wherein the processor is further configured to determine one or more of a majority occurrence of a bit value, a weighted majority occurrence of a bit value, a mean bit value, and a weighted mean bit value among the decoded data bit values corresponding to two or more second data signals.

Embodiment C26. The system of claim C25, wherein the processor is configured to determine the weighted majority occurrence or the weighted mean bit value by scaling the bit value by one or more of an apodization of the transducer element on which the corresponding link scan signal or the corresponding first data signal is received, an amplitude, an energy, a signal-to-noise ratio, a time delay, a phase and a multipath time of one or more of the second data signal, the corresponding first data signal and the corresponding link scan signal.

Embodiment C27. The system of claim C1, wherein the first device comprises an implantable medical device, the second device comprises an external wireless device configured to be disposed physically separate from the first device, and the first data signal comprises an uplink data signal.

Embodiment C28. The system of claim C1, wherein the first device comprises an external wireless device, the second device comprises an implantable medical device configured to be disposed physically separate from the first device, and the first data signal comprises a downlink data signal.

Embodiment C29. The system of claim C1, wherein the first device is configured to transmit one or more of the link scan signal and the first data signal at one or more predetermined repetition intervals.

Embodiment C30. The system of claim C1, wherein the second device is further configured to transmit a wireless command to the first device, and the first device is configured to transmit the link scan signal and the first data signal in response to receiving the wireless command.

Embodiment C31. The system of claim C1, wherein one or more of the transmitted link scan signal and the transmitted first data signal comprise one or more of a reflection signal and a backscatter signal in response to receiving a wireless signal transmitted by the second device to the first device.

Embodiment C32. The system of claim C1, wherein one or more of the transmitted link scan signal and the transmitted first data signal comprise one or more of an ultrasonic signal, an acoustic signal, a vibrational signal, a radio-frequency signal, an electromagnetic signal, a magnetic signal, an electric signal, and an optical signal.

Embodiment D1. A method of decoding data signals in a wireless system, comprising:
 transmitting a link scan signal and a first data signal from a first device of the wireless system to a second device of the wireless system;
 receiving the link scan signal and the first data signal using one or more transducer elements of the second device;
 processing the received link scan signal and the received first data signal using a processor of the second device to generate a second data signal; and
 decoding the first data signal based at least in part on the second data signal.

Embodiment D2. The method of claim D1, wherein the link scan signal comprises one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals, and a plurality of pulse signals.

Embodiment D3. The method of claim D2, wherein the pulse signal or the feedback signal comprises one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

Embodiment D4. The method of claim D1, wherein the first data signal comprises one or more of on-off keying (OOK) modulation, amplitude-shift keying (ASK) modulation, pulse-position modulation (PPM), frequency-shift keying (FSK) modulation, phase-shift keying (PSK) modulation, and quadrature amplitude modulation (QAM).

Embodiment D5. The method of claim D1, further comprising selecting one or more time durations of one or more of the received link scan signal and the received first data signal prior to processing based on one or more of a predetermined timing, signal onset detection, detection of one or more of a signal rising edge and a signal falling edge, detection of one or more of a header component and a footer component of a signal, a multipath time and a drift in a frequency of one or more of the received link scan signal and the received first data signal.

Embodiment D6. The method of claim D1, wherein processing the received link scan signal comprises determining a scaled impulse response of the wireless system.

Embodiment D7. The method of claim D6, wherein the link scan signal comprises a feedback signal and determining the scaled impulse response of the wireless system comprises deconvolving a scaled received feedback signal with a scaled reference feedback signal using one or more of a frequency domain analysis and a time domain analysis.

Embodiment D8. The method of claim D7, wherein one or more of the scaled impulse response, the scaled received feedback signal, and the scaled reference feedback signal are scaled by one or more of an amplitude in the time domain, an amplitude at a frequency, an energy in one or more frequency bands, a signal-to-noise ratio for one or more of the impulse response, the received feedback signal, and the reference feedback signal, an apodization of the corresponding transducer element, a predetermined scaling factor, and a normalization scaling factor.

Embodiment D9. The method of claim D7, further comprising storing one or more of a frequency domain representation and a time domain representation of the scaled reference feedback signal into a memory of the second device.

Embodiment D10. The method of claim D7, further comprising generating one or more of a frequency domain representation and a time domain representation of the scaled reference feedback signal based on one or more properties of one or more of the received link scan signal and the received first data signal.

Embodiment D11. The method of claim D10, wherein the one or more properties of one or more of the received link scan signal and the received first data signal comprise one or more of a frequency, a duration, a number of cycles, an amplitude, a phase, and a time of arrival.

Embodiment D12. The method of claim D6, wherein processing the received link scan signal and the received first data signal comprises deconvolving a scaled received first data signal with one or more of the scaled impulse response and a scaled received link scan signal, using one or more of a frequency domain analysis and a time domain analysis, to generate the second data signal.

Embodiment D13. The method of claim D12, wherein one or more of the scaled received first data signal, the scaled impulse response and the scaled received link scan signal are scaled by an amplitude in the time domain, an amplitude at a frequency, an energy in one or more frequency bands, a signal-to-noise ratio for one or more of the received first data signal, the impulse response, and the received link scan signal, an apodization of the corresponding transducer element, a predetermined scaling factor, and a normalization scaling factor.

Embodiment D14. The method of claim D1, wherein processing the received link scan signal and the received first data signal comprises deconvolving a scaled received first data signal with a scaled received link scan signal using one or more of a frequency domain analysis and a time domain analysis, to generate the second data signal.

Embodiment D15. The method of claim D14, wherein the link scan signal comprises one or more of an impulse signal, a feedback signal, a pulse signal, a pulse signal representing a single data bit of the first data signal, a pulse signal representing a plurality of data bits of the first data signal, a plurality of impulse signals and a plurality of pulse signals.

Embodiment D16. The method of claim D1, further comprising filtering one or more of the link scan signal, the first data signal and the second data signal using one or more of a band-pass filter, a low-pass filter, a high-pass filter, an all-pass filter, a notch filter and a band-reject filter.

Embodiment D17. The method of claim D1, further comprising selecting two or more second data signals for signal combining based on one or more of a header check, a footer check, relative strengths of the two or more second data signals, relative signal-to-noise ratios of the two or more second data signals, relative signal-to-interference ratios of the two or more second data signals, relative strengths of residual interference present in the two or more second data signals, and cross-correlation values of the two or more second data signals to a reference second data signal.

Embodiment D18. The method of claim D17, wherein the reference second data signal is determined based on one or more of the second data signal's amplitude, energy, signal-to-noise ratio or signal-to-interference ratio, the corresponding first data signal's amplitude, energy, signal-to-noise ratio or signal-to-interference ratio, the corresponding link scan signal's amplitude, energy, signal-to-noise ratio or signal-to-interference ratio, and an apodization of the corresponding transducer element on which the link scan signal or the first data signal is received.

Embodiment D19. The method of claim D1, further comprising combining two or more scaled second data signals using one or more of summing, delaying and summing, averaging, and delaying and averaging to generate one or more combined data signals.

Embodiment D20. The method of claim D19, wherein the scaled second data signal is scaled by one or more of an amplitude in the time domain, an amplitude at a frequency, an energy in one or more frequency bands, a signal-to-noise ratio of the second data signal, an apodization of the corresponding transducer element, a predetermined scaling factor, and a normalization scaling factor.

Embodiment D21. The method of claim D19, further comprising selecting a combined data signal for decoding data bits based on one or more of the combined data signal's amplitude in time domain, the combined data signal's amplitude at a frequency, the combined data signal's energy in one or more frequency bands, and the combined data signal's signal-to-noise ratio.

Embodiment D22. The method of claim D19, further comprising decoding data bits based at least upon one or more combined data signals using one or more of OOK demodulation, ASK demodulation, PPM demodulation, FSK demodulation, PSK demodulation, QAM demodulation, envelope detection, matched filtering, comparison of the amplitude of the one or more combined data signals to a predetermined threshold, and sampling the amplitude of the one or more combined data signals at fixed time offsets.

Embodiment D23. The method of claim D1, further comprising decoding data bits corresponding to one or more second data signals using one or more of OOK demodulation, ASK demodulation, PPM demodulation, FSK demodulation, PSK demodulation, QAM demodulation, envelope detection, matched filtering, comparison of the amplitude of the one or more second data signals to a predetermined threshold, and sampling the amplitude of the one or more second data signals at fixed time offsets.

Embodiment D24. The method of claim D23, further comprising selecting one or more second data signals prior to decoding data bits based on a header check, a footer check, relative strengths of the one or more second data signals, relative signal-to-noise ratios of the one or more second data signals, relative strengths of residual interference present in the one or more second data signals, and cross-correlation values of the one or more second data signals to a reference second data signal.

Embodiment D25. The method of claim D23, further comprising determining one or more of a majority occurrence for a bit value, a weighted majority occurrence for a bit value, a mean bit value, and a weighted mean bit value among the decoded data bit values corresponding to two or more second data signals.

Embodiment D26. The method of claim D25, wherein determining the weighted majority occurrence or weighted mean bit value comprises scaling the bit value by one or more of an apodization of the transducer element on which the corresponding link scan signal or the corresponding first data signal is received, an amplitude, an energy, a signal-to-noise ratio, a time delay, a phase and a multipath time of one or more of the second data signal, the corresponding first data signal and the corresponding link scan signal.

Embodiment D27. The method of claim D1, wherein the first device comprises an implantable medical device, the second device comprises an external wireless device configured to be disposed physically separate from the first device, and the first data signal comprises an uplink data signal.

Embodiment D28. The method of claim D1, wherein the first device comprises an external wireless device, the second device comprises an implantable medical device configured to be disposed physically separate from the first device, and the first data signal comprises a downlink data signal.

Embodiment D29. The method of claim D1, further comprising transmitting one or more of the link scan signal and the first data signal at one or more predetermined repetition intervals.

Embodiment D30. The method of claim D1, further comprising transmitting a wireless command from the second device to the first device, and transmitting the link scan signal and the first data signal from the first device to the second device in response to receiving the wireless command by the first device.

Embodiment D31. The method of claim D1, wherein one or more of the transmitted link scan signal and the transmitted first data signal comprise one or more of a reflection signal and a backscatter signal in response to receiving a wireless signal transmitted by the second device to the first device.

Embodiment D32. The method of claim D1, wherein one or more of the transmitted link scan signal and the transmitted first data signal comprise one or more of an ultrasonic signal, an acoustic signal, a vibrational signal, a radio-frequency signal, an electromagnetic signal, a magnetic signal, an electric signal, and an optical signal.

Embodiment E1. A system configured for wireless data communication, comprising:
- a first device configured to transmit a link scan signal and a first data signal; and
- a second device comprising one or more transducer elements, and a processor, wherein
  - the one or more transducer elements are configured to receive the link scan signal and the first data signal from the first device, and
  - the processor is configured to process one or more of the received link scan signal and the received first data signal to select one or more transducer elements of the second device, and decode the first data signal based at least in part on the selected one or more transducer elements of the second device.

Embodiment E2. The system of claim E1, wherein the link scan signal comprises one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals and a plurality of pulse signals.

Embodiment E3. The system of claim E1, wherein the processor is configured to select the one or more transducer elements of the second device based on one or more of a header check, a footer check, a bit error rate, relative strengths of the link scan signals, relative signal-to-noise ratios of the link scan signals, relative signal-to-interference ratios of the link scan signals, energy of the link scan signals in one or more frequency bands, a moving mean of the link scan signal amplitude, relative strengths of the first data signals, relative signal-to-noise ratios of the first data signals, relative signal-to-interference ratios of the first data signals, energy of the first data signals in one or more frequency bands, a moving mean of the first data signal amplitude, a signal strength of an interferer, a signal strength of multipath interference, a multipath time, and apodization of the one or more transducer elements.

Embodiment F1. A method of decoding data signals in a wireless system, comprising:
- transmitting a link scan signal and a first data signal from a first device of the wireless system to a second device of the wireless system;
- receiving the link scan signal and the first data signal using one or more transducer elements of the second device;
- processing one or more of the received link scan signal and the received first data signal using a processor of the second device to select one or more transducer elements of the second device; and
- decoding the first data signal based at least in part on the selected one or more transducer elements of the second device.

Embodiment F2. The method of claim F1, wherein the link scan signal comprises one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals and a plurality of pulse signals.

Embodiment F3. The method of claim F1, wherein selecting the one or more transducer elements of the second device is based on one or more of a header check, a footer check, a bit error rate, relative strengths of the link scan signals, relative signal-to-noise ratios of the link scan signals, relative signal-to-interference ratios of the link scan signals, energy of the link scan signals in one or more frequency bands, a moving mean of the link scan signal amplitude, relative strengths of the first data signals, relative signal-to-noise ratios of the first data signals, relative signal-to-interference ratios of the first data signals, energy of the first data signals in one or more frequency bands, a moving mean of the first data signal amplitude, a signal strength of an interferer, a signal strength of multipath interference, a multipath time, and apodization of the one or more transducer elements.

Embodiment G1. A system configured to exchange wireless power or data, comprising:
- a first device configured to transmit a feedback signal; and
- a second device comprising a first transducer array, a second transducer array, and a processor, wherein
  - the first transducer array is configured to receive the feedback signal from the first device,
  - the processor is configured to extract one or more portions of the received feedback signals received by one or more transducer elements of the first transducer array, process the extracted one or more portions of the received feedback signals to generate feedback signal data, and determine a second transducer array configuration based at least in part on the feedback signal data, and
  - the second transducer array configuration is configured to exchange one or more wireless signals with the first device.

Embodiment G2. The system of claim G1, wherein the extracted one or more portions of the received feedback signal have a duration less than a duration of the received feedback signal.

Embodiment G3. The system of claim G1, wherein the duration of the feedback signal is greater than about 5 cycles of a carrier frequency of the feedback signal.

Embodiment G4. The system of claim G1, wherein the feedback signal data comprises one or more of an absolute amplitude, a relative amplitude, an absolute signal strength, a relative signal strength, an absolute phase, a relative phase, an absolute time delay and a relative time delay of the feedback signals received by one or more transducer elements of the first transducer array of the second device.

Embodiment G5. The system of claim G1, wherein the first device comprises an implantable medical device and the second device comprises an external wireless device configured to be disposed physically separate from the first device.

Embodiment G6. The system of claim G1, wherein the first transducer array and the second transducer array comprise one or more common transducer elements.

Embodiment G7. The system of claim G1, wherein the first transducer array comprises a subset of the second transducer array.

Embodiment G8. The system of claim G1, wherein the first transducer array and the second transducer array comprise distinct transducer elements.

Embodiment G9. The system of claim G1, wherein the first transducer array and the second transducer array each comprise an acoustic transducer array.

Embodiment G10. The system of claim G9, wherein the acoustic transducer array comprises an ultrasonic transducer array.

Embodiment H1. A method of exchanging wireless signals in a wireless system, comprising:
  transmitting a feedback signal from a first device of the wireless system to a second device of the wireless system;
  receiving the feedback signal using a first transducer array of the second device;
  extracting one or more portions of the received feedback signals, received by one or more transducer elements of the first transducer array of the second device, using a processor of the second device;
  processing the extracted one or more portions of the received feedback signals using the processor of the second device to generate feedback signal data;
  determining a second transducer array configuration of the second device based at least in part on the feedback signal data; and
  exchanging one or more wireless signals with the first device using the second transducer array configuration of the second device.

Embodiment H2. The method of claim H1, wherein the extracted one or more portions of the received feedback signal have a duration less than a duration of the received feedback signal.

Embodiment H3. The method of claim H1, wherein extracting one or more portions of the received feedback signal comprises finding one or more regions of the received feedback signal waveform with a settled amplitude.

Embodiment H4. The method of claim H1, wherein the duration of the transmitted feedback signal is greater than about 5 cycles of a carrier frequency of the feedback signal.

Embodiment H5. The method of claim H1, further comprising detecting one or more of a rising edge and a falling edge of the received feedback signal prior to extracting one or more portions of the received feedback signal.

Embodiment H6. The method of claim H1, wherein extracting one or more portions of the received feedback signal is performed for the feedback signals received by a subset of the elements of the first transducer array.

Embodiment H7. The method of claim H1, further comprising digitizing the feedback signal received by one or more transducer elements of the first transducer array prior to extracting one or more portions of the received feedback signal.

Embodiment H8. The method of claim H7, further comprising detecting a rising edge of the received feedback signal using analog signal processing prior to digitizing the feedback signal received by one or more transducer elements of the first transducer array.

Embodiment H9. The method of claim H1, wherein extracting one or more portions of the received feedback signal is performed using one or more of digital signal processing and analog signal processing.

Embodiment H10. The method of claim H1, wherein the feedback signal data comprises one or more of an absolute amplitude, a relative amplitude, an absolute signal strength, a relative signal strength, an absolute phase, a relative phase, an absolute time delay and a relative time delay of the feedback signals received by one or more transducer elements of the first transducer array of the second device.

Embodiment H11. The method of claim H1, wherein determining the second transducer array configuration of the second device comprises determining one or more of an amplitude, a signal strength, a phase and a time delay for transmitting wireless signals through one or more transducer elements of the second transducer array.

Embodiment H12. The method of claim H11, wherein determining the one or more of the amplitude, the signal strength, the phase and the time delay for transmitting wireless signals through one or more transducer elements of the second transducer array comprises performing one or more of cross-correlation and time reversal.

Embodiment H13. The method of claim H11, wherein determining the one or more of the amplitude, the signal strength, the phase and the time delay for transmitting wireless signals through one or more transducer elements of the second transducer array further comprises interpolation of one or more of the amplitudes, the signal strengths, the phases and the delays based on the relative spatial positions of the transducer elements of the first transducer array and the second transducer array.

Embodiment H14. The method of claim H1, wherein determining the second transducer array configuration comprises a method of closed-loop powering.

Embodiment H15. The method of claim H1, wherein the first device comprises an implantable medical device and the second device comprises an external wireless device configured to be disposed physically separate from the first device.

Embodiment H16. The method of claim H1, wherein the first transducer array and the second transducer array comprise one or more common transducer elements.

Embodiment H17. The method of claim H1, wherein the first transducer array comprises a subset of the second transducer array.

Embodiment H18. The method of claim H1, wherein the first transducer array and the second transducer array comprise distinct transducer elements.

Embodiment H19. The method of claim H1, wherein the first transducer array and the second transducer array each comprise an acoustic transducer array.

Embodiment H20. The method of claim H19, wherein the acoustic transducer array comprises an ultrasonic transducer array.

Embodiment I1. A system configured to exchange wireless power or data, comprising:
  a first device configured to transmit a link scan signal; and
  a second device comprising a first transducer array, a second transducer array, and a processor, wherein
    the first transducer array is configured to receive the link scan signal from the first device,
    the processor is configured to process the received link scan signals received by one or more transducer elements of the first transducer array of the second device to generate link scan signal data, and determine a second transducer array configuration based at least in part on the link scan signal data, and
    the second transducer array configuration is configured to exchange one or more wireless signals with the first device.

Embodiment I2. The system of claim I1, wherein the link scan signal comprises one or more of an impulse signal and a pulse signal.

Embodiment I3. The system of claim I2, wherein the pulse signal comprises one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

Embodiment I4. The system of claim I1, wherein the first device comprises an implantable medical device and the second device comprises an external wireless device configured to be disposed physically separate from the first device.

Embodiment I5. The system of claim I1, wherein the first transducer array and the second transducer array comprise one or more common transducer elements.

Embodiment I6. The system of claim I1, wherein the first transducer array comprises a subset of the second transducer array.

Embodiment I7. The system of claim I1, wherein the first transducer array and the second transducer array comprise distinct transducer elements.

Embodiment I8. The system of claim I1, wherein the first transducer array and the second transducer array each comprise an acoustic transducer array.

Embodiment I9. The system of claim I8, wherein the acoustic transducer array comprises an ultrasound transducer array.

Embodiment J1. A method of exchanging wireless signals in a wireless system, comprising:
  transmitting a link scan signal from a first device of the wireless system to a second device of the wireless system;
  receiving the link scan signal using a first transducer array of the second device;
  processing the received link scan signals, received by one or more transducer elements of the first transducer array of the second device, using a processor of the second device to generate link scan signal data;
  determining a second transducer array configuration of the second device based at least in part on the link scan signal data; and
  exchanging one or more wireless signals with the first device using the second transducer array configuration of the second device.

Embodiment J2. The method of claim J1, wherein the link scan signal comprises one or more of an impulse signal and a pulse signal.

Embodiment J3. The method of claim J2, wherein the pulse signal comprises one or more cycles of a carrier frequency of the pulse signal.

Embodiment J4. The method of claim J1, wherein processing the received link scan signal received by a transducer element of the first transducer array comprises determining an impulse response of the wireless system.

Embodiment J5. The method of claim J4, wherein processing the received link scan signal further comprises performing convolution of the impulse response of the wireless system corresponding to one or more transducer elements of the first transducer array with one or more template signals.

Embodiment J6. The method of claim J5, wherein the link scan signal data comprises the output signal of the convolution.

Embodiment J7. The method of claim J5, wherein the link scan signal data comprises one or more of an absolute amplitude, a relative amplitude, an absolute signal strength, a relative signal strength, an absolute phase, a relative phase, an absolute time delay and a relative time delay of the output signal of the convolution.

Embodiment J8. The method of claim J5, wherein the template signal comprises a pulse signal.

Embodiment J9. The method of claim J5, wherein the duration of the template signal is greater than about 5 cycles of a carrier frequency of the template signal.

Embodiment J10. The method as in any of claims J2 or J8, wherein the pulse signal comprises one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

Embodiment J11. The method of claim J1, wherein determining the second transducer array configuration of the second device comprises determining one or more of an amplitude, a signal strength, a phase and a time delay for transmitting wireless signals through one or more transducer elements of the second transducer array.

Embodiment J12. The method of claim J11, wherein determining the one or more of the amplitude, the signal strength, the phase and the time delay for transmitting wireless signals through one or more transducer elements of the second transducer array comprises performing one or more of cross-correlation and time reversal.

Embodiment J13. The method of claim J11, wherein determining the one or more of the amplitude, the signal strength, the phase and the time delay for transmitting wireless signals through one or more transducer elements of the second transducer array further comprises interpolation of one or more of the amplitudes, the signal strengths, the phases and the time delays based on the relative spatial positions of the transducer elements of the first transducer array and the second transducer array.

Embodiment J14. The method of claim J1, wherein determining the second transducer array configuration comprises a method of closed-loop powering.

Embodiment J15. The method of claim J1, wherein the first device comprises an implantable medical device and the second device comprises an external wireless device configured to be disposed physically separate from the first device.

Embodiment J16. The method of claim J1, wherein the first transducer array and the second transducer array comprise one or more common transducer elements.

Embodiment J17. The method of claim J1, wherein the first transducer array comprises a subset of the second transducer array.

Embodiment J18. The method of claim J1, wherein the first transducer array and the second transducer array comprise distinct transducer elements.

Embodiment J19. The method of claim J1, wherein the first transducer array and the second transducer array each comprise an acoustic transducer array.

Embodiment J20. The method of claim J19, wherein the acoustic transducer array comprises an ultrasound transducer array.

Embodiment K1. A system configured to exchange wireless power or data, comprising:
  a first device configured to transmit a link scan signal and a feedback signal; and
  a second device comprising a first transducer array, a second transducer array, and a processor, wherein the first transducer array is configured to receive the link scan signal and the feedback signal from the first device, the processor is configured to process the received link scan signals and the received feedback signals received by one or more transducer elements of the first transducer array to generate feedback signal data, and determine a second transducer array configuration based at least in part on the feedback signal data, and the second transducer array configuration is configured to exchange one or more wireless signals with the first device.

Embodiment L1. A method of exchanging wireless signals in a wireless system, comprising:

transmitting a link scan signal and a feedback signal from a first device of the wireless system to a second device of the wireless system;

receiving the link scan signal and the feedback signal using a first transducer array of the second device;

processing the received link scan signals and the received feedback signals, received by one or more transducer elements of the first transducer array of the second device, using a processor of the second device to generate feedback signal data;

determining a second transducer array configuration of the second device based at least in part on the feedback signal data; and exchanging one or more wireless signals with the first device using the second transducer array configuration of the second device.

Embodiment L2. The method of claim L1, wherein the link scan signal comprises one or more of an impulse signal and a pulse signal.

Embodiment L3. The method of claim L2, wherein the pulse signal comprises one or more of a rectangular pulse, a Dirac pulse, a sinusoidal pulse, a triangular pulse, a trapezoidal pulse, a raised cosine pulse, a sinc pulse, a Gaussian pulse, and one or more cycles of a carrier frequency of the pulse signal.

Embodiment L4. The method of claim L1, wherein processing the received link scan signal and the received feedback signal comprises performing deconvolution of the received feedback signal with the received link scan signal.

Embodiment L5. The method of claim L1, wherein processing the received link scan signal received by a transducer element of the first transducer array comprises determining an impulse response of the wireless system.

Embodiment L6. The method of claim L5, wherein processing the received link scan signal and the received feedback signal comprises performing deconvolution of the received feedback signal with the impulse response of the wireless system.

Embodiment L7. The method of claim L6, further comprising extracting one or more portions of the output signal of the deconvolution using a processor of the second device.

Embodiment L8. The method of claim L7, wherein extracting the one or more portions of the output signal of the deconvolution comprises finding one or more regions of the output signal of the deconvolution with a settled amplitude.

Embodiment L9. The method of claim L1, wherein determining the second transducer array configuration of the second device comprises determining one or more of an amplitude, a signal strength, a phase and a time delay for transmitting wireless signals through one or more transducer elements of the second transducer array.

Embodiment L10. The method of claim L9, wherein determining the one or more of the amplitude, the signal strength, the phase and the time delay for transmitting wireless signals through one or more transducer elements of the second transducer array comprises performing one or more of cross-correlation and time reversal.

Embodiment L11. The method of claim L9, wherein determining the one or more of the amplitude, the signal strength, the phase and the time delay for transmitting wireless signals through one or more transducer elements of the second transducer array further comprises interpolation of one or more of the amplitudes, the signal strengths, the phases and the delays based on the relative spatial positions of the transducer elements of the first transducer array and the second transducer array.

Embodiment L12. The method of claim L11, wherein determining the second transducer array configuration comprises a method of closed-loop powering.

Embodiment M1. A method of decoding data signals in a wireless system, comprising:

transmitting a link scan signal from a first device of the wireless system to a second device of the wireless system;

receiving the link scan signal using one or more transducer elements of the second device;

processing the received link scan signal using a processor of the second device to generate link scan signal data;

generating a pre-distorted data signal based on the link scan signal data using the processor of the second device;

transmitting the pre-distorted data signal from the second device to the first device;

receiving the pre-distorted data signal using one or more transducer elements of the first device; and processing the received pre-distorted data signal using a processor of the first device to generate decoded data.

Embodiment M2. The method of claim M1, wherein the link scan signal comprises an impulse signal, and generating the pre-distorted data signal comprises performing deconvolution of a data signal with the received link scan signal.

Embodiment M3. The method of claim M1, wherein the link scan signal data comprises an impulse response of the wireless system, and generating the pre-distorted data signal comprises performing deconvolution of a data signal with the impulse response of the wireless system.

Embodiment M4. The method of claim M1, wherein the first device comprises an implantable medical device, the second device comprises an external wireless device configured to be disposed physically separate from the first device, and the pre-distorted data signal comprises a downlink data signal.

Embodiment M5. The method of claim M1, wherein the first device comprises an external wireless device, the second device comprises an implantable medical device configured to be disposed physically separate from the first device, and the pre-distorted data signal comprises an uplink data signal.

Embodiment N1. A method of decoding data signals in a wireless system, comprising:

transmitting a data signal from a first device of the wireless system to a second device of the wireless system;

receiving the data signal using a plurality of transducer elements of the second device;

applying predetermined delays to one or more received data signals, received using the plurality of transducer elements of the second device, using a processor of the second device to generate delayed data signals;
  summing two or more delayed data signals using the processor of the second device to generate one or more delayed and summed data signals; and
  decoding the data signal using the processor of the second device based at least in part on the one or more delayed and summed data signals.

Embodiment N2. The method of claim N1, further comprising:
  transmitting a feedback signal from the first device to the second device prior to transmitting the data signal;
  receiving the feedback signal using one or more transducer elements of the second device;
  processing the received feedback signal using the processor of the second device to generate feedback signal data; and
  computing the predetermined delays based at least in part on the feedback signal data.

Embodiment N3. The method of claim N1, further comprising:
  transmitting a link scan signal from the first device to the second device prior to transmitting the data signal;
  receiving the link scan signal using one or more transducer elements of the second device;
  processing the received link scan signal using the processor of the second device to generate link scan signal data; and
  computing the predetermined delays based at least in part on the link scan signal data.

Embodiment N4. The method of claim N1, wherein the first device comprises an implantable medical device, the second device comprises an external wireless device configured to be disposed physically separate from the first device, and the data signal comprises an uplink data signal.

Embodiment N5. The method of claim N1, wherein the first device comprises an external wireless device, the second device comprises an implantable medical device configured to be disposed physically separate from the first device, and the data signal comprises a downlink data signal.

Embodiment O1. A method of calibrating a wireless system, comprising:
  transmitting one or more test signals comprising one or more carrier frequencies from a first device of the wireless system to a second device of the wireless system;
  receiving the one or more test signals using the second device;
  processing the one or more received test signals using a processor of the second device to generate test signal data;
  determining one or more selected carrier frequencies using the processor of the second device based at least in part on the test signal data;
  transmitting one or more wireless commands from the second device to the first device comprising information corresponding to the one or more selected carrier frequencies; and
  storing the information corresponding to the one or more selected carrier frequencies in a memory of the first device.

Embodiment O2. The method of claim O1, further comprising transmitting a wireless signal comprising the one or more selected carrier frequencies from the first device to the second device.

Embodiment O3. The method of claim O2, wherein the transmitted wireless signal comprises one or more of a feedback signal, a link scan signal, and an uplink data signal.

Embodiment O4. The method of claim O1, wherein determining one or more selected carrier frequencies comprises determining one or more carrier frequencies at which a parameter of the received test signal has a value greater than a predetermined threshold.

Embodiment O5. The method of claim O4, wherein the parameter of the received test signal comprises one or more of a signal strength, a signal amplitude, a signal power, a signal energy, a signal-to-noise ratio, a signal-to-interference ratio, a link efficiency, and a link gain.

Embodiment O6. The method of claim O1, wherein the memory of the first device comprises one or more of a non-volatile memory and a volatile memory.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed: obviously, many modifications and variations are possible in view of the above teachings. The variations were chosen and described in order to best explain the principles of the invention and its practical applications, and they thereby enable others skilled in the art to best utilize the invention and various implementations with various modifications as are suited to the particular use contemplated. It is intended that the following claims and their equivalents define the scope of the invention.

The invention claimed is:

1. A method of exchanging wireless signals in a wireless system, comprising:
  transmitting a feedback signal with a first duration from a first device of the wireless system to a second device of the wireless system;
  receiving the feedback signal for a second duration using one or more transducer elements of a transducer array of the second device;
  processing the feedback signal received in the second duration using one or more transducer elements of the transducer array to generate feedback signal data using a processor of the second device;
  determining a transducer array configuration of the second device based at least in part on the feedback signal data using the processor of the second device; and
  exchanging one or more wireless signals with the first device using the transducer array configuration of the second device.

2. The method of claim 1, wherein the second duration is greater than the first duration.

3. The method of claim 1, wherein the feedback signal data comprises one or more of an absolute amplitude or magnitude, a relative amplitude or magnitude, an absolute signal strength, a relative signal strength, signal energy in one or more frequency bands, an apodization, an absolute phase, a relative phase, an absolute time delay, a relative time delay, an absolute time of arrival, a relative time of arrival, a frequency, a time duration, number of cycles, an absolute signal-to-noise ratio, and a relative signal-to-noise ratio of the feedback signal received within the second duration by one or more transducer elements of the transducer array.

4. The method of claim 1, wherein the transducer array configuration comprises one or more of a selection of a set of transducer elements, an apodization, a signal strength, a voltage level, a current level, a pulse width, pulse width modulation, a duty cycle of a signal, a phase, a time delay, a frequency and a transmit duration applied to one or more transducer elements of the transducer array for transmitting wireless signals to the first device.

5. The method of claim 4, wherein one or more of the phases and the time delays applied to the one or more transducer elements of the transducer array for transmitting wireless signals to the first device are based on one or more of the relative phases of the received feedback signal in the second duration at a predetermined frequency and the time of arrival of the feedback signal received using the one or more transducer elements.

6. The method of claim 1, wherein the feedback signal comprises one or more of an impulse signal and a pulse signal.

7. The method of claim 1, wherein processing the feedback signal or determining the transducer array configuration of the second device comprises one or more of a time domain analysis, a frequency domain analysis, and an interpolation analysis.

8. The method of claim 7, wherein the frequency domain analysis comprises computing one or more of a Fourier transform, a discrete Fourier transform (DFT) and a discrete-time Fourier transform (DTFT) at one or more predetermined frequencies.

9. The method of claim 1, wherein the first device comprises an implantable medical device, and the second device comprises an external wireless device configured to be disposed physically separate from the first device.

10. The method of claim 1, wherein the transmitted feedback signal comprises one or more of an ultrasonic signal, an acoustic signal, a vibrational signal, a radio-frequency signal, an electromagnetic signal, a magnetic signal, an electric signal, and an optical signal.

11. A method of decoding data signals in a wireless system, comprising:
  transmitting a link scan signal and a first data signal from a first device of the wireless system to a second device of the wireless system;
  receiving the link scan signal and the first data signal using one or more transducer elements of the second device;
  processing the received link scan signal and the received first data signal using a processor of the second device to generate a second data signal; and
  decoding the first data signal based at least in part on the second data signal.

12. The method of claim 11, wherein the link scan signal comprises one or more of a feedback signal, an impulse signal, a pulse signal, a pulse signal representing a single data bit of the first data signal, a pulse signal representing a plurality of data bits of the first data signal, a header signal, a footer signal, a predetermined digital code, a continuous-wave signal, a plurality of impulse signals, and a plurality of pulse signals.

13. The method of claim 11, wherein the first data signal comprises one or more of on-off keying (OOK) modulation, amplitude-shift keying (ASK) modulation, pulse-position modulation (PPM), frequency-shift keying (FSK) modulation, phase-shift keying (PSK) modulation, and quadrature amplitude modulation (QAM).

14. The method of claim 11, wherein processing the received link scan signal comprises determining a scaled impulse response of the wireless system.

15. The method of claim 14, wherein the link scan signal comprises a feedback signal and determining the scaled impulse response of the wireless system comprises deconvolving a scaled received feedback signal with a scaled reference feedback signal using one or more of a frequency domain analysis and a time domain analysis.

16. The method of claim 14, wherein processing the received link scan signal and the received first data signal comprises deconvolving a scaled received first data signal with one or more of the scaled impulse response and a scaled received link scan signal, using one or more of a frequency domain analysis and a time domain analysis, to generate the second data signal.

17. The method of claim 11, further comprising combining two or more scaled second data signals using one or more of summing, delaying and summing, averaging, and delaying and averaging to generate one or more combined data signals.

18. The method of claim 17, further comprising decoding data bits based at least upon one or more combined data signals using one or more of OOK demodulation, ASK demodulation, PPM demodulation, FSK demodulation, PSK demodulation, QAM demodulation, envelope detection, matched filtering, comparison of the amplitude of the one or more combined data signals to a predetermined threshold, and sampling the amplitude of the one or more combined data signals at fixed time offsets.

19. The method of claim 11, wherein the first device comprises an implantable medical device, the second device comprises an external wireless device configured to be disposed physically separate from the first device, and the first data signal comprises an uplink data signal.

20. The method of claim 11, wherein one or more of the transmitted link scan signal and the transmitted first data signal comprise one or more of an ultrasonic signal, an acoustic signal, a vibrational signal, a radio-frequency signal, an electromagnetic signal, a magnetic signal, an electric signal, and an optical signal.

* * * * *